United States Patent
Baird et al.

(10) Patent No.: US 7,049,061 B1
(45) Date of Patent: May 23, 2006

(54) STEREOCHEMICAL CONTROL OF THE DNA BINDING AFFINITY, SEQUENCE SPECIFICITY, AND ORIENTATION-PREFERENCE OF CHIRAL HAIRPIN POLYAMIDES IN THE MINOR GROOVE

(75) Inventors: Eldon E. Baird, Foster City, CA (US); Peter B. Dervan, San Marino, CA (US)

(73) Assignee: California Institute of Technology, Pasadena, CA (US)

(*) Notice: Subject to any disclaimer, the term of this patent is extended or adjusted under 35 U.S.C. 154(b) by 0 days.

(21) Appl. No.: 09/374,702

(22) Filed: Aug. 12, 1999

Related U.S. Application Data

(63) Continuation-in-part of application No. PCT/US97/12722, filed on Jul. 21, 1997, and a continuation-in-part of application No. 08/853,522, filed on May 8, 1997, now Pat. No. 6,635,417, which is a continuation-in-part of application No. 08/837,524, filed on Apr. 21, 1997, now Pat. No. 6,143,901, and a continuation-in-part of application No. PCT/US97/03332, filed on Feb. 20, 1997, and a continuation-in-part of application No. 08/607,078, filed on Feb. 26, 1996, now Pat. No. 6,090,947.

(60) Provisional application No. 60/042,022, filed on Apr. 16, 1997, provisional application No. 60/043,444, filed on Apr. 8, 1997, provisional application No. 60/038,384, filed on Feb. 14, 1997, provisional application No. 60/026,713, filed on Sep. 25, 1996, provisional application No. 60/024,374, filed on Aug. 1, 1996, and provisional application No. 60/023,309, filed on Jul. 31, 1996.

(51) Int. Cl.
*C12Q 1/68* (2006.01)
*A01N 43/04* (2006.01)
*A61K 38/00* (2006.01)
*C07K 1/00* (2006.01)

(52) U.S. Cl. ............................ 435/6; 514/2; 514/44; 530/300; 530/350

(58) Field of Classification Search ............ 435/6; 514/2, 44; 500/300, 350; 436/501
See application file for complete search history.

(56) References Cited

U.S. PATENT DOCUMENTS

| 4,795,700 A | 1/1989 | Dervan et al. ............ 435/5 |
| 5,539,083 A | 7/1996 | Cook et al. ............ 530/333 |

(Continued)

FOREIGN PATENT DOCUMENTS

| DE | 43 31 012 A1 | 3/1995 |
| EP | 0 246 868 A1 | 11/1987 |

(Continued)

OTHER PUBLICATIONS

Herman et al., J. Am. Chem. Soc., vol. 120, pp. 1382–1391, 1998.*

(Continued)

*Primary Examiner*—Ardin H. Marschel
(74) *Attorney, Agent, or Firm*—Foley & Lardner LLP

(57) ABSTRACT

This invention provides improved polyamides comprising a hairpin loop derived from γ-aminobutyric acid which bind to the minor groove of a promoter regions of a DNA sequence. Binding of the polyamide to the DNA sequence of the promoter region inhibits expression of the requisite gene. The improvement relates to the use of R-2,4-diaminobutyric acid and derivatives of the 2-amino group to form the hairpin loop. The improved asymmetric hairpin provides for tighter binding of the polyamides to the minor groove of DNA and additionally provides an amine function for derivatizing polyamides by, for example, forming amide linkages. Such derivatives may serve to attach detectable labels to the polyamide.

33 Claims, 26 Drawing Sheets

U.S. PATENT DOCUMENTS

| | | | |
|---|---|---|---|
| 5,563,250 A | 10/1996 | Hylarides et al. | 536/4.1 |
| 5,578,444 A | 11/1996 | Edwards et al. | 435/6 |
| 5,693,463 A | 12/1997 | Edwards et al. | 435/6 |
| 5,726,014 A | 3/1998 | Edwards et al. | 435/6 |
| 5,738,990 A | 4/1998 | Edwards et al. | 435/6 |
| 5,801,155 A | 9/1998 | Kutyavin et al. | 514/44 |

FOREIGN PATENT DOCUMENTS

| | | |
|---|---|---|
| EP | 0 388 948 A1 | 9/1990 |
| GB | 2 261 661 A | 5/1993 |
| WO | 92/09574 | 6/1992 |
| WO | 92/13838 | 8/1992 |
| WO | 92/14707 | 9/1992 |
| WO | 93/00446 | 1/1993 |
| WO | 94/03434 | 2/1994 |
| WO | 94/14980 | 7/1994 |
| WO | 94/20463 | 9/1994 |
| WO | 94/25436 | 11/1994 |
| WO | 95/04732 | 2/1995 |
| WO | 96/05196 | 2/1996 |
| WO | 96/32496 | 10/1996 |
| WO | 97/30975 | 8/1997 |

OTHER PUBLICATIONS

Abu–Daya et al., "DNA sequence preferences of several AT–selective minor groove binding ligands," *Nucleic Acids Research* 23:3385–3392 (1995).

Abu–Daya et al., "Interaction of minor groove binding ligands with long AT tracts," *Nucleic Acids Research* 25:4962–4969 (1997).

Aleman et al., "Toward an Understanding of the Drug–DNA Recognition Mechanism. Hydrogen–Bond Strength in Netropsin–DNA Complexes," *J. Phys. Chem.* 100:11480–11487 (1996).

Al–Said et al., "A convenient synthesis of cross–linked homodimeric bis–lexitropsins," *Synth. Commun.* 25(7):1059–1070 (1995).

Al–Said et al., "Synthesis of novel cross–linked bis–lexitropsins," *Tetrahedron Lett.* 35(41):7577–7580 (1994).

Andronikashvili et al., "Spectral Manifestations of the Action of $Zn^{2+}$ Ions on DNA Complexes with Distamycin," *Biophysics* 33:824–829 (1988).

Arcamone et al., "Structure and synthesis of Distamycin A," *Nature* 203:1064–1065 (1964).

Arcamone et al., "Synthesis, DNA binding and antiviral activity of distamycin analogues containing different heterocyclic moieties," *Anti–Cancer Drug Design* 1:235–244 (1986).

Bailly et al., "Depsipeptide Analogs of the Antitumor Drug Distamycin Containing Thiazole Amino Acids Residues," *Tetrahedron* 44:5833–5843 (1988).

Bailly et al., "Design, Synthesis, DNA Binding, and Biological Activity of a Series of DNA Minor–Groove–Binding Intercalating Drugs," *Journal of Pharmaceutical Sciences* 78:910–917 (1989).

Bailly et al., "Subcellular Distribution of a Nitroxide Spin–Labeled Netropsin in Living KB Cells," *Biochemical Pharmacology* 38:1625–1630 (1989).

Baird and Dervan, "Solid Phase Synthesis of Polyamdies Containing Imidazole and Pyrrole Amino Acids," *J. Am. Chem. Soc.* 118:6141–6146 (1996).

Baker and Dervan, "Sequence–Specific Cleavage of DNA by N–Bromoacetyldistamycin. Product and Kinetic Analyses," *J. Am. Chem. Soc.* 111:2700–2712 (1989).

Baker and Dervan, "Sequence–Specific Cleavage of Double–Helix DNA. N–Bromoacetyldistamycin," *J. Am. Chem. Soc.* 107:8266–8268 (1985).

Baliga et al., "RecA–oligonucleotide filaments bind in the minor groove of double–stranded DNA," *Proc. Natl. Acad. Sci. USA* 92:10393–10397 (1995).

Beal and Dervan, "Recognition of Double Helical DNA by Alternate Strand Triple Helix Formation," *J. Am. Chem. Soc.* 114:4976–4982 (1992).

Best and Dervan, "Energetics of Formation of Sixteen Triple Helical Complexes Which Vary at a Single Position within a Pyrimidine Motif," *J. Am. Chem. Soc.* 117:1187–1193 (1995).

Bianchi et al., "Alteration of the Expression of Human Estrogen Receptor Gene by Distamycin," *J. Steroid Biochem. Molec. Biol.* 54:211–215 (1995).

Borodulin et al., "Interaction of Ligand of the bis–Netropsin Type with Poly(dA)·Poly(dT). Optical, Structural, and Energetic Characteristics of AT–Specific Binding," *Institute of Molecular Biology*, Academy of Sciences of USSR, pp. 929–934 (1987) translated from *Molekulyarnaya Biologiya* 20(4):1144–1149 (1986).

Borodulin et al., "New Modes of Ligand Interaction with DNA: A Trimeric bis–Netropsin Complex with Poly-(dA–dT)," *Molecular Biology* 30:661–665 (1996).

Botella and Nieto, "The C–terminal DNA–binding domain of *Chironomus* BR gene products shows preferentially affinity for (dA·dT)–rich sequences," *Mol Gen Genet* 251:422–427 (1996).

Brabec and Balcarova, "459—The Effect of Netropsin on the Electrochemical Oxidation of DNA at a Graphite Electrode," *Bioelectrochemistry & Bioenergetics* 9:245–252 (1982).

Broggini et al., "Modulations of transcription factor–DNA interactions by anticancer drugs," *Anti–Cancer Drug Design* 9:373–387 (1994).

Bruice et al., "Rational design of substituted tripyrrole peptides that complex with DNA by both selective minor-–groove binding and electrostatic interaction with the phosphate backbone," *Proc. Natl. Acad. Sci. USA* 89:1700–1704 (1992).

Bruzik et al., "Specific Activation of Transcription Initiation by the Sequence–Specific DNA–Binding Agents Distamycin A and Netropsin," *Biochemistry* 26:950–956 (1987).

Burckhardt et al., "Reversal of the Z– to B–Conformation of Poly(dA–dT)·Poly(dA–dT) Induced by Netropsin and Distamycin A," *Journal of Biomolecular Structure & Dynamics* 13:671–676 (1996).

Burckhardt et al., "Two Binding Modes of Netropsin are Involved in the Complex Formation with Poly(dA–dT)·Poly(dA–dT) and other Alternating DNA Duplex Polymers," *Journal of Biomolecular Structure and Dynamics* 2:721–736 (1985).

Burckhardt et al., "Variation of DNA sequence specificity of DNA–oligopeptide binding ligands related to netropsin: imidazole–containing lexitropsins," *Biochimica et Biophysica Acta* 1009:11–18 (1989).

Burridge et al., "Electrostatic potential and binding of drugs to the minor groove of DNA," 5(3):165–166 (Sep. 1987).

Cartwright et al., "Cleavage of chromatin with methidiumpropyl–EDTA·iron(II)," *Proc. Natl. Acad. Sci. USA* 80:3213–3217 (1983).

Chai and Alonso, "Distamycin–induced inhibition of formation of a nucleoprotein complex between the terminase small subunit of G1P and the non–encapsidated end (pacL site) of *Bacillus subtilis* bacteriophage SPP1," *Nucleic Acids Research* 24:282–288 (1996).

Chaloupka and Kucerova, "Netropsin increases formation of mRNA coding for a neutral metalloproteinase in *Bacillus megaterium*," *J. Basic Microbiol.* 28:11–16 (1988).

Chandra et al., "Some Structural Requirements for the Antibiotic Action of Distamycins," *FEBS Letters* 16:249–252 (1971).

Chang et al., "On the importance of van der Waals interaction in the groove binding of DNA with ligands: restrained molecular dynamics study," International Journal of Biological Macromolecules 19:279–285 (1996).

Chen et al., "Design of Distamicin Analogues to Probe the Physical Origin of the Antiparallel Side by Side Oligopeptide Binding Motif in DNA Minor Groove Recognition," *Biochemical and Biophysical Research Communications* 220:213–218 (1996).

Chen et al., "Only one of the two DNA–bound orientations of AP–1 found in solution cooperates with NFATp," *Current Biology* 5:882–889 (1995).

Chen et al., "Optimization of Cross–Linked Lexitropsins," *Journal of Biomolecular Structure & Dynamics* 14:341–355 (1996).

Chen et al., "Design and synthesis of sequence–specific DNA minor groove recognizing ligands of the cross–linked lexitropsin class," *Heterocycles* 41(8):1691–1707 (1995).

Chen et al., "DNA minor groove binding of cross–linked lexitropsins: Experimental conditions required to observe the covalently linked WPPW (Groove wall peptide–peptide–groove wall)motif," *Biophys. J.* 68(5):2041–2048 (1995).

Chen et al., "A new DNA minor groove binding motif: Cross–linked lexitropsins," *J. Am. Chem. Soc.* 116(16):6995–7005 (1994).

Chen, "Design, synthesis and evaluation of novel bismustard cross–linked lexitropsins," *Bioorg. Med. Chem. Lett.* 5(19):2223–2228 (1995).

Chiang et al., "Effect of DNA–binding Drugs on Early Growth Response Factor–I and TATA Box–binding Protein Complex Formation with the Herpes Simplex Virus Latency Promoter," *J. Biol. Chem.* 271:23999–24004 (1996).

Cho et al., "Cyclic polyamides for recognition in the minor groove of DNA," *Proc. Natl. Acad. Sci. USA* 92:10389–10392 (1995).

Colocci and Dervan, "Cooperative Binding of 8–mer Oligonucleotides Containing 5–(1–Propynyl)–2'–deoxyuridine to Adjacent DNA Sites by Triple–Helix Formation," *J. Am. Chem. Soc.* 116:785–786 (1994).

Colocci and Dervan, "Cooperative Triple–Helix Formation at Adjacent DNA Sites: Sequence Composition Dependence at the Junction," *J. Am. Chem. Soc.* 117:4781–4787 (1995).

Colocci et al., "Cooperative Oligonucleotide–Directed Triple Helix Formation at Adjacent DNA Sites," *J. Am. Chem.Soc.* 115:4468–4473 (1993).

Colson et al., "Electric linear dichroism as a new tool to study sequence preference in drug binding to DNA," *Biophysical Chemistry* 58:125–140 (1996).

Dasgupta et al., "DNA–Binding Characteristics of a Synthetic Analogue of Distamycin," *Biochemical and Biophysical Research Communications* 140:626–631 (1986).

Dasgupta et al., "Interaction of Synthetic Analogues of Distamycin with Poly(dA–dT): Role of the Conjugated N–Methylpyrrole System," *Biochemistry* 26:6381–6386 (1987).

Debart et al., "Synthesis, DNA Binding, and Biological Evalution of Synthetic Precursors and Novel Analogues of Netropsin," *J. Med. Chem.* 32:1074–1083 (1989).

Dervan, "113. A Chemical Approach to the Single Site Cleavage of Human Chromosomes," *Abstracts, Division of Biological Chemistry* 31:2209 (1992).

Dervan, "83. Synthetic Sequence Specific DNA Binding Molecules," *Abstracts, Division of Biological Chemistry* 26:4171 (1987).

Dervan, "Design of Sequence–Specific DNA–Binding Molecules," *Science* 232:464–471 (1986).

Dervan, "Reagents for the site–specific cleavage of megabase DNA," *Nature* 359:87–88 (1992).

Di Marco et al., "Experimental Studies on Distamycin A—A New Antibiotic with Cytotoxic Activity," *Cancer Chemotherapy Reports* 18:15–19 (1962).

Di Marco et al., "Selective Inhibition of the Multiplication of Phage T1 in *E. coli* K12," *Experientia* 19:134–136 (1963).

Di Pietro et al., "N–Formimidoyl analogues of distamycin," *J. Chem. Soc., Perkin Trans. 1*, pp. 1333–1335 (1996).

D'Incalci et al., "Studies on the Mode of Action of FCE 24517, a New Distamycin A Derivative," *Proceedings of AACR* 29:329 at abstract No. 1310 (1988).

Ding et al., "The preparation of partially protected 3–amino–1–methylpyrazole–5–carboxylic acids to be used as intermediates in the synthesis of analogs of distamycin–A," Acta Chemica Scandivavica 44(1):75–81 (1990).

Ding et al., "Synthesis and antiviral activity of three pyrazole analogues of distamycin A," Acta Chemica Scandinavica 48:498–505 (1994).

Distefano and Devran, "Energetics of cooperative binding olgionucleotides with discrete dimerization domains to DNA by triple helix formation," *Proc. Natl. Acad. Sci. USA* 90:1179–1183 (1993).

Distefano and Dervan, "Ligand–Promoted Dimerization of Oligonucleotides Binding Cooperatively to DNA," *J. Am. Chem. Soc.* 114:11006–11007 (1992).

Dorn et al., "Dystamycin– induced inhibitor of homeodomain DNA complexes," EMBO Journal 11:279–286 (1992).

Dreyer and Dervan, "Sequence–specific cleavage of single–stranded DNA: Oligonucleotide–EDTA·Fe(II)," *Proc. Natl. Acad. Sci. USA* 82:968–972 (1985).

Dunner et al., "Enhancement of a Fre(16)(q22) with Distamycin A: A Family Ascertained Through an Abnormal Proposita," *American Journal of Medical Genetics* 16:277–284 (1983).

Durand and Maurizot, "Distamycin A Complexation with a Nucleic Acid Triple Helix," *Biochemistry* 35:9133–9139 (1986).

Dwyer et al., "Structural Analysis of Covalent Peptide Dimers, Bis(pyridine–2–carboxamidonetropsin)$(CH_2)_{3-6}$, in Complex with 5'–TGACT–3' Sites by Two–Dimensional NMR," *J. Am. Chem. Soc.* 115:9900–9906 (1993).

Eliadis et al., "The Synthesis and DNA Footprinting of Acridine–linked Netropsin and Distamycin Bifunctional Mixed Ligands," *J. Chem. Soc. Chem. Commun.* 1049–1052 (1988).

Feng et al., "Hin recombinase bound to DNA: The origin of specificity in major and minor groove interactions," Science 236:348–355 (1994).

Feng et al., "Crystallization and preliminary X–ray analysis of the DNA binding domain of the Hin recombinase with its DNA binding site," J. Mol. Biol. 232:982–986 (1993).

Fesen and Pommier, "Topoisomerase Inhibition by Anticancer Drugs is Antagonized by Distamycin," *Proceedings of AACR* 29:276 at abstract No. 1095 (1988).

Filipowsky et al., "Linked lexitropsins and the in vitro inhibition of HIV–1 reverse transcriptase RNA–directed DNA polymerization: A novel induced–fit of 3,5 m–pyridyl bisdistamycin to enzyme–associated template primer," Biochemistry 35(48)15397–15410 (1996).

Fish et al., "Determination of Equilibrium Binding Affinity of Distamycin and Netropsin to the Synthetic Deoxyolignucleotide Sequence d(GGTATACC)$_2$ by Quantitative DNase 1 Footprinting," *Biochemistry* 27:6026–6032 (1988).

Fox and Waring, "DNA structural variations produced by actinomycin and distamycin as revealed by DNAse I footprinting," *Nucleic Acids Research* 12:9271–9285 (1984).

Fransson et al., "High–performance liquid chromatography of distamycin A and its primary decomposition products as well as some synthetic analogues," *Journal of Chromatograpy* 268:347–351 (1983).

Frigerio et al., "Determination of FCE 26644, a new polysulphonated derivative of distamycin A, in monkey plasma by reversed–phase ion–pair high–performance liquid chromatography with ultraviolet detection," *Journal of Chromatography A* 729:237–242 (1996).

Geierstanger et al., "Design of a G·C—Specific DNA Minor Groove–Binding Peptide," *Science* 266:646–650 (1994).

Geierstanger et al., "Extending the recognition site of designed minor groove binding molecules," *Nature Structural Biology* 3:321–324 (1996).

Geierstanger et al., "Structural and Dynamic Characterization of the Heterodimeric and Homodimeric Complexes of Distamycin and 1–Methylimidazole–2–carboxamide–Netropsin Bound to the Minor Groove of DNA," *Biochemistry* 33:3055–3062 (1994).

Geierstanger, Bernhard Hubert, , PhD Thesis entitled *NMR Studies of Peptides, Distamycin and its Analogs Bound to the Minor Groove of DNA*, University of California, Berkeley (1994).

Genelabs, PCR Newswire—"Genelabs Receives Seven Patent Allowances for Its DNA–Binding Technology" (1987—exact date unknown).

Germann et al., "Relative Stability of Parallel– and Antiparallel–Stranded Duplex DNA," *Biochemistry* 27:8302–8306 (1988).

Giuliani et al., "Distamycin A derivatives: in vitro and in vivo activity of a new class of antitumor agents," *Proceedings of AACR* 29:330 at abstract No. 1311 (1988).

Goodsell et al., "Structure of dicationic monoimidazole lexitropsin bound to DNA," *Biochemistry* 34(51):16654–16661 (1995).

Greenberg et al., "Energetics of Formation of Sixteen Triple Helical Complexes Which Vary at a Single Position within a Purine Motif," *J. Am. Chem. Soc.* 117:5016–5022 (1995).

Grehn et al. "Synthesis and Antiviral Activity of Distamycin A Analogues: Substitutions on the Different Pyrrole Nitrogens and in the Amidine Function," *J. Med. Chem.* 26:1042–1049 (1983).

Grehn et al., "A convenient method for the preparation of 1% Tert–butyloxycarbonyl <Pyrroles," Angewandte Chemie International Edition in English v23(4)296 (1984).

Grehn et al., "Novel efficient total synthesis of antiviral antibiotic distamycin A," *Journal of Organic Chemistry* 46:3492–3497 (1981).

Grehn et al., "Removal of formyl, acetyl, and benzoyl groups from amides with conversion into the corresponding tert–butyl carbamates," Journal of the Chemical Society Chemical Communications 19(2):1317–1318 (1985).

Grehn et al., "Structure–activity–relationships in distamycin–A analogs–effect of alkyl groups on the pyrrole nitrogen at the non–amidine end of the molecule combined with methylelimination in the following ring," Acta Chemica Scandivavica 40(2):145–151 (1986).

Grehn et al., "The preparation and properties of partially protected 4–amino–1–methylimidazole–2–carboxylic acids to be used as intermediates in the synthesis of analogs of dystamycin–A," *Acta Chemica Scandivavica* 44(1):67–74 (1990).

Griffin and Dervan, "Recognition of Thymine·Adenine Base Pairs by Guanine in a Pyrimidine Triple Helix Motif," *Science* 245:967–971 (1989).

Griffin and Dervan, "Sequence–Specific Chiral Recognition of Right–Handed Double–Helical DNA by (2S,3S)– and (2R,3R)–Dihydroxybis(netropsin)succinamide," *J. Am. Soc. Chem.* 108:5008–5009 (1986).

Griffin, John Hampton, PhD Thesis entitled *Sturcture–, Stereochemistry–, and Metal–Regulated DNA Binding/Cleaving Molecules*, California Institute of Technology, Pasadena, California (Submitted Jul. 11, 1989).

Grygon and Spiro, "Ultraviolet Resonance Raman Spectroscopy of Distamycin Complexes with Poly(dA)–(dT) and Poly(dA–dT): Role of H–Bonding," *Biochemistry* 28:4397–4402 (1989).

Guo et al., "DNA sequence–selective binding of head–to–tail linked bis–lexitropsins: relation of phasing to cytotoxic potency," *Anti–Cancer Drug Des.* 8(5):369–397 (1993).

Gupta et al., "Design, synthesis and topoisomerase II inhibition activity of 4'–demethylepipodo–phyllotoxin– lexitropsin conjugates," *Anti–Cancer Drug Design* 11:325–338 (1996).

Gupta et al., "Novel DNA–directed alkylating agents consisting of naphthalimide, nitrogen mustard and lexitropsin moieties: synthesis, DNA sequence specificity and biological evaluation," *Anti–Cancer Drug Des.* 11:581–596 (1996).

Gupta et al., "Hybrid molecules containing propargylic sulfones and DNA minor groove–binding lexitropsins: Synthesis, sequences specificity of reaction with DNA and biological evaluation," *Gene* 149(1):81–90 (1994).

Hacia et al., "Inhibition of Klenow Fragment DNA Polymerase on Double–Helical Templates by Oligonucleotide–Directed Triple–Helix Formation," *Biochemistry* 33:6192–6200 (1994).

Hacia et al., "Phosphorothioate Oligonucleotide–Directed Triple Helix Formation," *Biochemistry* 33:5367–5369 (1994).

Han and Dervan, "Different conformational families of pyrimidine·purine·pyrimidine triple helices depending on backbone composition," *Nucleic Acids Research* 22:2837–2844 (1994).

Han and Dervan, "Sequence–specific recognition of double helical RNA and RNA·DNA by triple helix formation," *Proc. Natl. Acad. Sci. USA* 90:3806–3810 (1993).

Han and Dervan, "Visulation of RNA tertiary structure by RNA–EDTA·Fe(II) autocleavage: Analysis of tRNA$^{Phe}$ with uridine–EDTA·Fe(II) at position 47," *Proc. Natl. Acad. Sci. USA* 91:4955–4959 (1994).

Han et al., "Mapping RNA Regions in Eukaryotic Ribosomes That Are Accessible to Methidiumpropyl–EDTA·Fe(II) and EDTA·Fe(II)," *Biochemistry* 33:9831–9844 (1994).

Harapanhalli et al., [$^{125}$I/$^{127}$I]IodoHoechst 33342: Synthesis, DNA Binding, and Biodistribution, *J. Med. Chem.* 39:4804–4809 (1996).

Harshman and Dervan, "Molecular recognition of B–DNA by Hoechst 33258," *Nucleic Acids Research* 13:4825–4835 (1985).

Hertzberg and Dervan, "Cleavage of DNA with Methidiumpropyl–EDTA–Iron(II): Reaction Conditions and Product Analyses," *Biochemistry* 23:3934–3945 (1984).

Hinsberg et al., "Direct Studies of 1,1–Diazenes. Synthesis, Infrared and Electronic Spectra, and Kinetics of the Thermal Decomposition of N–(2,2,6,6–Tetramethylpiperidyl)nitrene and N–(2,2,5,5,–Tetramethylpyrrolidyl)nitrene," *J. Amer. Chem. Soc.* 104:766–773 (1982).

Huang et al., "Synthesis of designed functional models of bleomycin incorporating imidazole– containing lexitropsins as novel DNA recognition sites," *Heterocycles* 41(6):1181–1196 (1995).

Huang et al., "Design, synthesis, and sequence selective DNA cleavage of functional models of bleomycin. 1. Hybrids incorporating a sample metal–complexing moiety of bleomycine and lexitropsin carriers," *Bioconjugate Chem.* 6(1):21–33 (1995).

Huang et al., "Design of DNA–cleaving molecules which incorporate a simplified metal–complexing moiety of bleomycin and lexitropsin carriers," *Bioorg. Med. Chem. Lett.* 3(8):1751–1756 (1993).

Huntingon's Disease Collaborative Research Group, "A Novel Gene Containing a Trinucleotide Repeat That is Expanded and Unstable on Huntington's Disease Chromosomes," *Cell* 72:971–983 (1993).

Hunziker et al., "Design of an N$^7$–Glycosylated Purine Nucleoside for Recognition of GC Base Pairs by Triple Helix Formation," *J. Am. Chem. Soc.* 117:2661–2662 (1995).

Ikeda and Dervan, "Sequence–Selective Inhibition of Restriction Endonucleases by the Polyintercalator Bis(methidium)spermine," *J. Am. Chem. Soc.* 104:296–297 (1982).

Iverson and Dervan, "Adenine–Specific DNA Chemical Sequencing Reaction," *Methods in Enzymology* 218:222–227 (1993).

Iverson and Dervan, "Piperdine specific DNA chemical sequencing reaction," *Nucleic Acids Research* 14:7823–7830 (1987).

Jensen and Lysek, "Differences in the mycelial growth rhythms in a population of *Sclerotinia fructigena* (Pers.) Schroter," *Experientia* 39:1401–1402 (1983).

Jotterand–Bellomo, "The effects of distamycin A on cultured amniotic fluid cells," *Ann. Genet.* 26:27–30 (1983) (In French With English Abstract).

Kharatishvili et al., "Formation of the Left Helix On Simultaneous Exposure to Poly [d(GC)]bis–Netropsin and Zn(II) Ions," *Biophysics* 30:764–766 (1985).

Kiessling et al., "Flanking Sequence Effects within the Pyrimidine Triple–Helix Motif Characterized by Affinity Cleaving," *Biochemistry* 31:2829–2834 (1992).

Koh and Dervan, "Design of a Nonnatural Deoxyribonucleoside for Recognition of GC Base Pairs by Oligonucleotice–Directed Triple Helix Formation," *J. Am. Chem. Soc.* 114:1470–1478 (1992).

Koppel et al., "Basicity of 3– Aminopropionamidine Derivatives in Water and Dimethyl Sulphoxide, Implication for a Pivotal Step in the Synthesis of Distamycin A Analogues," *Journal of Physical Organic Chemistry* 9:265–268 (1996).

Koshlap et al., "Nonnatural Deoxyribonucleoside D$_3$ Incorporated in an Intramolecular DNA Triplex Binds Sequence–Specifically by Intercalation," *J. Am. Chem. Soc.* 115:7908–7909 (1993).

Kothekar et al., "Influence of Local Excitations in DNA Conformation on Binding of Nonintercalating Antitumor Antibiotic in the Minor groove," *International Journal of Quantum Chemistry: Quantum Biology Symposium* 13:175–183 (1986).

Krowicki and Lown, "Synthesis of Novel Imidazole–Containing DNA Minor Groove Binding Oligopeptides Related to the Antiviral Antibiotic Netropsin," *J. Org. Chem.* 52:3493–3501 (1987).

Kucerova et al., "Netropsin stimulates the formation of an extracellular proteinase and suppresses protein turnover in sporulating *Bacillus megaterium*," *FEMS Microbiology Letters* 34:21–26 (1986).

Kumar et al., "Molecular recognition and binding of a GC site–avoiding thiazole–lexitropsin to the decadeoxyribonucleotide d–[CGCAATTCGC]$_2$: An H–NMR evidence for thiazole intercalation," *J. Biomol. Struct. Dyn.* 8(1):99–121 (1990).

Kumar et al., "Structural and dynamic aspects of non–intercalative (1:1) binding of a thiazole–lexitropsin to the decadeoxyribonucleotide d–[CGCAATTCGC]$_2$: An H–NMR and molecular modeling study," *J. Biomol. Struct. Dyn.* 9(1):1–21 (1991).

Kuroda et al., "Intelligent compounds which read DNA base sequences," *Supramolecular Chemistry* 6:95–102 (1995).

Kurreck et al., "ENDOR spectroscopy– A promising technique for investigating the structure of organic radicals," *Angew. Chem. Int. Ed. Engl.* 23:173–194 (1984).

Lane et al., "Sequence specificity of actinomycin D and Netropsin binding to pBR322 DNA analyzed by protection from Dnase I," *Proc. Natl. Acad. Sci. USA* 80:3260–3264 (1983).

Larsen and Dickerson, "As the Helix Turns, or, Rational Design of Sequence Specific DNA Minor Groove Binding Drugs," *J. Mol. Graphics* 6:211 (1988).

Lazzari et al., EPO Patent Application No. 0 246 868 A1 published Nov. 25, 1987 for "Site Specific Alkylating Agents".

Lee and Walker, "Ch. 3—Sequence–Selective Binding of DNA by Oligopeptides as a Novel Approach to Drug Design," in *Polymeric Drugs and Drug Administration*, American Chemical Society, pp. 29–46 (1994).

Lee et al., "Structural and Dynamic Aspects of the Sequence Specific Binding of Netropsin and its Bis–Imidazole Analogue on the Decadeoxyribonucleotide d–[CGCAATTGCG]$_2$," *Journal of Biomolecular Structure & Dynanmics* 5:939–949 (1988).

Lee et al., "Sequence specific molecular recognition and binding of a monocationic bis–imidazole lexitropsin to the decadeoxyribonucleotide d–[(GATCCGTATG) (CATACGGATC)]: structural and dynamic aspects of intermolecular exchange studied by H–NMR," *J. Biomol. Struct. Dyn.* 5(5):1059–1087 (1988).

Lee et al., "Molecular recognition between oligopeptides and nucleic acids. Specificity of binding of a monocationic bis–furan lexitropsin to DNA deduced from footprinting and H NMR studies," *J. Mol. Recognit.* 2(2):84–93 (1989).

Leinsoo et al., "Attachment of Trivaline to a Netropsin Analog Changes the Specificity of its Binding to DNA," *Institute of Molecular Biology*, Academy of Sciences of USSR, pp. 134–148 (1988) translated from *Molekulyarnaya Biologiya* 22(1):159–175 (1988).

Levina et al., "Conjugates of Minor Groove DNA Binders with Oligodeoxynucleotides: Synthesis and Properties," *Antisense & Nucleic Acid Drug Development* 6:75–85 (1996).

Liquier et al., "FTIR Study of Netropsin Binding to Poly d(A–T) and Poly dA · Poly dT," *J. Biomolecular Structure & Dynamics* 7:119–126 (1989).

Lombardi and Crisanti, "Antimalarial Activity of Synthetic Analogues of Distamycin," *Pharmacol. Ther.* 76:125–133 (1977).

Lown and Krowicki, "Efficient Total Syntheses of the Oligopeptide Antibiotics Netropsin and Distamaycin," *J. Org. Chem.* 50:3774–3779 (1985).

Lown et al., "Molecular Recognition between Oligopeptides and Nucleic Acids: Novel Imidazole–Containing Oligopeptides Related to Netropsin That Exhibit Altered DNA Sequence Specificity," *Biochemistry* 25:7408–7416 (1986).

Lown et al., "Novel Linked Antiviral and Antitumor Agents Related to Netropsin and Distamycin: Synthesis and Biological Evaluation," *J. Med. Chem.* 32:2368–2375 (1989).

Lown et al., "Structure–Activity Relationship of Novel Oligopeptide Antiviral and Antitumor Agents Related to Netropsin and Distamycin," *J. Med. Chem.* 29:1210–1214 (1986).

Lown, "Design and Development of Sequence Selective Lexitropsin DNA Minor Groove Binders," *Crug Development Research* 34:145–183 (1995).

Lown, "Lexitropsins in antiviral drug development," *Antiviral Res.* 17(3):179–196 (1992).

Lown, "DNA recognition by lexitropsins, minor groove binding agents," *J. Mol. Recognit.* 7(2):79–88 (1994).

Lown, "Design of sequence–specific agents: Lexitropsins," *Mol. Aspects Anticancer Drug–DNA Interact* Ch. 11:322–355 (1993).

Lown, "Synthetic chemistry of naturally occurring oligopeptide antibiotics and related lexitropsins," *Org. Prep. Proced. Int.* 21(1):1–46 (1989).

Lu–D et al., "Synthesis and antiviral activity of 3 pyrazole analogs of distamycin–A," *Acta Chemica Scandivavica* v48(6):498–505 (1994).

Luebke and Dervan, "Nonenzymatic Ligation of Oligodeoxyribonucleotides on a Duplex DNA Template by Triple–Helix Formation," *J. Am. Chem. Soc.* 111:8733–8735 (1989).

Lythgoe and Ramsden, "4–Unsubstituted, 5–Amino and 5–Unsubstituted, 4–Aminoimidazoles," *Advances in Heterocyclic Chemistry* 61:1–58 (1994).

Mack and Dervan, "Sequence–Specific Oxidative Cleavage of DNA by a Designed Metalloprotein, Ni(II)·GGH(Hin139–190)$_1$," *Biochemistry* 31:9399–9405 (1992).

Maher et al., "Analysis of Promoter–Specific Repression by Triple–Helical DNA Complexes in a Eukaryotic Cell–Free Transcription System," *Biochemistry* 31:70–81 (1992).

Maher et al., "Inhibition of DNA Binding Proteins by Oligonucleotide–Directed Triple Helix Formation," *Science* 245:725–730 (1989).

Marck et al., "Specific interaction of netropsin, distamycin–3 and analogs with I.C duplexes: reversion towards the B form of the 2–deoxy–, 2'–deoxy–2'–fluoro– hybrid duplexes upon specific interactions with netropsin, distamycin–3 and analogs," *Nucleic Acids Research* 10:6147–6161 (1982).

Marky et al., "Calorimetric and spectroscopic investigation of drug–DNA interactions. I. The binding of netropsin to poly d(AT)," *Nucleic Acids Research* 11:2857–2871 (1983).

Martello et al., "Specific Activation of Open Complex Formation at an *Escherichia coli* Promoter by Oligo(N–methylpyrrolecarboxamide)s: Effects of Peptide Length and Identification of DNA Target Sites," *Biochemistry* 28:4455–4461 (1989).

Matyasek et al., "Evidence for a sequence–directed conformation perodicity in the genomic highly repetitive DNA detectable with single–strand–specific chemical probe potassium permangante," *Chromosome Research* 4:340–349 (1996).

Mazurek et al., "The binding of prototype lexitropsins to the minor groove of DNA: Quantum chemical studies," *J. Biomol. Struct. Dyn.* 9(2)299–313 (1991).

Milton et al., "Total chemical synthesis of a D–enzyme: The enantiomers of HIV–1 protease show demonstration of reciprocal chiral substrate specificity," *Science* 256:1445–1448 (1992).

Mitchell and Dervan, "Interhelical DNA–DNA Cross–linking. Bis(monoazidomethidium) octaoxahexacosanediamine: A Probe of Packaged Nucleic Acid," *J. Am. Chem. Soc.* 104:4265–4266 (1982).

Mitchell and Dervan, "Interhelical DNA–DNA Cross–Linking. Bis(monoazidomethidium)octaoxahexacosanediamine: A Probe of Packaged Nucleic Acid," *J. Am. Chem. Soc.* 104:4265–4266 (1982).

Momose et al., "3–hydroxypyrroles. I. A general synthetic route to 4,5–unsubstituted alkyl 3–hydroxypyrrole–2–carboxylates," *Chemical Pharmacology Bulletin* 26:2224–2232 (1978).

Momose et al., "3–hydroxypyrroles. II. The reaction of 4,5–unsubstituted alkyl 3–hydroxypyrrole–2–carboxylates with some electrophiles," *Chemical Pharmacology Bulletin* 26:3521–3529 (1978).

Moser and Dervan, "Sequence–Specific Cleavage of Double Helical DNA by Triple Helix Formation," *Science* 238:645–650 (1987).

Mosher et al., "Synthesis of N–Methyl–2–trichloroacetylpyrrole—A Key Building Block in Peptides that Bind DNA: Micro–, Semimicro–, and Macro–Scale Organic Lab Experiments," *Journal of Chemical Education* 73:1036–1039 (1996).

Mrksich and Dervan, "Antiparallel Side–by–Side Heterodimer for Sequence–Specific Recognition in the Minor Groove of DNA by a Distamycin/1–Methylimidazole–2–carboxamide–netropsin Pair," *J. Am. Chem. Soc.* 115:2572–2576 (1993).

Mrksich and Dervan, "Design of a Covalent Peptide Heterodimer of Sequence–Specific Recognition in the Minor Groove of Double–Helix DNA," *J. Am. Chem. Soc.* 116:3663–3664 (1994).

Mrksich and Dervan, "Enhanced Sequence Specific Recognition in the Minor Groove of DNA by Covalent Peptide Dimers: Bis(pyridine–2–carboxamidonetropsin)($CH_2$)$_{3-6}$," *J. Am. Chem. Soc.* 115:9892–9899 (1993).

Mrksich and Dervan, "Recognition in the Minor Groove of DNA at 5'–(A,T)GCGC(A,T)–3' by a Four Ring Tripeptide Dimer. Reversal of the Specificity of the Natural Product Distamycin," *J. Am. Chem. Soc.* 117:3325–3332 (1995).

Mrksich et al., "Antiparallel side–by–side dimeric motif for sequence–specific recognition in the minor groove of DNA by the designed peptide 1–methylimidazole–2–carboxamide netropsin," *Proc. Natl. Acad. Sci. USA* 89:7586–7590 (1992).

Mrksich et al., "Hairpin Peptide Motif. A New Class of Oligopeptides for Sequence–Specific Recognition in the Minor Groove of Double–Helical DNA," *J. Am. Chem. Soc.* 116:7983–7988 (1994).

Mrksich et al., "Design of a covalent peptide heterodimer for sequence–specific recognition in the minor groove of double–helical DNA," *J. Am. Chem. Soc.* 116:3663–1664 (1994).

Mrksich et al., Abstracts of the American Chemical Society 206 Part 2:413 (1993).

Mrksich, Milan, phD Thesis entitled *Design of Peptides for Sequence–Specific Recognition of the Minor Groove of DNA*, California Instititute of Technology, Pasadena, California (submitted Mar. 8, 1994).

Nechipurenko et al., "Cooperative Interactions Between Analogs of Distamycin A, Adsorbed on DNA," *Institute of Molecular Biology*, Academy of Sciences of USSR, pp. 263–272 (1984) translated from *Molekulyarnaya Biologiya* 18(2):332–342 (1984).

Nikolaev et al., "Design of Sequence–Specific DNA Binding Ligands That Use a Two–Stranded Peptide Motif for DNA Sequence Recognition," *Journal of Biomolecular Structure & Dynamics* 14:31–47 (1996).

Nilsson et al., "Structure at restriction endonuclease Mbol cleavage sites protected by actinomycin D or distamycin A," *FEBS Letters* 145:360–364 (1982).

Nishiwaki et al., "Efficient Synthesis of Oligo–N–Methylpyrrolecarboxamides and Related Compounds," *Heterocycles* 27:1945–1952 (1988).

Oakley et al., "Synthesis of a Hybrid Protein Containing the Iron–Binding Ligand of Bleomycin and the DNA–Binding Domain of Hin," *Bioconjugate Chem.* 5:242–247 (1994).

Oakley et al., "Evidence that a major groove–binding peptide can simultaneously occupy a common site on DNA," *Biochemistry* 31:10969–10975 (1992).

Ochi et al., "New Heritable Fragile Site on Chromosome 8 Induced by Distamycin A," *Jpn. J. Cancer Res.* 79:145–147 (1988).

Parks et al., "Optimization of the Hairpin Polyamide Design for Recognition of the Minor Groove of DNA," *J. Am. Chem. Soc.* 118:6147–6152 (1996).

Parks et al., "Recognition of 5'–(A,T)GG(A,T)$_2$–3' Sequences in the Minor Groove of DNA by Hairpin Polyamides," *J. Am. Chem. Soc.* 118:6153–6159 (1996).

Parrack et al., "Interaction of synthetic analogs of distamycin with DNA: Role of the conjugated N–methylpyrrole system in spcificity of binding," *FEBS Letters* 212:297–301 (1987).

Portugal and Waring, "Comparison of binding sites in DNA for berenil, netropsin and distamycin: A footprinting study," *Eur. J. Biochem.* 167:281–289 (1987).

Portugal and Waring, "Hydroxyl radical footprinting of the sequence–selective binding of netropsin and distamycin to DNA," *FEBS Letters* 225:195–200 (1987).

Portugal and Waring, "Interaction of nucleosome core particles with distamycin and echinomycin: analysis of the effect of DNA sequences," *Nucleic Acids Research* 15:885–903 (1987).

Povsic and Dervan, "Triple Helix Formation by Oligonucleotides on DNA Extended to the Physiological pH Range," *J. Am. Chem. Soc.* 111:3059–3061 (1989).

Priestley and Dervan, "Sequence Composition Effects on the Energetics of Triple Helix Formation by Oligonucleotides Containing a Designed Mimic of Protonated Cytosine," *J. Am. Chem. Soc.* 117:4761–4765 (1995).

Radhakrishnan and Patel, "NMR Structural Studies on a Nonnatural Deoxyribonucleoside Which Mediates Recognition of GC Base Pairs in Pyrimidine·Purine·Pyrimidine DNA Triplexes," *Biochemistry* 32:11228–11234 (1993).

Rajagopalan et al., "Interaction of non–intercalative drugs with DNA: Distamycin analogues," *J. Biosci.* 7:27–32(1985).

Rajagopalan et al., "Synthesis of a Distamycin Analogue: Tris(m–benzamido) Compound," *Indian Journal of Chemistry* 26B:1021–1024 (1987).

Rao et al., "Interaction of Synthetic Analogues of Distamycin and Netropsin with Nucleic Acids. Does Curvature of Ligand Play a Role in Distamycin–DNA Interactions?" *Biochemistry* 27:3018–3024 (1988).

Rao et al., "Molecular recognition between ligands and nucleic acids: Sequence preferences and binding of Pyrrolo [3,2–d] and [2,3–d]thiazole–containing lexitropsins deduced from MPE–Fe(II) footprinting," *Actual. Chim. Ther.* 20:159–188 (1993).

Rao et al., "Psoralen–lexitropsin hybrids: DNA sequence selectivity of photoinduced cross–linking from MPE footprinting and exonuclease III stop assay, and mode of binding from electric linear dichroism," *Anti–Cancer Drug Des.* 9(3):221–237 (1994).

Rao et al., "Molecular recognition between oligopeptides and nucleic acids: DNA binding selectivity of a series of 1,2,4–triazole–containing lexitropsins," *Chem. Res. Toxicol.* 4(2):241–252 (1991).

Rao et al., "Sequence–selective DNA binding by linked Bis–N–methylpyrrole dipeptides: an analysis by MPE footprinting and force field calculations," *J. Org. Chem.* 56(2):786–797 (1991).

Reinert et al., "Deformyldistamycin–DNA Interaction; DNA Conformational Changes as Revealed by Titration Rotational Viscometry," *J. Biomolecular Structure & Dynamics* 14(2):245–253 (1996).

Reinert et al., "DNA interaction of the imidazole–containing lexitropsin ImPy: Titration viscometric study in comparison to Netropsin," *J. Biomol. Struct. Dyn.* 12(4):847–855 (1995).

Ronne et al., "The effect of in vitro distamycin A exposure on metaphase chromosome structure," *Hereditas* 96:269–277 (1982).

Royyuru et al., "Theoretical Study of Conformational Flexibility of Distamycin–A Analog and its Binding to DNA," *Current Science* 56:581–584 (1987).

Rubin et al., "An unexpected major groove binding of netropsin and distamycin A to tRNA$^{phe}$," *Journal of Biomolecular Structure and Dynamics* 2:165–174 (1984).

Sakaguchi et al., "Effect of netropsin on plasmid DNA cleavage by BAL 31 nuclease," *FEBS Letters* 191:59–62 (1985).

Salmanova et al., "Interaction of DNA with Synthetic Ligands Containing N,4–Disubstituted Mono– and Diphthalimides," *Molecular Biology* 29:491–498 (1995).

Sanfilippo et al., "Activity of the Distamycin A on the Induction of Adaptive Enzymes in *Escherichia coli*," *J. gen. Microbiol.* 43:369–374 (1966).

Sarma et al., "Structure of Poly(dA)·Poly(dT) is not Identical to the AT Rich Regions of the Single Crystal Structure of CGCGAATT$^{Br}$CGCG. The Consequence of this to Netropsin Binding to Poly(dA)·Poly(dT)," *J. Biomolecular Structure & Dynamics* 3(3):433–436 (1985).

Schabel et al., "Observations on Antiviral Activity of Netropsin," *Proceedings of the Society for Experimental Biology and Medicine* 83:1–3 (1953).

Schmid et al., "Characterization of a Y/15 translocation by banding methods, distamycin A treatment of lymphocytes and DNA restriction endonuclease analysis," *Clinical Genetics* 24:234–239 (1983).

Schmid et al., "The use of distamycin A in human lymphocyte cultures," *Human Genet* 65:377–384 (1984).

Schuhmann et al., "Wirkung von Distamycin A und Netropsin auf normale und zellwandlose Zellen von *Escherichia coli* W 1655F$^+$," *Zeitschrift fur Allg. Mikrobiologie* 14:321–327 (1974) (In German With English Abstract).

Schultz and Dervan, "Distamycin and Penta–N–Methylpyrrolecarboxamide Binding Sites on Native DNA—A Comparison of Methidiumpropyl–EDTA–Fe(II) Footprinting and DNA Affinity Cleaving," *J. Biomolecular Structure & Dynamics* 1:1133–1147(1984).

Schultz and Dervan, "Sequence–specific double–strand cleavage of DNA by penta–N–methylpyrrolecarboxamide–EDTA·Fe(II)," *Proc. Natl. Acad. Sci. USA* 80:6834–6837 (1983).

Schulz and Dervan, "Sequence–Specific Double–Strand Cleavage of DNA by Bis(EDTA–distamycin-Fe$^1$) and EDTA–Bis(distamycin)·Fe$^{11}$," *J. Am. Chem. Soc.* 105:7748–7750 (1983).

Sengupta et al., "A Microgonotropen Pentaaza Pentabutylamine and its Interactions with DNA," *Bioorganic & Medicinal Chemistry* 4:803–813 (1996).

Shabtai et al., "Familial fragile site found at the cancer breakpoint (1)(q32): Inducibility by distamycin A, concomitance with gragile (16)(q22)," *Hum Genet* 73:232–234 (1986).

Shabtai et al., "Familial Fragility on Chromosome 16 (Fra 16q22) Enhanced by Both Interferon and Distamycin A," *Hum Genet* 63:341–344 (1983).

Shishido et al., "Enhancement of S1 Nuclease–Susceptibility of Negatively Superhelical DNA by Netropsin," *Biochemical & Biophysical Research Communications* 124:388–392 (1984).

Sidorova et al., "Competition between Netropsin and Restriction Nuclease EcoRI for DNA binding," *J. Biomolecular Structure & Dynamics* 13(2):367–385 (1995).

Singh et al., "Isohelicity and Strand Selectivity in the Minor Groove Binding of Chiral (1R,2R)– and (1S,2S)–Bis(netropsin)–1,2–cyclopropanedicarboxamide Ligands to Duplex DNA," *J. Am. Chem. Soc.* 116:7006–7020 (1994).

Singh et al., "Structural characterization of side–by side binding for a cross–linked lexitropsin dimer designed to target G–C base pairs in the DNA minor groove," *Magn. Reson. Chem.* 34:S55–S66 (1996).

Singh et al., "A H–NMR study of the DNA binding characteristics of thioformyldistamycin an amide isosteric lexitropsin," *Biochemistry* 31(28):6453–6461 (1992).

Singleton and Dervan, "Equilibrium Association Constants for Oligonucleotide–Directed Triple Helix Formation at Single DNA Sites: Linkage to Cation Valence and Concentration," *Biochemistry* 32:13171–13179 (1993).

Singleton and Dervan, "Influence of ph on the Equilibrium Association Constants for Oligodeoxyribonucleotide–Directed Triple Helix Formation at Single DNA Sites," *Biochemistry* 31:10995–11003 (1992).

Singleton and Dervan, "Temperature Dependence of the Energetics of Oligonucleotide–Directed Triple–Helix Formation at a Single DNA Site," *J. Am. Chem. Soc.* 116:10376–10382 (1994).

Skamrov et al., "Specific Protection of DNA from the Action of Dnase I by Distamycin A, Netropsin, and Bis–Netropsins," *Institute of Molecular Biology*, Academy of Sciences of USSR, pp. 153–167 (1985) translated from *Molekulyarnaya Biologiya* 19(1):177–195 (1985).

Sluka et al., "Synthesis of a Sequence–Specific DNA–Cleaving Peptide," *Science* 238:1129–1132 (1987).

Snounou and Malcolm, "Production of Positively Supercoiled DNA by Netropsin," *J. Mol. Biol.* 167:211–216 (1983).

Sponar and Votavova, "Selective Binding of Synthetic Polypeptides to DNA of Varying Composition and Sequence: Effect of Minor Groove Binding Drugs," *J. Biomolecular Structure & Dynamics* 13(6):979–987 (1996).

Stanchev et al., "Netropsin, Distamycin A, bis–Netropsins as Selective Inhibitors of the Effect of Restrictase and DNase I," *Institute of Molecular Biology*, Academy of Sciences of USSR, pp. 1324–1333 (1987) translated from *Molekulyarnaya Biologiya* 20(6):1614–1624 (1986).

Staubli and Dervan, "Sequence specificity of the non–natural pyrido[2,3–d]pyrimidine nucleoside in triple helix formation," *Nucleic Acids Research* 22:2637–2642 (1994).

Stilz and Dervan, "Specific Recognition of CG Base Pairs by 2–Deoxynebularine within the Purine·Purine·Pyrimidine Triple–Helix Motif," *Biochemistry* 32:2177–2185 (1993).

Strobel and Dervan, "Cooperative Site Specific Binding of Oligonucleotides to Duplex DNA," *J. Am. Chem. Soc.* 111:7286–7287 (1989).

Strobel and Dervan, "Triple Helix–Mediated Single–Site Enzymatic Cleavage of Megabase Genomic DNA," *Methods in Enzymology* 216:309–321 (1992).

Surovaya et al., "Construction of Peptide β–Hairpins Recognizing DNA Sequences," *Molecular Biology* 30:818–825 (1996).

Swalley et al., "Recognition of a 5'–(A,T)GGG(A,T)$_2$–3' Sequence in the Minor Groove of DNA by an Eight–Ring Hairpin Polyamide" *J. Am. Chem. Soc.* 118:8198–8206 (1996).

Takahashi et al., "82. Distamycin A–Induced Fragility on Chromosome 16, Fra(16)(q22), in a Japanese Population," *Proc. Japan Acad.* 61(B):299–302 (1985).

Takahashi et al., "A new rare distamycin A–inducible fragile site, fra(11)(p15.1), found in two acute nonlymphocytic leukemia (ANLL) patients with t(7;11)(p15–p13;p15)," *Hum Genet* 80:124–126 (1988).

Taylor et al., "DNA Affinity Cleaving—Sequence Specific Cleavage of DNA by Distamycin–EDTA·Fe(II) and EDTA–Distamycin·Fe(II)," *Tetrahedron* 40:457–465 (1984).

Tenette et al., "Force field development and conformational search strategy in the simulation of biomolcular recognition processes," *Biochemical Society Transactions* 24:268–274 (1996).

Tor and Dervan, "Site–Specific Enzymatic Incorporation of an Unnatural Base, $N^6$–(6–Aminohexyl)isoguanosine, into RNA," *J. Am. Chem. Soc.* 115:4461–4467 (1993).

Trauger et al., "Recognition of DNA by designed ligands at subnanomolar concentrations," *Nature* 382:559–561 (1996).

Turner et al., "The mutagenic properties of DNA minor–groove binding ligands," *Mutation Research* 355:141–169 (1996).

Uchida et al., "High resolution footprinting of EcoRI and distamycin with $Rh(phi)_2(bpy)^{3+}$, a new photofootprinting reagent," *Nucleic Acids Research* 17:10259–10279 (1989).

Van Dyke and Dervan, "Chromoycin, Mithramycin, and Olivomycin Binding Sites on Heterogeneous Deoxyribonucleic Acid. Footprinting with (Methidiumpropyl–EDTA) iron (II)," *Biochemistry* 22:2373–2377 (1983).

Van Dyke and Dervan, "Echinomycin Binding Sites on DNA," *Science* 225:1122–1127 (1984).

Van Dyke and Dervan, "Methidiumpropyl–EDTA·Fe(II) and DNase I footprinting report different small molecule binding site sizes on DNA," *Nucleic Acids Research* 11:5555–5567 (1983).

Van Dyke et al., "Map of distamycin, netropsin, and actinomycin binding sites on heterogeneous DNA: DNA cleavage–inhibition patterns with methidiumpropyl–EDTA·Fe(II)," *Proc. Natl. Acad. Sci. USA* 79:5470–5474 (1982).

Vigneswaran et al., "Influence of GC and AT Specific DNA Minor Groove Binding Drugs on Intermolecular Triplex Formation in the Human c–Ki–ras Promoter," *Biochemistry* 35:1106–1114 (1996).

Wade and Dervan, "Alteration of the Sequence Specificity of Distamycin on DNA by Replacement of an N–Methylpyrrolecarboxamide with Pyridine–2–carboxamide," *J. Am. Chem. Soc.* 109:1574–1575 (1987).

Wade et al., "Binding Affinities of Synthetic Peptides, Pyridine–2–carboxamidonetropsin and 1–Methylimidazole–2–carboxamidonetropsin, That Form 2:1 Complexes in the Minor Groove of Double–Helical DNA," *Biochemistry* 32:11385–11389 (1993).

Wade et al., "Design of Peptides That Bind in the Minor Groove of DNA at 5'–(A,T)G(A,T)C(A,T)–3' Sequences by a Dimeric Side–by–Side Motif," *J. Am. Chem. Soc.* 114:8783–8794 (1992).

Wang et al., "Interactions Between a Symmetrical Minor Groove Binding Compound and DNA Oligonucleotides: $^1H$ and $^{19}F$ NMR Studies," *J. Biomolecular Structure & Dynamics* 7:101–117 (1989).

Wang et al., "Design, synthesis, cytotoxic properties and preliminary DNA sequencing evaluation of CPI–N–methylpyrrole hybrids. Enhancing effect of a trans double bond linker and role of the terminal amide functionality on cytotoxic potency," *Anti–Cancer Drug Des.* 11(1):15–34 (1996).

Wang et al., "Anti HIV–I activity of linked lexitropsins," *J. Med. Chem.* 35(15):2890–2897 (1992).

Wang et al., "Convenient synthesis of pyrroloiminoquinone and its lexitropsin–linked derivative," *Tetrahedron Lett.* 35(24):4085–4086 (1994).

Ward et al., "Determination of Netropsin–DNA Binding Constants from Footprinting Data," *Biochemistry* 27:1198–1205 (1988).

Ward et al., "Quantitative Footprinting Analysis of the Netropsin–DNA Interaction," *J. Biomolecular Structure & Dynamics* 4(5):685–695 (1987).

Wemmer et al., Abstracts of the American Chemical Society 208 Part 2:9 (1994).

Wiederholt et al., "DNA–Tethered Hoechst Groove–Binding Agents: Duplex Stabilization and Fluorescence Characteristics," *J. Amer. Chem. Soc.* 118:7055–7062 (1996).

Wilkins, "Selective binding of actinomycin D and distamycin A to DNA," *Nucleic Acids Research* 10:7273–7282 (1982).

Williamson et al., "Phase–Sensitive Heteronuclear Multiple– Bond Correlation in the Presence of Modest Homonuclear Coupling. Application to Distamycin A," *Journal of Magnetic Resonance* 82:605–612 (1989).

Wong and Bateman, "TBP–DNA interactions in the minor groove discriminate between A:T and T:A base pairs," *Nucleic Acids Research* 22:1890–51896 (1994).

Woynarowski et al., "DNA Minor–Groove Binding Agents Interfere with Topoisomerase II–Mediated Effects of VM–26 and m–AMSA," *Proceedings of AACR* 29:274 at abstract No. 1089 (1988).

Xie et al., "Synthesis and DNA cleaving properties of hybrid molecules containing propargylic sulfones and minor groove binding lexitropsins," *Bioorg. Med. Chem. Lett.* 3(8):1565–1570 (1993).

Yamamoto et al., "Synthesis and DNA Binding Properties of Amide Bond–Modified Analogues Related to Distamycin," *Tetrahedron Letters* 37:7801–7804 (1996).

Yang et al., "Studies on Cooperative Binding of an Extended Distamycin A Analogue in the Minor Groove of DNA by NMR Spectroscopy," *Biochemical and Biophysical Research Communications* 222:764–769 (1996).

Youngquist and Dervan, "Sequence–specific recognition of B–DNA by oligo(N–methylpyrrolecarboxamid)s," *Proc. Natl. Acad. Sci. USA* 82:2565–2569 (1985).

Youngquist and Dervan, "Sequence–specific recognition of B–DNA by Bis(EDTA–distamycin)fumaramide," *J. Am. Chem. Soc.* 107:5528–5529 (1985).

Zakrzewska and Pullman, "Theoretical Study of the Sequence of Isolexins, Isohelical DNA Groove Binding Ligands. Proposal for the GC Minor Groove Specific Compounds," *Journal of Biomolecular Structure & Development* 5(5):1043–1058 (1988).

Zakrzewska et al., "Drug Recognition of DNA. Proposal for GC Minor Groove Specific Ligands: Vinylexins," *Journal of Biomolecular Structure & Development* 6(2):331–344 (1988).

Zasedatelev et al., "Mono–, di– and trimeric binding of a bis–netropsin to DNA," *FEBS Letters* 375:304–306 (1995).

Zimmer and Wahnert, "Nonintercalating DNA–Binding Ligands: Specificity of the Interaction and Their Use as Tools in Biophysical, Biochemical and Biological Investigations of the Genetic Material," *Prog. Biophys. molec. Biol.* 47:31–112 (1986).

Zimmer et al., "Binding of Analogues of the Antibiotics Distamycin A and Netropsin to Native DNA," *Eur. J. Biochem.* 26:81–89 (1972).

Zimmer et al., "Chain Length–Dependent Association of Distamycin–Type Oligopeptides with A·T and G·C Pairs in Polydeoxynucleotide Duplexes," *Biochimica et Biophysica Acta* 741:15–22 (1983).

Zimmer et al., "Differential stabilization by netropsin of inducible B–like conformations in deoxyribo–, ribo– and 2'–deoxy–2'–fluororibo–adenosine containing duplexes of $(dA)_n \cdot (dT)_n$ and $(dA)_n \cdot (dU)_n$," *Nucleic Acids Research* 10:1721–1732 (1982).

Zimmer et al., "Z–DNA and other non–B–DNA structures are reversed to B–DNA by interaction with netropsin," *FEBS Letters* 154:156–160 (1983).

\* cited by examiner

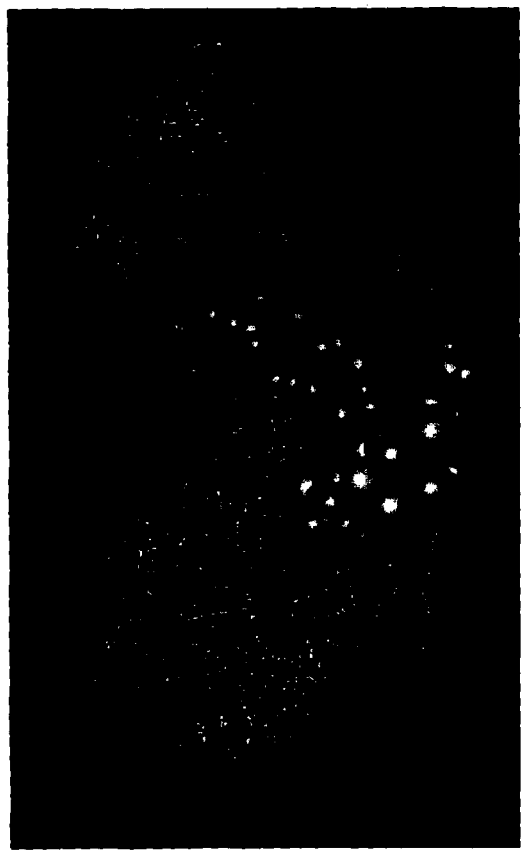 
FIG. 2A  FIG. 2B

ImPyPy-(R)$^{H2N}$γ-PyPyPy-β-Dp (1-R)

ImPyPy-(R)$^{H2N}$γ-PyPyPy-β-EtOH (2-R)

ImPyPy-(R)$^{AC}$γ-PyPyPy-β-Dp (3-R)

ImPyPy-(R)$^{H_2N}$γ-PyPyPy-β-Dp-EDTA·Fe(II)  (4-R·Fe(II))

ImPyPy-(R)$^{EDTA·Fe}$γ-PyPyPy-β-Dp  (5-R·Fe(II))

ImPyPy-(S)$^{H2N}$γ-PyPyPy-β-Dp

ImPyPy-(S)$^{AC}$γ-PyPyPy-β-Dp

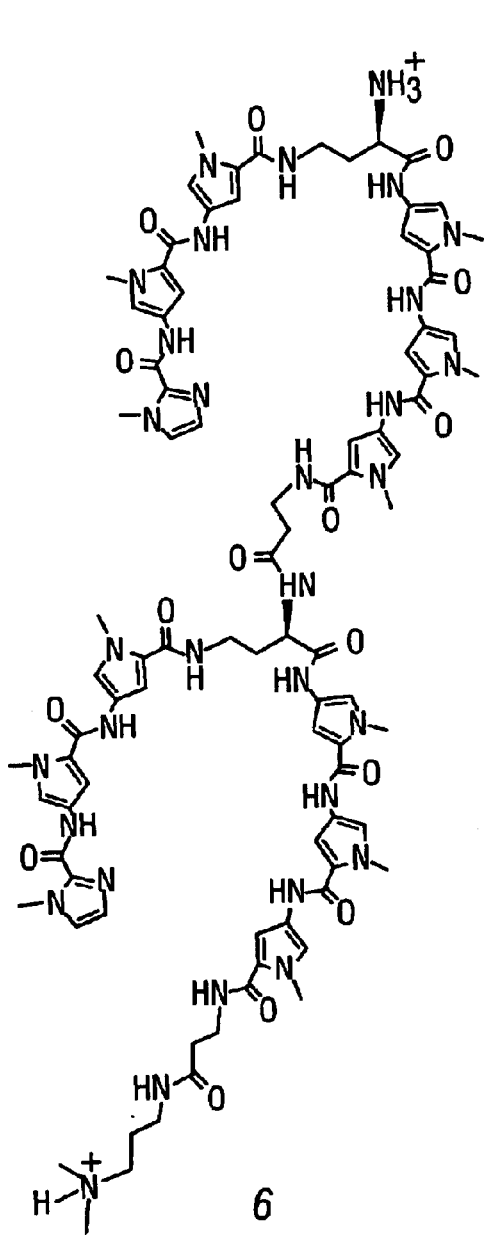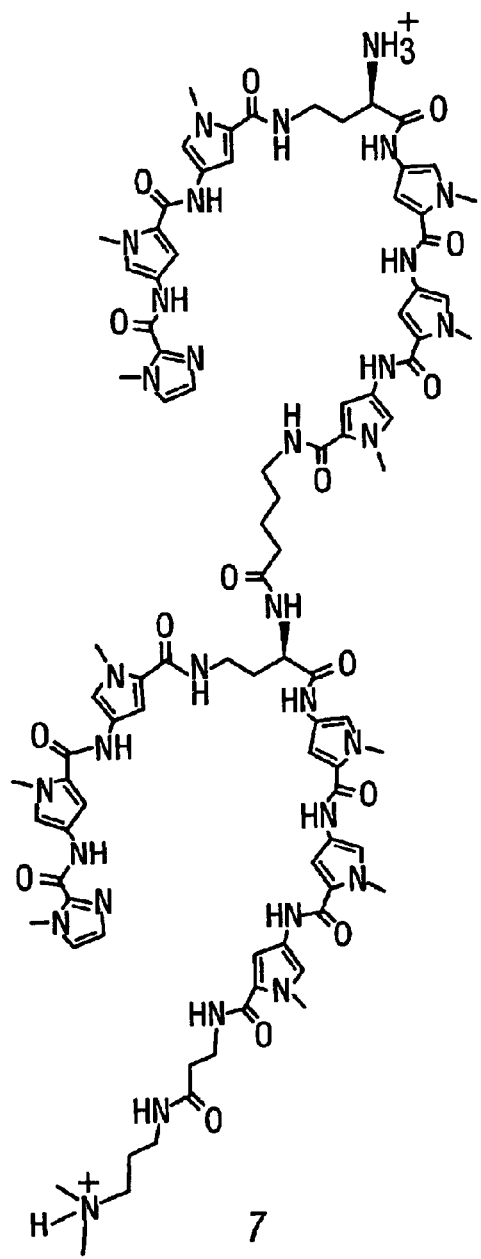
*FIG. 14A*      *FIG. 14B*

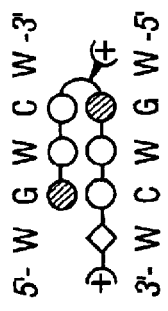
FIG. 17C
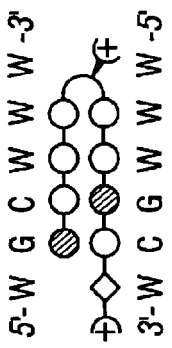
FIG. 17F
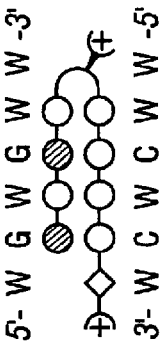
FIG. 17I
FIG. 17B
FIG. 17E
FIG. 17H
FIG. 17A
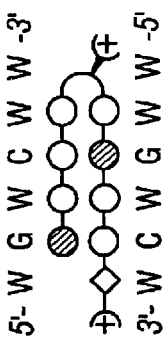
FIG. 17D
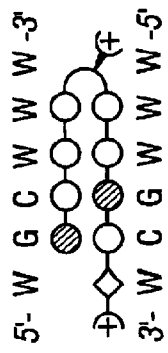
FIG. 17G

SEQUENCE LISTING

<160> NUMBER OF SEQ ID NOS: 36

<210> SEQ ID NO 1
<211> LENGTH: 11
<212> TYPE: DNA
<213> ORGANISM: Artificial Sequence
<220> FEATURE:
<223> OTHER INFORMATION: Polyamide Target

<400> SEQUENCE: 1
tgttattgtt a                                                          11

<210> SEQ ID NO 2
<211> LENGTH: 11
<212> TYPE: DNA
<213> ORGANISM: Artificial Sequence
<220> FEATURE:
<223> OTHER INFORMATION: Polyamide Target

<400> SEQUENCE: 2
tgtcattgtc a                                                          11

-continued

```
<210> SEQ ID NO 3
<211> LENGTH: 10
<212> TYPE: DNA
<213> ORGANISM: Artificial Sequence
<220> FEATURE:
<223> OTHER INFORMATION: Polyamide Target

<400> SEQUENCE: 3
tgttatgtta                                                                 10

<210> SEQ ID NO 4
<211> LENGTH: 22
<212> TYPE: DNA
<213> ORGANISM: Artificial Sequence
<220> FEATURE:
<223> OTHER INFORMATION: Polyamide Target

<400> SEQUENCE: 4
tgttatatgt tatgtcatgt ca                                                   22

<210> SEQ ID NO 5
<211> LENGTH: 12
<212> TYPE: DNA
<213> ORGANISM: Artificial Sequence
<220> FEATURE:
<223> OTHER INFORMATION: Polyamide Target

<400> SEQUENCE: 5
tgtcatatgt ca                                                              12

<210> SEQ ID NO 6
<211> LENGTH: 11
<212> TYPE: DNA
<213> ORGANISM: Artificial Sequence
<220> FEATURE:
<223> OTHER INFORMATION: Polyamide Target

<400> SEQUENCE: 6
taacaataac a                                                               11

<210> SEQ ID NO 7
<211> LENGTH: 11
<212> TYPE: DNA
<213> ORGANISM: Artificial Sequence
<220> FEATURE:
<223> OTHER INFORMATION: Polyamide Target

<400> SEQUENCE: 7
tgttatgtta g                                                               11

<210> SEQ ID NO 8
<211> LENGTH: 11
<212> TYPE: DNA
<213> ORGANISM: Artificial Sequence
<220> FEATURE:
<223> OTHER INFORMATION: Polyamide Target

<400> SEQUENCE: 8
ctaacataac a                                                               11

<210> SEQ ID NO 9
<211> LENGTH: 11
<212> TYPE: DNA
<213> ORGANISM: Artificial Sequence
<220> FEATURE:
```

-continued

<223> OTHER INFORMATION: Polyamide Target

<400> SEQUENCE: 9
tgttatatgt t                                                          11

<210> SEQ ID NO 10
<211> LENGTH: 11
<212> TYPE: DNA
<213> ORGANISM: Artificial Sequence
<220> FEATURE:
<223> OTHER INFORMATION: Polyamide Target

<400> SEQUENCE: 10
aacatataac a                                                          11

<210> SEQ ID NO 11
<211> LENGTH: 11
<212> TYPE: DNA
<213> ORGANISM: Artificial Sequence
<220> FEATURE:
<223> OTHER INFORMATION: Polyamide Target

<400> SEQUENCE: 11
tgacaatgac a                                                          11

<210> SEQ ID NO 12
<211> LENGTH: 11
<212> TYPE: DNA
<213> ORGANISM: Artificial Sequence
<220> FEATURE:
<223> OTHER INFORMATION: Polyamide Target

<400> SEQUENCE: 12
tgtcattgtc a                                                          11

<210> SEQ ID NO 13
<211> LENGTH: 11
<212> TYPE: DNA
<213> ORGANISM: Artificial Sequence
<220> FEATURE:
<223> OTHER INFORMATION: Polyamide Target

<400> SEQUENCE: 13
tgtttcctgt g                                                          11

<210> SEQ ID NO 14
<211> LENGTH: 11
<212> TYPE: DNA
<213> ORGANISM: Artificial Sequence
<220> FEATURE:
<223> OTHER INFORMATION: Polyamide Target

<400> SEQUENCE: 14
cacaggaaac a                                                          11

<210> SEQ ID NO 15
<211> LENGTH: 11
<212> TYPE: DNA
<213> ORGANISM: Artificial Sequence
<220> FEATURE:
<223> OTHER INFORMATION: Polyamide Target

<400> SEQUENCE: 15
tgattacgcc a                                                          11

```
<210> SEQ ID NO 16
<211> LENGTH: 11
<212> TYPE: DNA
<213> ORGANISM: Artificial Sequence
<220> FEATURE:
<223> OTHER INFORMATION: Polyamide Target

<400> SEQUENCE: 16
tggcgtaatc a                                                               11

<210> SEQ ID NO 17
<211> LENGTH: 10
<212> TYPE: DNA
<213> ORGANISM: Artificial Sequence
<220> FEATURE:
<223> OTHER INFORMATION: Polyamide Target

<400> SEQUENCE: 17
taacatgtca                                                                 10

<210> SEQ ID NO 18
<211> LENGTH: 10
<212> TYPE: DNA
<213> ORGANISM: Artificial Sequence
<220> FEATURE:
<223> OTHER INFORMATION: Polyamide Target

<400> SEQUENCE: 18
taacaaatgt                                                                 10

<210> SEQ ID NO 19
<211> LENGTH: 47
<212> TYPE: DNA
<213> ORGANISM: Artificial Sequence
<220> FEATURE:
<223> OTHER INFORMATION: Sequence containing Polyamide Target

<400> SEQUENCE: 19
ggatcctcta gagtcgacat gacattcgtc cacattgtta gaccacg                        47

<210> SEQ ID NO 20
<211> LENGTH: 47
<212> TYPE: DNA
<213> ORGANISM: Artificial Sequence
<220> FEATURE:
<223> OTHER INFORMATION: Sequence containing Polyamide Target

<400> SEQUENCE: 20
cgtggtctaa caatgtggac gaatgtcatg tcgactctag aggatcc                        47

<210> SEQ ID NO 21
<211> LENGTH: 19
<212> TYPE: DNA
<213> ORGANISM: Artificial Sequence
<220> FEATURE:
<223> OTHER INFORMATION: Polyamide Target

<400> SEQUENCE: 21
tccacattgt tagaccacg                                                       19

<210> SEQ ID NO 22
<211> LENGTH: 19
<212> TYPE: DNA
<213> ORGANISM: Artificial Sequence
<220> FEATURE:
<223> OTHER INFORMATION: Polyamide Target
```

```
<400> SEQUENCE: 22
cgtggtctaa caatgtgga                                              19

<210> SEQ ID NO 23
<211> LENGTH: 19
<212> TYPE: DNA
<213> ORGANISM: Artificial Sequence
<220> FEATURE:
<223> OTHER INFORMATION: Polyamide Target

<400> SEQUENCE: 23
cgacatgaca ttcgtccac                                              19

<210> SEQ ID NO 24
<211> LENGTH: 19
<212> TYPE: DNA
<213> ORGANISM: Artificial Sequence
<220> FEATURE:
<223> OTHER INFORMATION: Polyamide Target

<400> SEQUENCE: 24
gtcgacgaat gtcatgtcg                                              19

<210> SEQ ID NO 25
<211> LENGTH: 11
<212> TYPE: DNA
<213> ORGANISM: Artificial Sequence
<220> FEATURE:
<223> OTHER INFORMATION: Polyamide Target

<400> SEQUENCE: 25
tgttattgtt a                                                      11

<210> SEQ ID NO 26
<211> LENGTH: 11
<212> TYPE: DNA
<213> ORGANISM: Artificial Sequence
<220> FEATURE:
<223> OTHER INFORMATION: Polyamide Target

<400> SEQUENCE: 26
taacaataac a                                                      11

<210> SEQ ID NO 27
<211> LENGTH: 22
<212> TYPE: DNA
<213> ORGANISM: Artificial Sequence
<220> FEATURE:
<223> OTHER INFORMATION: Polyamide Target

<400> SEQUENCE: 27
tgacaatgac ataacaataa ca                                          22

<210> SEQ ID NO 28
<211> LENGTH: 22
<212> TYPE: DNA
<213> ORGANISM: Artificial Sequence
<220> FEATURE:
<223> OTHER INFORMATION: Polyamide Target

<400> SEQUENCE: 28
tgttattgtt atgtcattgt ca                                          22

<210> SEQ ID NO 29
<211> LENGTH: 11
```

```
<212> TYPE: DNA
<213> ORGANISM: Artificial Sequence
<220> FEATURE:
<223> OTHER INFORMATION: Polyamide Target

<400> SEQUENCE: 29 wwwwwggwc w                                                  11

<210> SEQ ID NO 30
<211> LENGTH: 11
<212> TYPE: DNA
<213> ORGANISM: Artificial Sequence
<220> FEATURE:
<223> OTHER INFORMATION: Polyamide Target

<400> SEQUENCE: 30
wgwccwwwww w                                                 11

<210> SEQ ID NO 31
<211> LENGTH: 64
<212> TYPE: DNA
<213> ORGANISM: Artificial Sequence
<220> FEATURE:
<223> OTHER INFORMATION: Sequence containing Polyamide Target

<400> SEQUENCE: 31
gatcgcgagg cctcattgtt atgttagcga ggcctcattg tcatgtcagc gaggcctcat    60
agct                                                               64

<210> SEQ ID NO 32
<211> LENGTH: 66
<212> TYPE: DNA
<213> ORGANISM: Sequence containing Polyamide Target
<220> FEATURE:
<223> OTHER INFORMATION: Polyamides bind to minor groove of DNA

<400> SEQUENCE: 32
gatcgcgagg cctcattgtt attgttagcg aggcctcatt gtcattgtca gcgaggcctc    60
atagct                                                             66

<210> SEQ ID NO 33
<211> LENGTH: 68
<212> TYPE: DNA
<213> ORGANISM: Artificial Sequence
<220> FEATURE:
<223> OTHER INFORMATION: Sequence containing Polyamide Target

<400> SEQUENCE: 33
gatcgcgagg cctcattgtt atatgttagc gaggcctcat tgtcatatgt cagcgaggcc    60
tcatagct                                                           68

<210> SEQ ID NO 34
<211> LENGTH: 64
<212> TYPE: DNA
<213> ORGANISM: Artificial Sequence
<220> FEATURE:
<223> OTHER INFORMATION: Sequence containing Polyamide Target

<400> SEQUENCE: 34
agctatgagg cctcgctgac atgacaatga ggcctcgcta acataacaat gaggcctcgc    60
gatc                                                               64

<210> SEQ ID NO 35
```

```
<211> LENGTH: 66
<212> TYPE: DNA
<213> ORGANISM: Artificial Sequence
<220> FEATURE:
<223> OTHER INFORMATION: Sequence containing Polyamide Target

<400> SEQUENCE: 35
agctatgagg cctcgctgac aatgacaatg aggcctcgct aacaataaca atgaggcctc    60
gcgatc                                                              66

<210> SEQ ID NO 36
<211> LENGTH: 68
<212> TYPE: DNA
<213> ORGANISM: Artificial Sequence
<220> FEATURE:
<223> OTHER INFORMATION: Sequence containing Polyamide Target

<400> SEQUENCE: 36
agctatgagg cctcgctgac atatgacaat gaggcctcgc taacatataa caatgaggcc    60
tcgcgatc                                                            68
```

US 7,049,061 B1

STEREOCHEMICAL CONTROL OF THE DNA BINDING AFFINITY, SEQUENCE SPECIFICITY, AND ORIENTATION-PREFERENCE OF CHIRAL HAIRPIN POLYAMIDES IN THE MINOR GROOVE

CROSS-REFERENCE TO RELATED APPLICATIONS

This application is a continuation in part of PCT/U98/03829, filed Jan. 29, 1998, and is a continuation-in-part of PCT/US97/03332, filed Feb. 20, 1997; thereafter filed as 371 U.S. application Ser. No. 08/837,524; filed Apr. 21, 1997; now U.S. Pat. No. 6,143,901; U.S. application Ser. No. 08/853,522, filed May 8, 1997; now U.S. Pat. No. 6,635,417; and PCT/US97/12722, filed Jul. 21, 1997; which are continuation-in-part applications of U.S. application Ser. No. 08/607,078, filed Feb. 26, 1996; now U.S. Pat. No. 6,090,947; and provisional application 60/042,022, filed Apr. 16, 1997, and provisional application 60/043,444, filed Apr. 8, 1997. The priority benefit is also claimed to provisional application 60/038,384, filed Feb. 14, 1997, and provisional application 60/023,309, filed Jul. 31, 1996, and provisional application 60/024,374, filed Aug. 1, 1996, and provisional application 60/026,713, filed Sep. 25, 1996. The specification of these applications are incorporated herein by reference.

The U.S. Government has certain rights to this invention persuant to Grant Nos. GM 26453, 27681, and 47530 awarded by the National Institute of Health.

BACKGROUND OF THE INVENTION

1. Field of the Invention

This invention relates to polyamides which bind to predetermined sites of the minor groove of double-stranded DNA.

2. Description of the Related Art

The art describes a large variety of polyamides which have three to six carboxamide base pairs and a hairpin loop derived from γ-aminobutyric acid and the ability to bind to the minor groove of DNA in the promoter region to inhibit gene expression. Thus, polyamides consisting of N-methylimidazole (Im), N-methylpyrrole (Py), and β-alanine and γ-amino butyric acid and methods for preparation of such polyamides are well known.

Polyamides containing N-methylpyrrole and N-methylimidazole amino acids are synthetic ligands that have an affinity and specificity for DNA comparable to naturally occurring DNA binding proteins (Trauger, et al. *Nature* 1996, 382, 559; Swalley, et al. *J. Am. Chem. Soc.* 1997, 119, 6953; Turner, et al. *J. Am. Chem. Soc.* 1997, 119, 7636). DNA recognition depends on side-by-side amino acid pairings oriented N-C with respect to the 5'-3' direction of the DNA helix in the minor groove (Wade, W. S., et al. *J. Am. Chem. Soc.* 1992, 114, 8783; Mrksich, et al. *Proc. Natl. Acad. Sci., USA* 1992, 89, 7586; Wade, et al. *Biochemistry* 1993, 32, 11385; Mrksich, et al. *J. Am. Chem. Soc.* 1993, 115, 2572; Geierstanger, et al. *Science* 1994, 266, 646; White, et al. *J. Am. Chem. Soc.* 1997, 119, 8756). Antiparallel pairing of imidazole (Im) opposite pyrrole (Py) recognizes a G•C base pair, while a Py/Im combination recognizes C•G.[2] A Py/Py pair is degenerate and recognizes either an A•T or T•A base pair (Wade, W. S., et al. *J. Am. Chem. Soc.* 1992, 114, 8783; Mrksich, et al. *Proc. Natl. Acad. Sci., USA* 1992, 89, 7586; Wade, et al. *Biochemistry* 1993, 32, 11385; Mrksich et al. *J. Am. Chem. Soc.* 1993, 115, 2572; Geierstanger, et al. *Science* 1994, 266, 646; White, et al. *J. Am. Chem. Soc.* 1997, 119, 8756; Pelton, et al. *Proc. Natl. Acad. Sci., USA* 1989, 86, 5723; Pelton, et al. *J. Am. Chem. Soc.* 1990, 112, 1393; White, et al. *Biochemistry* 1996, 35, 12532; Chen, et al. *J. Mol. Biol.* 1997, 267, 1157). An Im/Im pairing is disfavored, breaking a potential degeneracy for recognition (Singh, et al. *Proc. Natl. Acad. Sci. U.S.A.* 1994, 91, 7673; White, et al. *Chem. & Biol.* 1997, 4, 569).

Investigators have also attempted to prevent slipped-binding motifs as well as increase DNA-binding affinity and sequence specificity by covalent linkage of polyamide subunits (Trauger, et al. *J. Am. Chem. Soc.* 1996, 118, 6160; Geierstanger, et al. *Nature Struct. Biol.* 1996, 3, 321; Swalley, et al. *Chem. Eur. J.* 1997, 3, 1608; Wemmer, et al. *Curr. Opin. Struct. Biol.* 1997, 7, 355; Mrksich, et al. *J. Am. Chem. Soc.* 1994, 116, 3663; Dwyer, et al. *J. Am. Chem. Soc.* 1993, 115, 9900; Chen, et al. *J. Am. Chem. Soc.* 1994, 116, 6995). A hairpin polyamide motif with γ-aminobutyric acid (γ) has been utilized as a turn-specific internal-guide-residue and provides a synthetically accessible method for C-N linkage of polyamide subunits (FIG. 1). Head-to-tail linked polyamides bind specifically to designated target sites with 100-fold enhanced affinity relative to unlinked subunits (Mrksich, et al. *J. Am. Chem. Soc.* 1994, 116, 7983; Parks, et al. *J. Am. Chem. Soc.* 1996, 118, 6147; Parks, et al. *J. Am. Chem. Soc.* 1996, 118, 6153; Trauger, et al. *Chem. & Biol.* 1996, 3, 369; Swalley, et al. *J. Am. Chem. Soc.* 1996, 118, 8198; Pilch, et al. *Proc. Natl. Acad. Sci. U.S.A.* 1996, 93, 8306; de Claire, et al. *J. Am. Chem. Soc.* 1997, 119, 7909).

Eight-ring hairpin polyamides bearing a single positively charged tertiary amine group at the C-terminus have been shown to be cell-permeable and to inhibit the transcription of specific genes in cell culture (Gottesfeld, et al. *Nature* 1997, 387, 202). However, recent studies of polyamide size limitations suggest that beyond five rings, the ligand curvature fails to match the pitch of the DNA helix, disrupting the hydrogen bonds and van der Waals interactions responsible for specific polyamide-DNA complex formation (Kelley, et al. *Proc. Natl. Acad. Sci. USA*, 1996, 93:6981; Kielkopf, et al. *Nature Struc. Biol.*, in press). Recognition of seven base pairs by ten-ring hairpin polyamids containing five contiguous ring pairings represents the upper limit in binding site sizes targetable by the hairpin motif (Turner, et al. *J. am. Chem. Soc.*, 1997, 119:7636). Addition of pairings of β-alanine with β-alanine, pyrrole, or imidazole has allowed extention of the hairpin motif to 8-bp recognition, as demonstrated in provisional application 60/042,222. However, those skilled in the art have recognized the extreme difficulties associated with the design of hairpin motifs recognizing longer site sizes.

The present invention involves the use of R-2,4-diaminobutyric acid as a replacement for γ-aminobutyric acid to make the hairpin loop. In addition, a methodology for expanding the targetable binding site size of hairpins by covalently linking existing hairpin motifs without compromising DNA-binding and sequence specificity is provided.

SUMMARY OF THE INVENTION

This invention provides improved polyamides comprising a hairpin loop derived from γ-aminobutyric acid which bind to the minor groove of a promoter region of a DNA sequence. Binding of the polyamide to the DNA sequence of the promoter region inhibits expression of the requisite gene. The improvement relates to the use of R-2,4-diaminobutyric acid and derivatives of the 2-amino group to form the hairpin loop. The improved asymmetric hairpin provides for tighter binding of the polyamides to the minor groove of DNA and additionally provides an amine function for derivatizing polyamides by, for example, forming amide linkages. The improved asymmetric hairpin provides for the synthesis of tandemly-linked improved polyamides that allow for longer binding sites without compromising affinity or selectivity. The improved asymmetric hairpin may also serve to attach functional or detectable groups to the polyamide.

BRIEF DESCRIPTION OF THE FIGURES

FIGS. 2A and 2B. Computer generated models of: (A) ImPyPy-(R)$^{H_2N}$γ-PyPyPy-β-Dp and (B) ImPyPy-(S)$^{H_2N}$γ-PyPyPy-β-Dp bound in the minor groove of double stranded DNA van der Waals surface.

FIGS. 4A–4B. Solid phase synthetic scheme for improved polyamides.

DETAILED DESCRIPTION

Figure 1B:
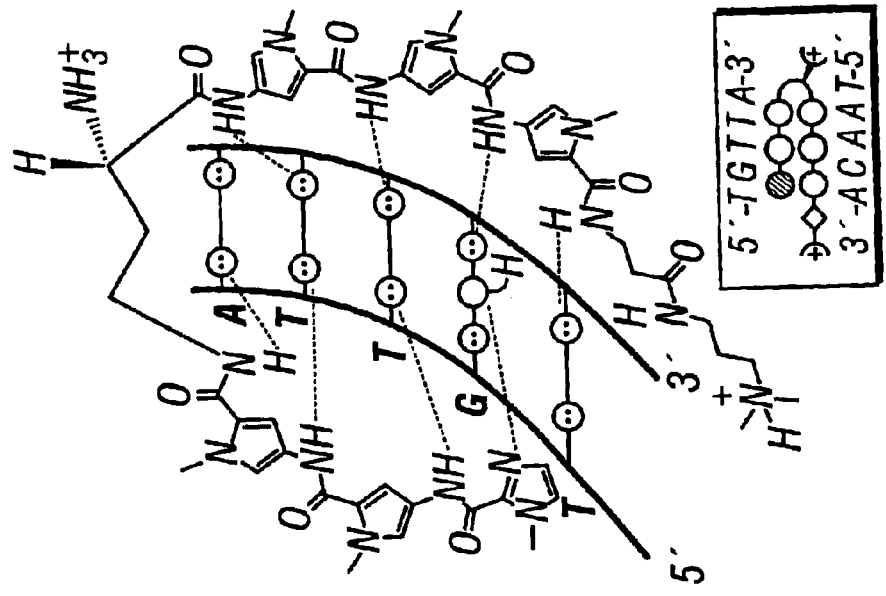
FIGS. 1A and 1B. A. Hydrogen bonding model of polyamide 1-R, ImPyPy-(R)$^{H_2N}$γ-PyPyPy-β-Dp, to the DNA sequence 5'-TGTTA-3'. B. Binding model of polyamide 1-S, ImPyPy-(S)$^{H_2N}$γ-PyPyPy-β-Dp, to the DNA sequence 5'-TGTTA-3'.

Within this application, unless otherwise stated, definitions of the terms and illustration of the techniques of this application may be found in any of several well-known references such as: Sambrook, J., et al., *Molecular Cloning: A Laboratory Manual*, Cold Spring Harbor Laboratory Press (1989); Goeddel, D., ed., *Gene Expression Technology, Methods in Enzymology*, 185, Academic Press, San Diego, Calif. (1991); "Guide to Protein Purification" in Deutshcer, M. P., ed., *Methods in Enzymology*, Academic Press, San Diego, Calif. (1989); Innis, et al., *PCR Protocols: A Guide to Methods and Applications*, Academic Press, San Deigo, Calif. (1990); Freshney, R. I., *Culture of Animal Cells: A Manual of Basic Technique*, 2$^{nd}$ Ed., Alan Liss, Inc. New York, N.Y. (1987); Murray, E. J., ed., *Gene Transfer and Expression Protocols*, pp. 109–128, The Humana Press Inc., Clifton, N.J. and Lewin, B., *Genes, VI*, Oxford University Press, New York (1997).

For the purposes of this application, a promoter is a regulatory sequence of DNA that is involved in the binding of RNA polymerase to initiate transcription of a gene. A gene is a segment of DNA involved in producing a peptide, polypeptide or protein, including the coding region, non-coding regions preceding ("leader") and following ("trailer") the coding region, as well as intervening non-coding sequences ("introns") between individual coding segments ("exons"). Coding refers to the representation of amino acids, start and stop signals in a three base "triplet" code. Promoters are often upstream ("5 to") the transcription site of the corresponding gene. Other regulatory sequences of DNA in addition to promoters are known, including sequences involved with the binding of transcription factors, including response elements that are the DNA sequences bound by inducible factors. Enhancers comprise yet another group of regulatory sequences of DNA that can increase the utilization of promoters, and can function in either orientation (5'-3' or 3'-5') and in any location (upstream or downstream) relative to the promoter. Preferably, the regulatory sequence has a positive activity, i.e., binding of an endogeneous ligand (e.g. a transcription factor) to the regulatory sequence increases transcription, thereby resulting in increased expression of the corresponding target gene. In such a case, interference with transcription by binding a polyamide to a regulatory sequence would reduce or abolish expression of a gene.

The promoter may also include or be adjacent to a regulatory sequence known in the art as a silencer. A silencer sequence generally has a negative regulatory effect on expression of the gene. In such a case, expression of a gene may be increased directly by using a polyamide to prevent binding of a factor to a silencer regulatory sequence or indirectly, by using a polyamide to block transcription of a factor to a silencer regulatory sequence.

It is to be understood that the polyamides of this invention bind to double stranded DNA in a sequence specific manner. The function of a segment of DNA of a given sequence, such as 5'-TATAAA-3', depends on its position relative to other functional regions in the DNA sequence. In this case, if the sequence 5'-TATAAA-3' on the coding strand of DNA is positioned about 30 base pairs upstream of the transcription start site, the sequence forms part of the promoter region (Lewin, *Genes VI*, pp. 831–835). On the other hand, if the sequence 5'-TATAAA-3' is downstream of the transcription start site in a coding region and in proper register with the reading frame, the sequence encodes the tyrosyl and lysyl amino acid residues (Lewin, *Genes VI*, pp. 213–215).

While not being held to one hypothesis, it is believed that the binding of the polyamides of this invention modulate gene expression by altering the binding of DNA binding proteins, such as RNA polymerase, transcription factors, TBF, TFIIIB and other proteins. The effect on gene expression of polyamide binding to a segment of double stranded DNA is believed to be related to the function, e.g., promoter, of that segment of DNA.

It is to be understood by one skilled in the art that the improved polyamides of the present invention may bind to any of the above-described DNA sequences or any other sequence having a desired effect upon expression of a gene. In addition, U.S. Pat. No. 5,578,444 describes numerous promoter targeting sequences from which base pair sequences for targeting an improved polyamide of the present invention may be identified.

It is generally understood by those skilled in the art that the basic structure of DNA in a living cell includes both major and a minor groove. For the purposes of describing the present invention, the minor groove is the narrow groove of DNA as illustrated in common molecular biology references such as Lewin, B., *Genes VI*, Oxford University Press, New York (1997).

To affect gene expression in a cell, which may include causing an increase or a decrease in gene expression, a effective quantity of one or more polyamide is contacted with the cell and internalized by the cell. The cell may be contacted in vivo or in vitro. Effective extracellular concentrations of polyamides that can modulate gene expression range from about 10 nanomolar to about 1 micromolar. Gottesfeld, J. M., et al., *Nature* 387 202–205 (1997). To determine effective amounts and concentrations of polyamides in vitro, a suitable number of cells is plated on tissue culture plates and various quantities of one or more polyamide are added to separate wells. Gene expression following exposure to a polyamide can be monitored in the cells or medium by detecting the amount of the protein gene product present as determined by various techniques utilizing specific antibodies, including ELISA and western blot. Alternatively, gene expression following exposure to a polyamide can be monitored by detecting the amount of messenger RNA present as determined by various techniques, including northern blot and RT-PCR.

Similarly, to determine effective amounts and concentrations of polyamides for in vivo administration, a sample of body tissue or fluid, such as plasma, blood, urine, cerebrospinal fluid, saliva, or biopsy of skin, muscle, liver, brain or other appropriate tissue source is analyzed. Gene expression following exposure to a polyamide can be monitored by detecting the amount of the protein gene product present as determined by various techniques utilizing specific antibodies, including ELISA and western blot. Alternatively, gene expression following exposure to a polyamide can be monitored by the detecting the amount of messenger RNA present as determined by various techniques, including northern blot and RT-PCR.

The polyamides of this invention may be formulated into diagnostic and therapeutic compositions for in vivo or in vitro use. Representative methods of formulation may be found in *Remington: The Science and Practice of Pharmacy*, 19th ed., Mack Publishing Co., Easton, Pa. (1995).

For in vivo use, the polyamides may be incorporated into a physiologically acceptable pharmaceutical composition that is administered to a patient in need of treatment or an animal for medical or research purposes. The polyamide composition comprises pharmaceutically acceptable carriers, excipients, adjuvants, stabilizers, and vehicles. The composition may be in solid, liquid, gel, or aerosol form. The polyamide composition of the present invention may be administered in various dosage forms orally, parentally, by inhalation spray, rectally, or topically. The term parenteral as used herein includes, subcutaneous, intravenous, intramuscular, intrasternal, infusion techniques or intraperitoneally.

The selection of the precise concentration, composition, and delivery regimen is influenced by, inter alia, the specific pharmacological properties of the particular selected compound, the intended use, the nature and severity of the condition being treated or diagnosed, the age, weight, gender, physical condition and mental acuity of the intended recipient as well as the route of administration. Such considerations are within the purview of the skilled artisan. Thus, the dosage regimen may vary widely, but can be determined routinely using standard methods.

Polyamides of the present invention are also useful for detecting the presence of double stranded DNA of a specific sequence for diagnostic or preparative purposes. The sample containing the double stranded DNA can be contacted by polyamide linked to a solid substrate, thereby isolating DNA comprising a desired sequence. Alternatively, polyamides linked to a suitable detectable marker, such as biotin, a hapten, a radioisotope or a dye molecule, can be contacted by a sample containing double stranded DNA.

The design of bifunctional sequence specific DNA binding molecules requires the integration of two separate entities: recognition and functional activity. Polyamides that specifically bind with subnanomolar affinity to the minor groove of a predetermined sequence of double stranded DNA are linked to a functional molecule, providing the corresponding bifunctional conjugates useful in molecular biology, genomic sequencing, and human medicine. Polyamides of this invention can be conjugated to a variety of functional molecules, which can be independently chosen from but is not limited to arylboronic acids, biotins, polyhistidines comprised from about 2 to 8 amino acids, haptens to which an antibody binds, solid phase supports, oligodeoxynucleotides, N-ethylnitrosourea, fluorescein, bromoacetamide, iodoacetamide, DL-α-lipoic acid, acridine, captothesin, pyrene, mitomycin, texas red, anthracene, anthrinilic acid, avidin, DAPI, isosulfan blue, malachite green, psoralen, ethyl red, 4-(psoraen-8-yloxy)-butyrate, tartaric acid, (+)-α-tocopheral, psoralen, EDTA, methidium, acridine, Ni(II)•Gly-Gly-His, thiazole orange (TO), Dansyl, pyrene, N-bromoacetamide, and gold particles. Such bifunctional polyamides are useful for DNA affinity capture, covalent DNA modification, oxidative DNA cleavage, DNA photocleavage. Such bifunctional polyamides are useful for DNA detection by providing a polyamide linked to a detectable label. Detailed instructions for synthesis of such bifunctional polyamides can be found in copending U.S. provisional application 60/043,444, the teachings of which are incorporated by reference.

DNA complexed to a labeled polyamide can then be determined using the appropriate detection system as is well known to one skilled in the art. For example, DNA associated with a polyamide linked to biotin can be detected by a streptavidin/alkaline phosphatase system.

The present invention also describes a diagnostic system, preferably in kit form, for assaying for the presence of the double stranded DNA sequence bound by the polyamide of this invention in a body sample, such brain tissue, cell suspensions or tissue sections, or body fluid samples such as CSF, blood, plasma or serum, where it is desirable to detect the presence, and preferably the amount, of the double stranded DNA sequence bound by the polyamide in the sample according to the diagnostic methods described herein.

The diagnostic system includes, in an amount sufficient to perform at least one assay, a specific polyamide as a separately packaged reagent. Instructions for use of the packaged reagent(s) are also typically included. As used herein, the term "package" refers to a solid matrix or material such as glass, plastic (e.g., polyethylene, polypropylene or polycarbonate), paper, foil and the like capable of holding within fixed limits a polyamide of the present invention. Thus, for example, a package can be a glass vial used to contain milligram quantities of a contemplated polyamide or it can be a microliter plate well to which microgram quantities of a contemplated polypamide have been operatively affixed, i.e., linked so as to be capable of being bound by the target DNA sequence. "Instructions for use" typically include a tangible expression describing the reagent concentration or at least one assay method parameter such as the relative amounts of reagent and sample to be admixed, maintenance time periods for reagent or sample admixtures, temperature, buffer conditions and the like. A diagnostic system of the present invention preferably also includes a detectable label and a detecting or indicating means capable of signaling the binding of the contemplated polyamide of the present invention to the target DNA sequence. As noted above, numerous detectable labels, such as biotin, and detecting or indicating means, such as enzyme-linked (direct or indirect) streptavidin, are well known in the art.

Trauger, et al. (*Nature*, 382: 559–561) and Swalley, et al. (*J. Am. Chem. Soc.* 119: 6953–6961) have described recognition of DNA by certain polyamides at subnanomolar concentrations. Pairing specific carboxyamide groups allows for recognition of specific DNA sequences (Swalley, et al. supra). Polyamides comprising Hp, Im, and Py provide for coded targeting of pre-determined DNA sequences with high affinity and specificity. Hp, Im, and Py polyamides may be combined to form Im/Py, Py/Im, Hp/Py, and Py/Hp binding pairs which complement the four Watson-Crick base pairs A, C, G, and T. Table 1 illustrates such pairings.

TABLE 1

Pairing codes for Base Pair Recognition*

| Pair | G·C | C·G | T·A | A·T |
|---|---|---|---|---|
| Im/Py | + | − | − | − |
| Py/Im | − | + | − | − |
| Hp/Py | − | − | + | − |
| Py/Hp | − | − | − | + |

*favored (+),
disfavored (−)

Three-, four-, five- or six-ring improved polyamides of the present invention are covalently coupled to form six-, eight-, ten- or twelve-ring structures, respectively, that bind specifically to four or six base pair targets, respectively, at subnanomolar concentrations. As such, the improved polyamides of the present invention may be directed to any DNA sequence comprised of A, C, G, or T.

The improved polyamides of the present invention comprise those having at least three consecutive carboxamide pairings for binding DNA in the minor groove of a regulatory sequence of a duplex gene sequence and a chiral hairpin turn with a stereochemical center substituted at the γ-position of the chiral hairpin turn of the molecule with the R-enantiomer of 2,4-diaminobutyric acid (H$_2$NHCHCH$_2$CHNH$_2$COOH; "(R)$^{H_2N}$γ"). In addition, the present invention provides a methodology for covalently linking existing hairpin motifs without compromising DNA-binding and sequence specificity. The present invention provides improved polyamides for binding the minor groove of DNA to affect gene expression. Preferably, the bound polyamide inhibits gene expression.

The present invention comprises improved polyamides having three or four-ring polyamide structures covalently coupled to form six-, eight-, ten- or twelve-ring hairpin structures, respectively, of the general structures I–VIII:

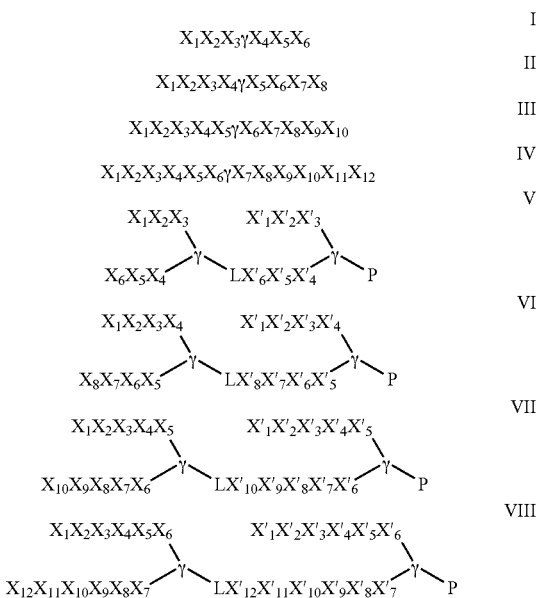

where $X_{1-12}$ and $X'_{1-12}$ are independently an imidazole such as N-methylimidazole (Im), a pyrrole such as N-methylpyrrole (Py), or a hydroxypyrrole such as 3-hydroxy-N-methyl pyrrole (Hp). In addition, an improved polyamide of the present invention may further include a aliphatic amino acid such as β-alanine residue (β), an amide group such as dimethylaminopropylamide (Dp), an alcohol such as EtOH, an acid such as EDTA, or any derivative thereof may be joined to the β residue.

β-alanine may also be utilized in place of a pyrrole amino acid in Formulas I–VIII. The use of β-alanine in place of a pyrrole or hydroxypyrrole amino acid in the synthetic methods provides aromatic/aliphatic pairing (Im/β, β/Im, Py/β, and β/Py) and aliphatic/aliphatic pairing (β/β) substitution. Such substitutions may comprise those described in provisional application 60/042,022, incorporated herein by reference. The use of γ-aminobutyric acid, or a substituted γ-aminobutyric acid such as (R)-2,4 diaminobutyric acid, provides for preferred hairpin turns. Many other groups suitable for the purposes of practicing this invention are well known and widely available to one skilled in the art.

Figures 1, 4A:
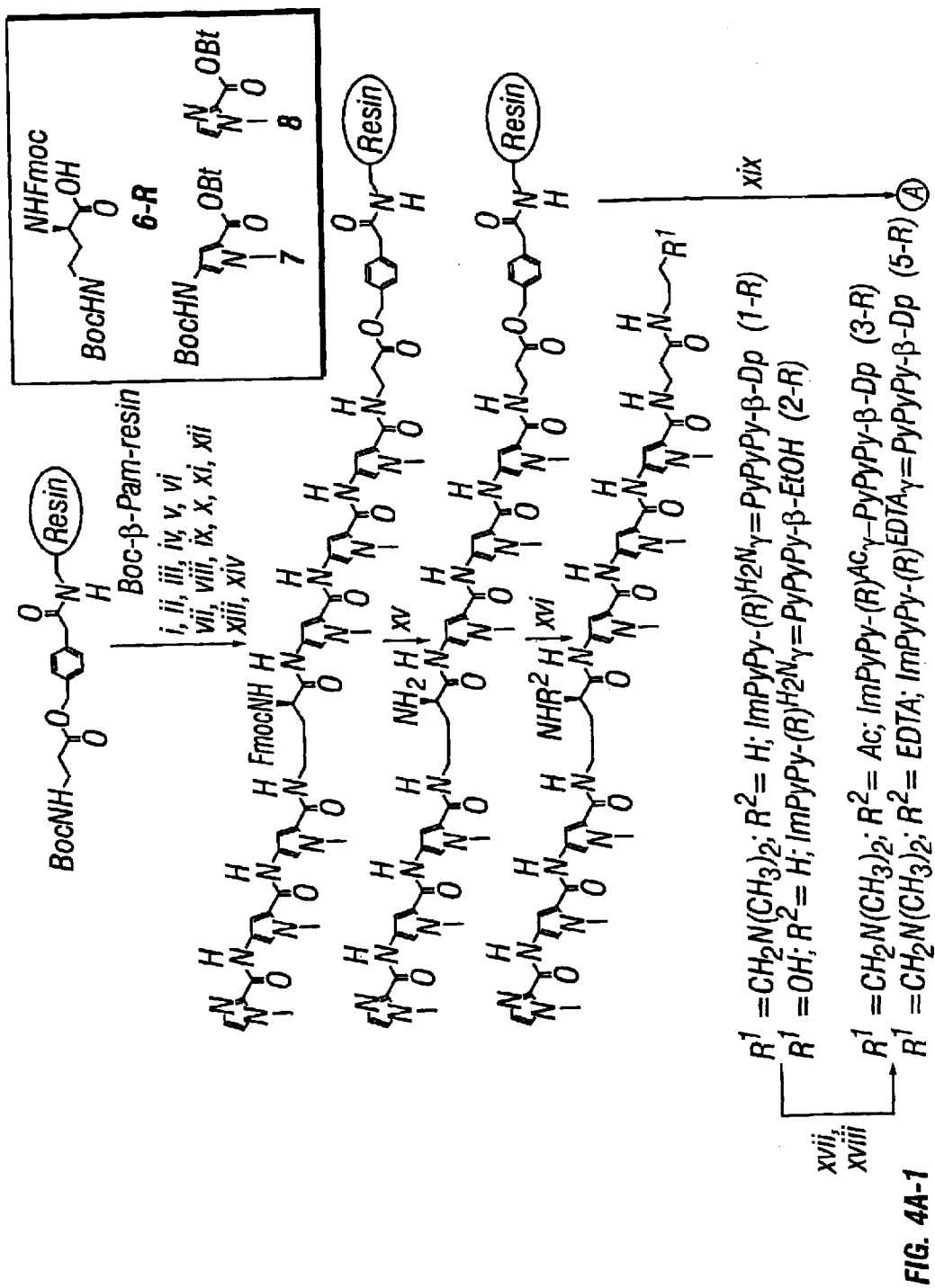

The polyamide subunit structures I–VIII above are covalently coupled through the γ residue which represents a —NH—CH$_2$—CH$_2$—CH$_2$—CONH— hairpin linkage derived from γ-aminobutyric acid or a chiral hairpin linkage derived from R-2,4-diaminobutyric acid. The present invention provides the reagents and methodologies for substituting the γ-residue of certain polyamides with a moiety such as (R)-2,4-diaminobutyric acid ((R)$^{H_2N}$γ). The NMR structure of a hairpin polyamide of sequence composition ImPyPy-γ-PyPyPy complexed with a 5'-TGTTA-3' target site indicated that it was possible to substitute the α-position of the γ-aminobutyric acid residue within the hairpin-DNA complex (de Claire, et al. *J. Am. Chem. Soc.* 1997, 119, 7909). Modeling indicated that replacing the α-H of γ with an amino group that may confer an R-configuration at the α-carbon could be accommodated within the floor and walls of the minor groove as demonstrated in FIGS. 1 and 2A. In contrast, the (S)-2,4-diaminobutyric acid ((S)$^{H_2N}$γ) linked hairpin is predicted to clash with the walls of the minor groove of the DNA helix as illustrated in FIGS. 1 and 2B.

In Formulas V–VIII, L represents an amino acid linking group such as β-alanine or 5-aminovaleric acid (δ) bound to the γ residue of a first polyamide and to the carboxytail of a second polyamide. As such, two or more polyamides may be linked, forming a tandemly-linked polyamide. Such a polyamide is said to be tandemly-linked or a tandem-linked polyamide.

P represents from zero to ten polyamides of formulas I–VIII that may be tandemly linked to the second polyamide. Preferably, P represents from zero to eight polyamids of formulas I–VIII. More preferably, P represents from zero to six polyamids of formulas I–VIII. More preferably, P represents from zero to four polyamides of formulas I–VIII. Most preferably, P represents from zero to two polyamides of formulas I–VIII. Tandem linking of polyamides provides expanded binding site size and increased binding affinity without compromising selectivity. Many other groups suitable for the purposes of practicing this invention are well known and widely available to one skilled in the art.

Baird, et al. (*J. Am. Chem. Soc.* 118: 6141–6146) and PCT/US97/003332 describe methods for synthesis of polyamides which are suitable for preparing polyamides of this invention. Polyamides of the present invention may be synthesized by solid phase methods using compounds such as Boc-protected 3-methoxypyrrole, imidazole, and pyrrole aromatic amino acids, which are cleaved from the support by aminolysis, deprotected with sodium thiophenoxide, and purified by reverse-phase HPLC. The identity and purity of the polyamides may be verified using any of a variety of analytical techniques available to one skilled in the art such as 1H-NMR, analytical HPLC, and/or matrix-assisted laser-desorption ionization time-of-flight mass spectrometry (MALDI-TOF MS-monoisotropic).

Described herein is the synthesis of a new class of chiral hairpin polyamides and their characterization with regard to DNA binding affinity and sequence specificity. The present invention provides one skilled in the art with the reagents and methodologies for substitution of the prochiral γ-turn with either enantiomer of 2,4-diaminobutyric acid. In addition, the invention provides the dicationic six-ring anantiomeric polyamides (+)-ImPyPy-(R)$^{H_2N}$γ-PyPyPy-β-Dp (1-R) and (−)-ImPyPy-(S)$^{H_2N}$γ-PyPyPy-β-Dp (1-S) which may be synthesized by solid phase methods. In certain experiments, the monocationic polyamide (+)-ImPyPy-(R)$^{H_2N}$γPyPyPy-β-EtOH (2-R), which lacks a charge at the C-terminus, may be prepared and utilized as a control. To further study steric effects, the γ-acetamido polyamides (+)-ImPyPy-(R)$^{Ac}$γ-PyPyPy-β-Dp (3-R) and (−)-ImPyPy-(S)$^{Ac}$γ-PyPyPy-β-Dp (3-S) may be utilized (FIG. 3; Baird, et al. 1996. *J. Am. Chem. Soc.* 118: 6141). The present invention further provides the EDTA analogs ImPyPy-(R)$^{H_2N}$γ-PyPyPy-β-Dp-EDTA•Fe(II) (4-R•Fe(II)), ImPyPy-(S)$^{H_2N}$γ-PyPyPy-β-Dp-EDTA•Fe(II) (4-S•Fe(II)), ImPyPy-(R)$^{EDTA•Fe(II)}$γ-PyPyPy-β-Dp (5-R•Fe(II)), and ImPyPy-(S)$^{EDTA•Fe(II)}$γ-PyPyPy-β-Dp (5-S•Fe(II)) that may be utilized to to confirm the binding orientation of the modified hairpins at specific DNA binding sites (FIG. 3).

Figure 14C:
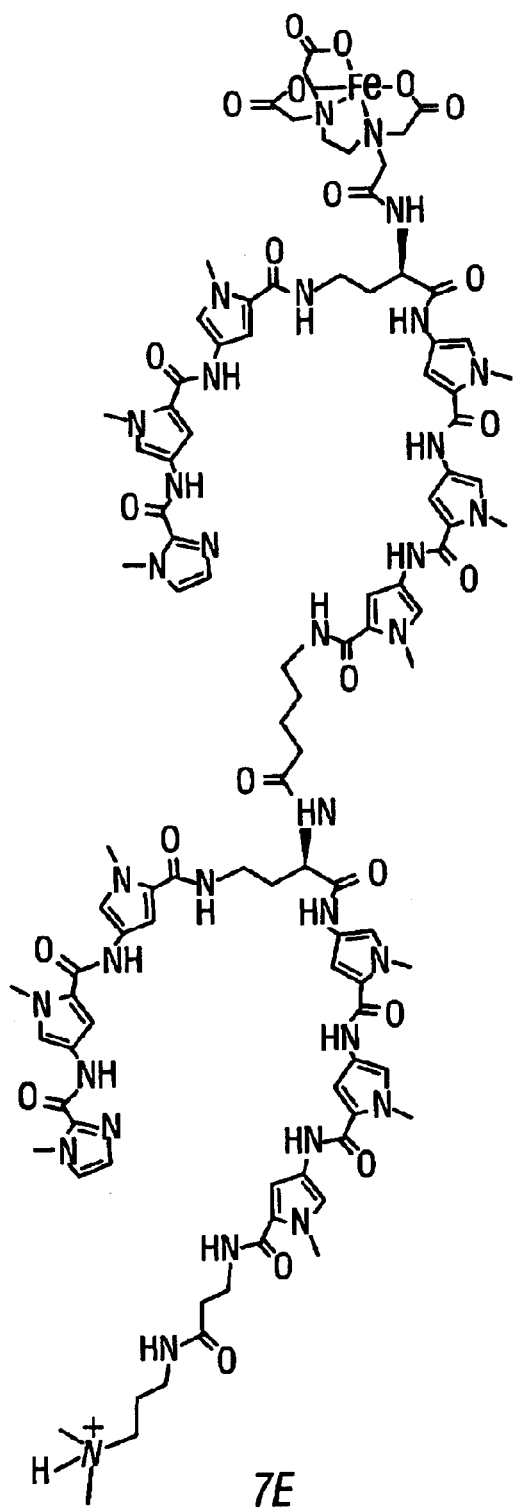
FIG. 14. Structures of exemplary twelve-ring polyamides.
Figure 15A:
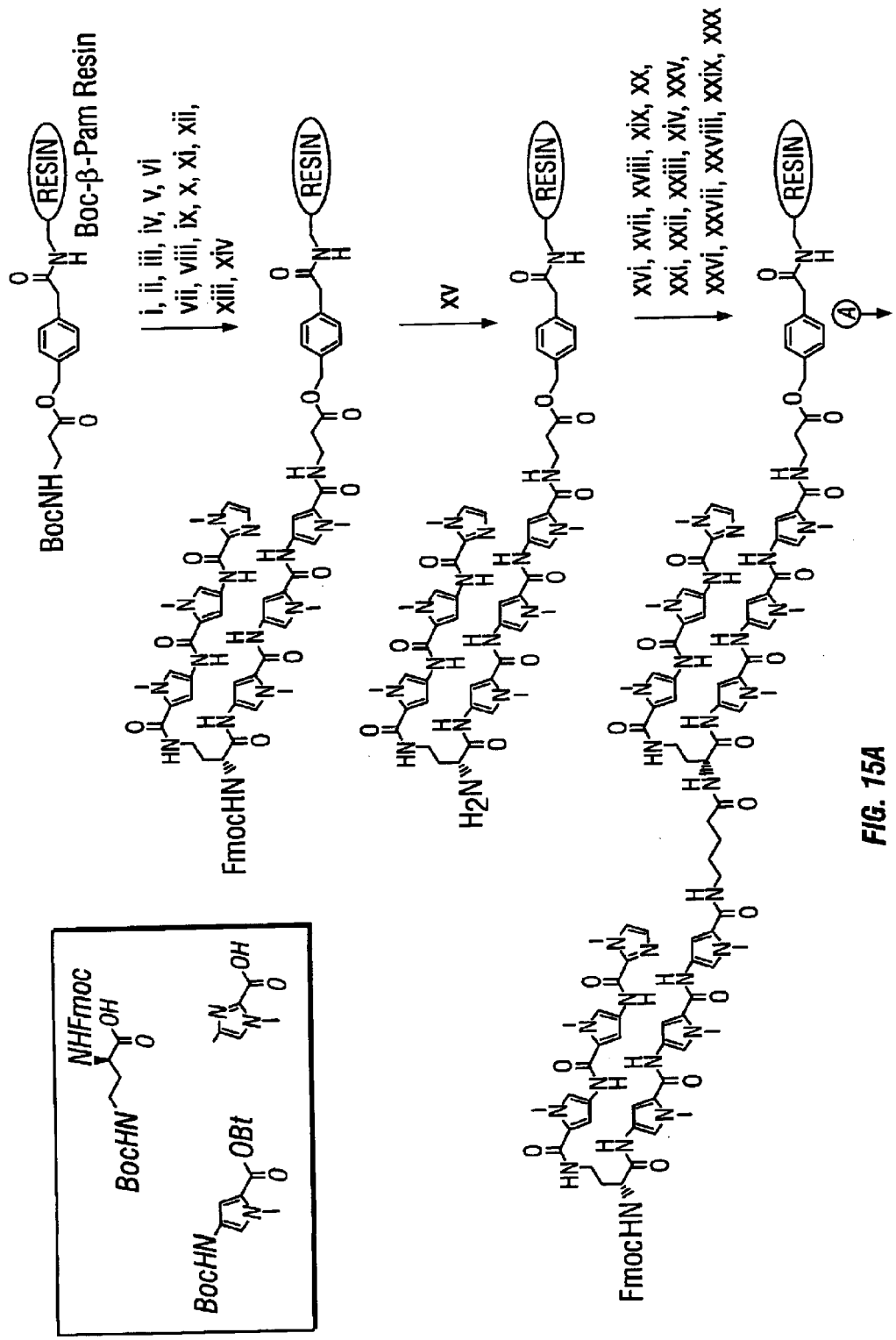
FIGS. 15A–15B. Synthesis of tandemly-linked polyamides.
Figure 15B:
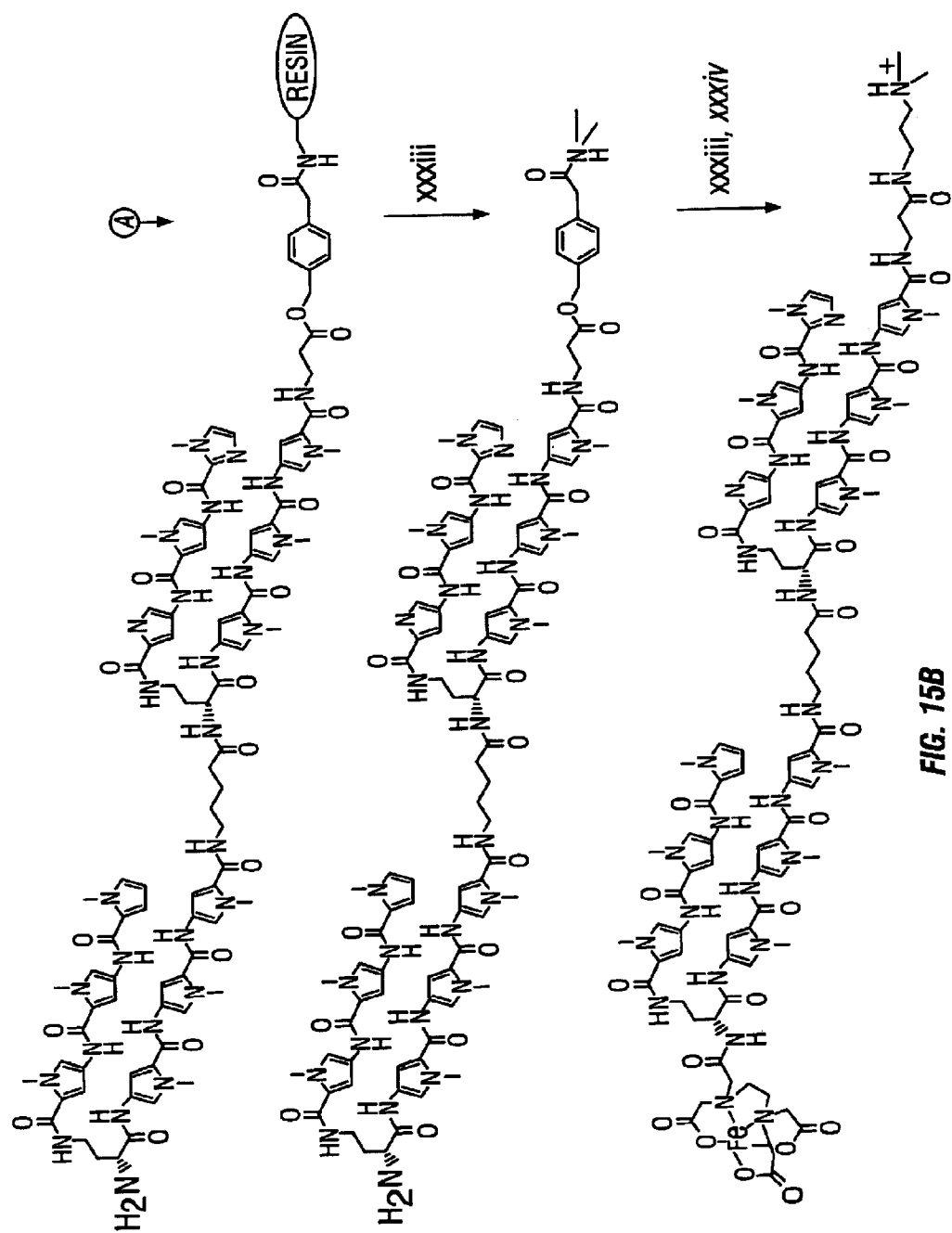
Figure 16:
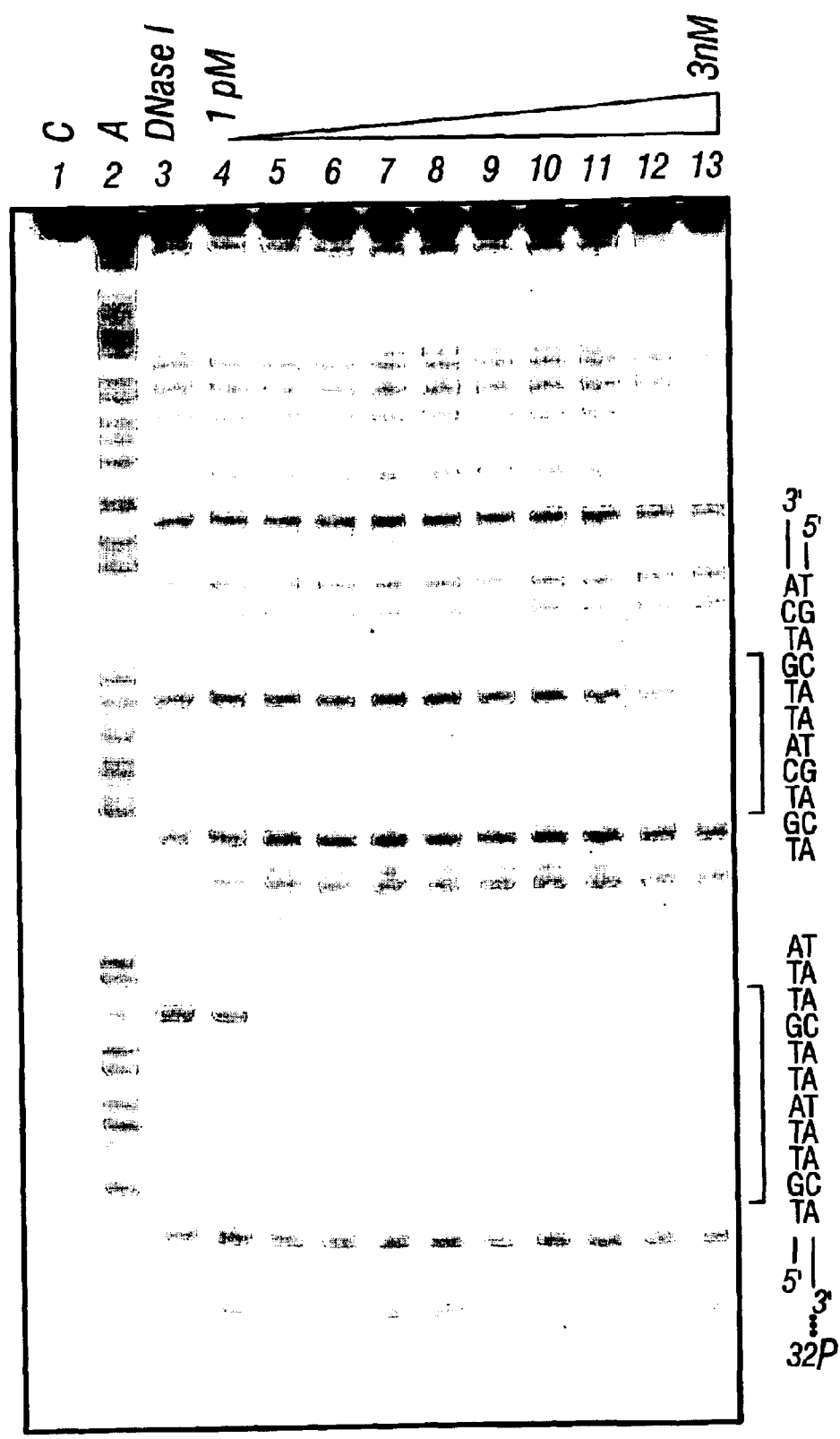
FIG. 16. Quantitative DNA footprint titrations of an exemplary tandemly-linked polyamide using SEQ ID NOS 27 and 28.
Figure 17J:
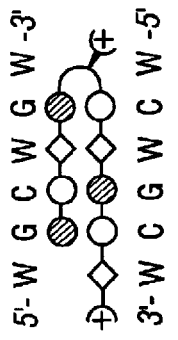
FIGS. 17A–17V. Exemplary tandemly-linked polyamides (17V shows tandemly linked polyamides binding to SEQ ID NOS 29 and 30.
Figure 17L:
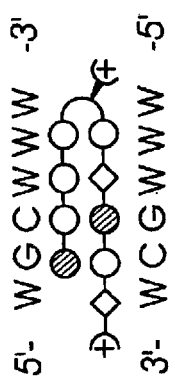
Figure 17N:
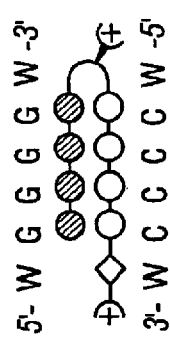
Figure 17M:
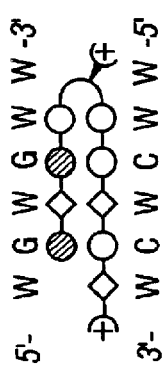
Figure 17O:
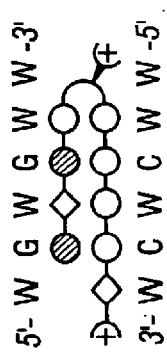
Figure 17R:
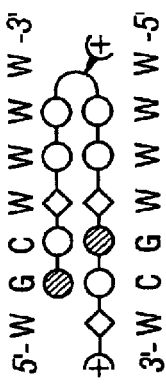
Figure 17P:
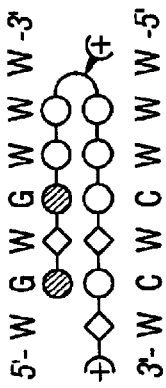
Figure 17S:
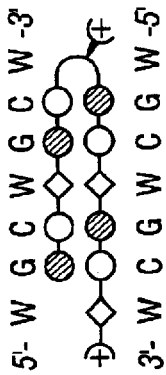
Figures 17T, 17U, 17V:
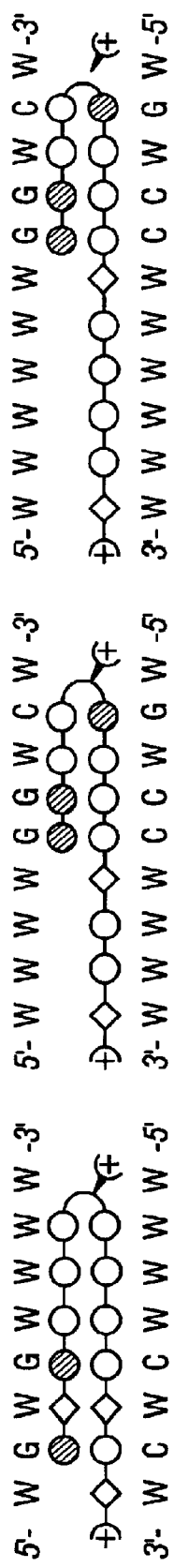

Tandemly-linked polyamides of the present invention are also provided by the instant invention. The primary turn-amino group provides a potential site for covalently tethering two hairpins. In one potential linkage arrangement, the C-terminus of the first hairpin is coupled to the α-amino group of the γ-turn of the second amino acid linker. The present invention provides twelve ting polyamides exemplified by ImPyPy-(R)[ImPyPy-(R)$^{H_2N}$γPyPyPy-β]$^{HN}$γPyPyPy-β-Dp and ImPyPy-(R)[ImPyPy-(R)$^{H_2N}$γPyPyPy-δ]$^{HN}$γPyPyPy-β-Dp (FIG. 14). The DNA binding properties of certain polyamides of the present invention were determined on a series of DNA fragments containing 10, 11 and 12 base pair target sites. The present invention further provides an exemplary affinity cleaving derivative ImPyPy-(R)[ImPyPy-(R)$^{EDTA}$γPyPyPy-δ]$^{HN}$γPyPyPy-β-Dp, which was utilized to confirm a single predicted binding orientation for the tandemly-linked polyamide. Methodologies for the determination of the DNA-binding affinity and sequence selectivity of tandem improved polyamides is also provided.

The present invention reveals to one skilled in the art properties of chiral structure elements that may be utilized as a guide in the design of more efficient polyamides. For instance, the present invention provides amine substituents on the (R)$^{H_2N}$γ turn amino acid that enhance the DNA binding affinity and specificity relative to the unsubstituted parent hairpin, providing for an optimized class of hairpin polyamides. Also provided are acetamido substituents at the (R)$^{H_2N}$γ that do not compromise affinity or specificity relative to the parent hairpin, providing for a convenient synthetic attachment point at the 'capped' end of the molecule. In addition, the invention described herein provides (S)$^{H_2N}$γ-linked hairpins that bind with enhanced affinity to reverse orientation sites relative to the parent hairpin and (R)$^{H_2N}$γ-linked hairpins that bind with enhanced specificity relative to the parent hairpin indicating that γ-turn substituents may regulate hairpin polyamide binding orientational preference. The invention further provides the skilled artisan with the necessary tools and methodologies for developing tandemly-linked polyamides to increase the polyamide binding site size, and increase affinity without compromising sequence selectivity.

The examples listed above and those illustrated below represent only certain embodiments of the present invention and are not limiting of the specification and claims in any way.

EXAMPLES

Example 1

Synthesis of Improved Polyamides

Two polyamide-resins ImPyPy-(R)$^{Fmoc}$γ-PyPyPy-β-Pam-resin and ImPyPy-(S)$^{Fmoc}$γ-PyPyPy-β-Pam-resin, were synthesized in 14 steps from Boc-β-alanine-Pam-resin (1 g resin, 0.2 mmol/g substitution) using previously described Boc-chemistry machine-assisted protocols (FIG. 4; Baird, et al. *J. Am. Chem. Soc.* 1996, 118, 6141). (R)- and (S)-2,4-diaminobutyric acid residues were introduced as orthogonally protected N-γ-Fmoc-N-γ-Boc derivatives (HBTU, DIEA). Fmoc protected polyamide resins ImPyPy-(R)$^{Fmoc}$γ-PyPyPy-β-Pam-resin and ImPyPy-(S)$^{Fmoc}$γ-PyPyPy-β-Pam-resin were treated with 1:4 DMF:Piperidine (22° C., 30 min.) to provide ImPyPy-(R)$^{H_2N}$γ-PyPyPy-β-Pam-resin and ImPyPy-(S)$^{H_2N}$γ-PyPyPy-β-Pam-resin, respectively. A single-step aminolysis of the resin ester linkage was used to cleave the polyamide from the solid support. A sample of resin (240 mg) was treated with either dimethylaminopropylamine (55° C., 18 h) to provide 1-R, 1-S, 3-R, and 3-S or ethanolamine (55° C., 18 h) to provide 2-R. Resin cleavage products were purified by reverse phase HPLC to provide ImPyPy-(R)$^{H_2N}$γ-PyPyPy-β-Dp (1-R), ImPyPy-(S)$^{H_2N}$γ-PyPyPy-β-Dp (1-S), and ImPyPy-(R)$^{H_2N}$γ-PyPyPy-β-EtOH (2-R). The stereochemical purity of 1-R was determined to be >98% by Mosher amide analysis (Dale, et al. *J. Am.*

Chem. Soc. 1973, 95, 512; Yamaguchi, et al. *Asymmetric Synthesis* (Vol. 1), *Analytical Methods* p. 125–152, J. D. Morrison (ed.) Academic Press (1983)). 1-R,R and 1-R,S Mosher amides were prepared by reaction of 1-R with HOBt activated esters generated in situ from (R)-α-methoxy-α-(triflouromethyl)phenylacetic acid and (S)-α-methoxy-α-(triflouromethyl)phenylacetic acid. For synthesis of analogs modified with EDTA at the carboxy-terminus, the amine-resin was treated with Boc-anhydride (DMF, DIEA, 55° C., 30 min) to provide ImPyPy-(R)$^{Boc}$γPyPyPy-β-Pam-resin and ImPyPy-(S)$^{Boc}$γ-PyPyPy-β-Pam-resin (FIG. 4). A sample of Boc-resin was then cleaved with 3,3'-diamino-N-methyldipropylamine (55° C., 18 h) and purified by reversed phase HPLC to provide either ImPyPy-(R)$^{Boc}$γ-PyPyPy-βDp-NH$_2$ (1-R-Boc-NH$_2$) or ImPyPy-(S)$^{Boc}$γ-PyPyPy-β-Dp-NH$_2$ (1-S-Boc-NH$_2$) which afford free primary amine groups at the C-terminus suitable for post-synthetic modification. The polyamide-amines 1-R-Boc-NH$_2$ and 1-S-Boc-NH$_2$ were treated with an excess of EDTA-dianhydride (DMSO/NMP, DIEA, 55° C., 15 min) and the remaining anhydride hydrolyzed (0.1 M NaOH, 55° C., 10 min). The Boc protected EDTA modified polyamides ImPyPy-(R)$^{Boc}$γ-PyPyPy-β-Dp-EDTA (4-R-Boc) and ImPyPy-(S)$^{Boc}$γ-PyPyPy-β-Dp-EDTA (4-S-Boc) were isolated by HPLC. Individual Boc-EDTA-polyamides were deprotected with neat TFA (22° C., 1 h) to provide the respective C-terminal EDTA derivatives, ImPyPy-(R)$^{H_2N}$γ-PyPyPy-β-Dp-EDTA (4-R) and ImPyPy-(S)$^{H_2N}$γ-PyPyPy-β-Dp-EDTA (4-S). For the synthesis of acetamide-turn or EDTA-turn derivatives, a sample of the γ-amino polyamide ImPyPy-(R)$^{H_2N}$γ-PyPyPy-β-Dp (1-R) or ImPyPy-(S)$^{H_2N}$γ-PyPyPy-β-Dp (1-S) was treated with an excess of either acetic anhydride or EDTA-dianhydride (DMSO/NMP, DIEA 55° C., 30 min) and the remaining anhydride hydrolyzed (0.1 M NaOH, 55° C., 10 min). The polyamides ImPyPy-(R)$^{Ac}$γ-PyPyPy-β-Dp (3-R), ImPyPy-(S)$^{Ac}$γ-PyPyPy-β-Dp (3-S), ImPyPy-(R)$^{EDTA}$γ-PyPyPy-β-Dp (5-R) and ImPyPy-(S)$^{EDTA}$γ-PyPyPy-β-Dp (5-S) were then isolated by reverse phase HPLC. The six-ring hairpin polyamides described here are soluble in aqueous solution at concentrations 10 mM at 37° C.

A. Materials

Dicyclohexylcarbodiimide (DCC), Hydroxybenzotriazole (HOBt), 2-(1H-Benzotriazole-1-yl)-1,1,3,3-tetramethyluronium hexa-fluorophosphate (HBTU) and 0.2 mmol/gram Boc-β-alanine-(-4-carboxamidomethyl)-benzyl-ester-copoly(styrene-divinylbenzene) resin (Boc-γ-Pam-Resin) was purchased from Peptides International (0.2 mmol/gram) (R)-2-Fmoc-4-Boc-diaminobutyric acid, (S)-2-Fmoc-4-Boc-diaminobutyric acid, and (R)-2-amino-4-Boc-diaminobutyric acid were from Bachem. N,N-diisopropylethylamine (DIEA), N,N-dimethylformamide (DMF), N-methylpyrrolidone (NMP), DMSO/NMP, Acetic anhydride (Ac$_2$O), and 0.0002 M potassium cyanide/pyridine were purchased from Applied Biosystems. Dichloromethane (DCM) and triethylamine (TEA) were reagent grade from EM, thiophenol (PhSH), dimethylaminopropylamine (Dp), (R)-α-methoxy-α-(trifluoromethyl) phenylacetic acid ((R)MPTA) and (S)-α-methoxy-α-(trifluoromethyl)phenylacetic acid ((S)MPTA) were from Aldrich, trifluoroacetic acid (TFA) Biograde from Halocarbon, phenol from Fisher, and ninhydrin from Pierce. All reagents were used without further purification.

Quik-Sep polypropylene disposable filters were purchased from Isolab Inc. A shaker for manual solid phase synthesis was obtained from St. John Associates, Inc. Screw-cap glass peptide synthesis reaction vessels (5 mL and 20 mL) with a #2 sintered glass frit were made as described by Kent (*Annu. Rev. Biochem.* 1988, 57, 957). $^1$H NMR spectra were recorded on a General Electric-QE NMR spectrometer at 300 MHz with chemical shifts reported in parts per million relative to residual solvent. UV spectra were measured in water on a Hewlett-Packard Model 8452A diode array spectrophotometer. Optical rotations were recorded on a JASCO Dip 1000 Digital Polarimeter. Matrix-assisted, laser desorption/ionization time of flight mass spectrometry (MALDI-TOF) was performed at the Protein and Peptide Microanalytical Facility at the California Institute of Technology. HPLC analysis was performed on either a HP 1090M analytical HPLC or a Beckman Gold system using a RAINEN C$_{18}$, Microsorb MV, 5 μm, 300×4.6 mm reversed phase column in 0.1% (wt/v) TFA with acetonitrile as eluent and a flow rate of 1.0 mL/min, gradient elution 1.25% acetonitrile/min. Preparatory reverse phase HPLC was performed on a Beckman HPLC with a Waters DeltaPak 25×100 mm, 100 μm C18 column equipped with a guard, 0.1% (wt/v) TFA, 0.25% acetonitrile/min. Distilled water was obtained from a Millipore MilliQ water purification system, and all buffers were 0.2 μm filtered.

Enzymes were purchased from Boehringer-Mannheim and used with their supplied buffers. Deoxyadenosine and thymidine 5'-[γ$^{32}$P] triphosphates were obtained from Amersham, and deoxyadenosine 5'-[γ$^{32}$P]triphosphate was purchased from I.C.N. Sonicated, deproteinized calf thymus DNA was acquired from Pharmacia. RNase free water was obtained from USB and used for all footprinting reactions. All other reagents and materials were used as received. All DNA manipulations were performed according to standard protocols (Sambrook, J.; Fritsch, E. F.; Maniatis, T. *Molecular Cloning*; Cold Spring Harbor Laboratory: Cold Spring Harbor, N.Y., 1989).

B. ImPyPy-(R)$^{H_2N}$γ-PyPyPy-β-Dp (1-R)

ImPyPy-(R)$^{Fmoc}$γ-PyPyPy-β-Pam-Resin was synthesized in a stepwise fashion by machine-assisted solid phase methods (Baird, et al. *J. Am. Chem. Soc.* 1996, 118, 6141). (R)-2-Fmoc-4-Boc-diaminobutyric acid (0.7 mmol) was incorporated as previously described for Boc-γ-aminobutyric acid. ImPyPy-(R)$^{Fmoc}$γ-PyPyPy-β-Pam-Resin was placed in a glass 20 mL peptide synthesis vessel and treated with DMF (2 mL), followed by piperidine (8 mL) and agitated (22° C., 30 min.). ImPyPy-(R)$^{H_2N}$γ-PyPyPy-β-Pam-resin was isolated by filtration, and washed sequentially with an excess of DMF, DCM, MeOH, and ethyl ether and the amine-resin dried in vacuo. A sample of ImPyPy-(R)$^{H_2N}$γ-PyPyPy-β-Pam-resin (240 mg, 0.18 mmol/gram) was treated with neat dimethylaminopropylamine (2 mL) and heated (55° C.) with periodic agitation for 16 h. Resin substitution can be calculated as $L_{new}(mmol/g)=L_{old}/(1+L_{old}(W_{new}-W_{old})\times 10^{-3})$, where L is the loading (mmol of amine per gram of resin), and W is the weight (gmol$^{-1}$) of the growing polyamide attached to the resin (Barlos, et al. *Int. J. Peptide Protein Res.* 1991, 37, 513). The reaction mixture was placed in an oven and periodically agitated (55° C., 16 h). The reaction mixture was then filtered to remove resin, 0.1% (wt/v) TFA added (6 mL) and the resulting solution purified by reversed phase HPLC. ImPyPy-(R)$^{H_2N}$γ-PyPyPy-β-Dp is recovered upon lyophilization of the appropriate fractions as a white powder (32 mg, 66% recovery). [α]$^{20}_D$+14.6 (c 0.05, H$_2$O); UV (H$_2$O)λ$_{max}$ 246, 310 (50, 000); $^1$H NMR (DMSO-d$_6$) 10.56 (s, 1 H), 10.47 (s, 1 H), 9.97 (s, 1 H), 9.94 (s, 1 H), 9.88 (s, 1 H), 9.4 (br s, 1 H), 8.28 (s, 3 H), 8.22 (m, 1 H), 8.03 (m, 2 H), 7.38 (s, 1 H), 7.25 (d, 1 H, J=1.6 Hz), 7.22 (d, 1 H, J=1.5 Hz), 7.19 (d, 1 H, J=1.5

Hz), 7.16 (d, 1 H, J=1.6 Hz), 7.14 (d, 1 H, J=1.8 Hz), 7.12 (d, 1 H, J=1.7 Hz), 7.03 (m, 2 H), 6.95 (d, 1 H, J=1.6 Hz), 6.91 (d, 1 H, J=1.6 Hz), 6.85 (d, 1 H, J=1.6 Hz), 3.96 (s, 3 H), 3.83 (s, 3 H), 3.81 (m, 6 H), 3.79 (s, 3 H), 3.76 (s, 3 H), 3.33 (q, 2 H, J=6.3 Hz), 3.25 (q, 2 H, J=5.7 Hz), 3.05 (q, 2 H, J=5.9 Hz), 2.96 (q, 2 H, J=5.3 Hz), 2.71 (d, 6 H, J=4.9 Hz), 2.32 (t, 2 H, J=7.1 Hz), 1.95 (q, 2 H, J=5.9 Hz), 1.70 (quintet, 2 H, J=7.3 Hz); MALDI-TOF-MS (monoisotopic), 992.5 (992.5 calc. for $C_{47}H_{62}N_{17}O_8$).

Figure 1A:
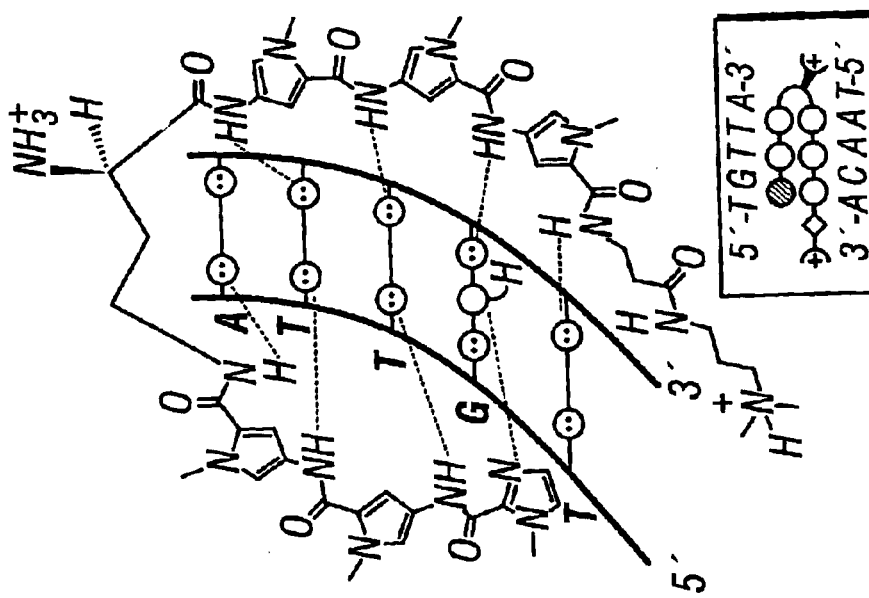
Figure 3A:
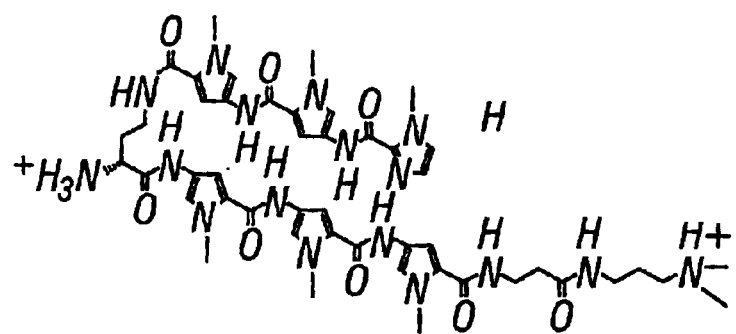
FIGS. 3A–3E. Structures of the 6-ring hairpin polyamides.
Figure 3B:
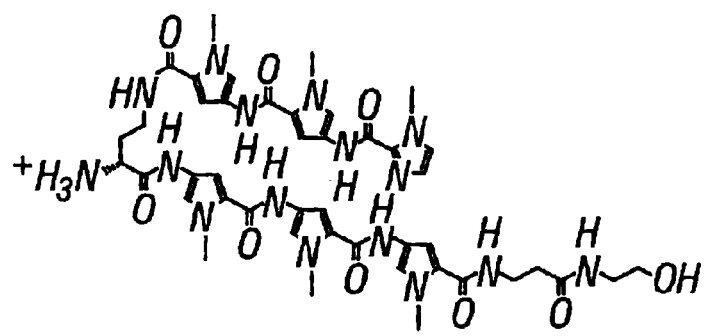
Figure 3C:
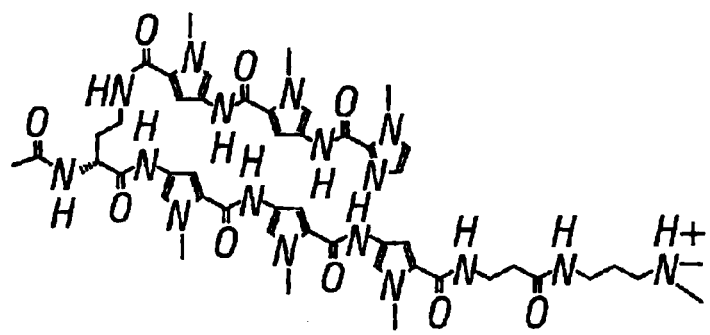
Figure 3D:
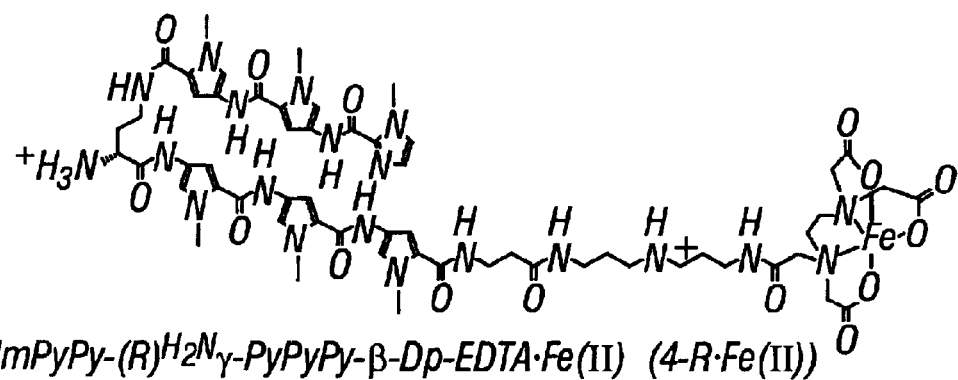
Figure 3E:
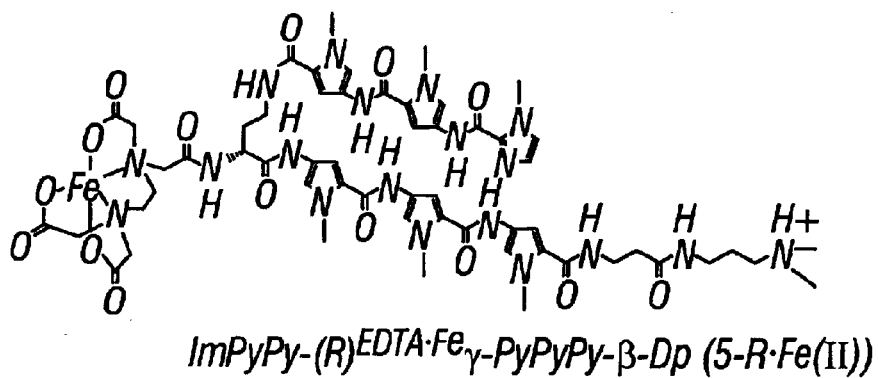
Figures 2, 4A:
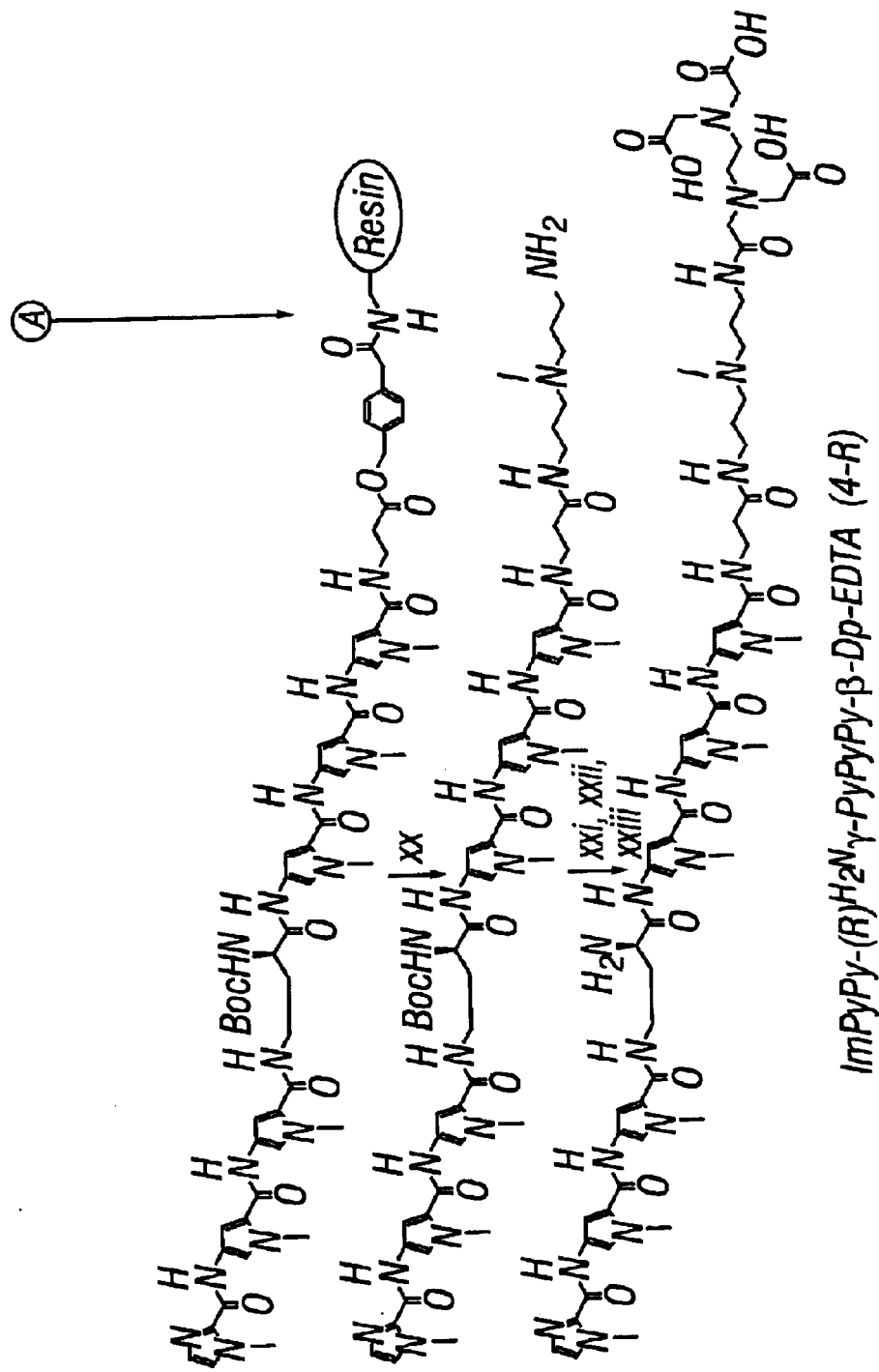

A hydrogen bonding model of the 1:1 polyamide:DNA complex formed between the hairpin polyamide ImPyPy-(R)$^{H_2N}$γ-PyPyPy-β-Dp (1-R) with a 5'-TGTTA-3' site is illustrated in FIG. 1A. Lone pairs of $N_3$ of purines and $O_2$ of pyrimidines are shown as circles with dots. The $N_2$ hydrogen of guanine is indicated by circles containing an "H" and putative hydrogen bonds are illustrated by dotted lines. A schematic binding model is also demonstrated where the imidazole and pyrrole rings are represented as shaded and unshaded spheres, respectively, and the β-alanine residue is represented as an unshaded diamond. FIG. 2 shows models derived from the NMR structure coordinates of ImPyPy-γ-PyPyPy-β-Dp•5'-TGTTA-3' using InsightII software. FIG. 3 shows the structure of the 2-R polyamides.

C. ImPyPy-(R)$^{(R)MTPA}$γ-PyPyPy-β-Dp (1-R,R)

(R)-α-methoxy-α-(triflouromethyl)phenylacetic acid (117 mg, 0.5 mmol) and HOBt (70 mg, 0.5 mmol) were dissolved in DMF (1 mL), DCC (100 mg, 0.5 mmol) added and the solution agitated for 30 min at 22° C. A sample of the activated ester solution (100 µL, 0.05 mmol) was added to ImPyPy-(R)$^{H_2N}$γ-PyPyPy-β-Dp 1-R (10 mg, 0.01 mmol), DIEA (50 µL) added, and the solution agitated for 3 h (22° C.). DMF (1 mL) followed by 0.1% (wt/v) TFA (6 mL) was then added to the reaction mixture and the resulting solution purified by reversed phase HPLC (1% acetonitrile/min.) under conditions which were determined to separate the diastereomers. ImPyPy-(R)$^{(R)MTPA}$γ-PyPyPy-β-Dp is recovered as a white powder upon lyophilization of the appropriate fractions (6 mg, 53% recovery). $^1$H NMR (DMSO-$d_6$) δ10.50 (s, 1 H), 10.14 (s, 1 H), 9.92 (s, 2 H), 9.88 (s, 1 H), 9.2 (br s, 1 H), 8.43 (d, 1 H, J=7.0 Hz), 8.02 (m, 3 H), 7.92 (m, 1 H), 7.47 (m, 2 H), 7.41 (m, 2 H), 7.36 (s, 1 H), 7.24 (m, 1 H), 7.19 (m, 1 H), 7.15 (m, 1 H), 7.12 (m, 3 H), 7.01 (m, 2 H), 6.90 (m, 3 H), 6.83 (m, 1 H), 4.46 (q, 1 H, J=5.5 Hz), 3.94 (s, 3 H), 3.79 (m, 9 H), 3.75 (m, 6 H), 3.32 (m, 4 H), 3.05 (m, 2 H), 2.94 (m, 2 H), 2.68 (d, 6H, J=4.0 Hz), 2.28 (t, 2 H, J=6.3 Hz), 1.93 (q, 2 H, J=6.1 Hz), 1.66 (quintet, 2 H, J=6.0 Hz), 1.18 (s, 3 H); MALDI-TOF-MS (monoisotopic), 1208.5 (1208.5 calc. for $C_{57}H_{68}F_3N_{17}O_{10}$).

D. ImPyPy-(R)$^{(S)MTPA}$γ-PyPyPy-β-Dp 1-R,S

ImPyPy-(R)$^{(S)MTPA}$γ-PyPyPy-β-Dp was prepared from (S)-α-methoxy-α(trifluoromethyl)phenylacetic acid as described for 1-R,R (5 mg, 45% recovery). $^1$H NMR (DMSO-$d_6$) δ10.47 (s, 1 H), 10.08 (s, 1 H), 9.92 (s, 2 H), 9.88 (s, 1 H), 9.2 (br s, 1 H), 8.43 (d, 1 H, J=6.9 Hz), 8.02 (m, 3 H), 7.46 (m, 2 H), 7.40 (m, 2 H), 7.36 (s, 1 H), 7.23 (m, 1 H), 7.19 (m, 1 H), 7.14 (m, 1 H), 7.12 (m, 3 H), 7.01 (m, 2 H), 6.87 (m, 3 H), 6.83 (m, 1 H), 4.44 (q, 1 H, J=6.5 Hz), 3.94 (s, 3 H), 3.79 (m, 9 H), 3.75 (m, 6 H), 3.28 (m, 4 H), 3.06 (m, 4 H), 2.94 (m, 2 H), 2.69 (d, 6H, J=4.5 Hz), 2.28 (t, 2 H, J=6.5 Hz), 1.93 (q, 2 H, J=6.1 Hz), 1.66 (quintet, 2 H, J=6.0 Hz), 1.18 (s, 3 H); MALDI-TOF-MS (monoisotopic), 1209.0 (1208.5 calc. for $C_{57}H_{68}F_3N_{17}O_{10}$).

E. ImPyPy-(S)$^{H_2N}$γ-PyPyPy-β-Dp (1-S)

ImPyPy-(S)$^{H_2N}$γ-PyPyPy-β-Dp was prepared as described for 1-R (23 mg, 49% recovery). [α]$^{20}_D$–14.2 (c 0.04, $H_2O$); $^1$H NMR (DMSO-$d_6$) identical to 1-R; MALDI-TOF-MS (monoisotopic), 992.5 (992.5 calc. for $C_{47}H_{62}N_{17}O_8$). FIG. 2B illustrates a binding model for the ImPyPy-(S)$^{H_2N}$γ-PyPyPy-β-Dp (1-S) polyamide to the DNA seuqnce 5'-TGTTA-3'.

F. ImPyPy-(R)$^{H_2N}$γ-PyPyPy-β-EtOH (2-R)

A sample of ImPyPy-(R)$^{H_2N}$γ-PyPyPy-β-Pam-resin (240 mg, 0.18 mmol/gram) was treated with neat ethanolamine (2 mL) and heated (55° C.) with periodic agitation for 16 h. The reaction mixture was then filtered to remove resin, 0.1% (wt/v) TFA added (6 mL) and the resulting solution purified by reversed phase HPLC to provide ImPyPy-(R)$^{H_2N}$γ-PyPyPy-β-EtOH as a white powder upon lyophilization of the appropriate fractions (21 mg, 46% recovery). [α]$^{20}_D$+ 18.6 (c 0.04, $H_2O$); UV ($H_2O$) λ$_{max}$ 246, 310 (50,000); $^1$H NMR (DMSO-$d_6$) δ10.55 (s, 1 H), 10.48 (s, 1 H), 9.97 (s, 1 H), 9.94 (s, 1 H), 9.89 (s, 1 H), 8.24 (m, 4 H), 8.00 (t, 1 H, J=4.1 Hz), 7.89 (t, 1 H, J=5.8 Hz), 7.38 (s, 1 H), 7.25 (d, 1 H, J=1.6 Hz), 7.22 (d, 1 H, J=1.6 Hz), 7.21 (d, 1 H, J=1.5 Hz), 7.16 (m, 2 H), 7.14 (d, 1 H, J=1.6 Hz), 7.03 (d, 1 H, J=1.7 Hz), 6.99 (d, 1 H, J=1.4 Hz), 6.95 (d, 1 H, J=1.6 Hz), 6.91 (d, 1 H, J=1.5 Hz), 6.78 (d, 1 H, J=1.5 Hz), 5.33 (m, 1 H), 3.95 (s, 3 H), 3.83 (s, 3 H), 3.81 (m, 6 H), 3.79 (s, 3 H), 3.76 (s, 3 H), 3.37 (q, 2 H, J=6.2 Hz), 3.07 (q, 2 H, J=5.9 Hz), 2.29 (t, 2 H, J=7.1 Hz), 1.93 (q, 2 H, J=5.8 Hz), 1.20 (m, 4 H); MALDI-TOF-MS (monoisotopic), 951.4 (951.4 calc. for $C_{44}H_{55}N_{16}O_9$). The 2-R polyamide is shown in FIG. 3.

G. ImPyPy-(R)$^{Ac}$γ-PyPyPy-β-Dp (3-R)

A sample of ImPyPy-(R)$^{H_2N}$γ-PyPyPy-β-Dp (4 mg) in DMSO (1 mL) was treated with a solution of acetic anhydride (1 mL) and DIEA (1 mL) in DMF (1 ml) and heated (55° C.) with periodic agitation for 30 min. Residual acetic anhydride was hydrolyzed (0.1 M NaOH, 1 mL, 55° C., 10 min.), 0.1% (wt/v) TFA was added (6 mL) and the resulting solution purified by reversed phase HPLC to provide ImPyPy-(R)$^{H_2N}$γ-PyPyPy-β-Dp is recovered as a white powder upon lyophilization of the appropriate fractions (2 mg, 50% recovery). [α]$^{20}_D$+20.5 (c 0.06, $H_2O$); UV ($H_2O$) λ$_{max}$ 242, 304 (50,000); $^1$H NMR (DMSO-$d_6$) δ10.49 (s, 1 H), 10.06 (s, 1 H), 9.94 (m, 2 H), 9.00 (s, 1 H), 9.4 (br s, 1 H), 8.21 (d, 1 H, J=7.8 Hz), 8.06 (m, 2 H), 8.00 (t, 1 H, J=6.2 Hz), 7.39 (s, 1 H), 7.27 (d, 1 H, J=1.7 Hz), 7.21 (d, 1 H, J=1.6 Hz), 7.18 (m, 2 H), 7.14 (m, 2 H), 7.03 (m, 2 H), 6.90 (d, 1 H, J=1.6 Hz), 6.86 (m, 2 H), 4.43 (q, 1 H, J=7.5 Hz), 3.96 (s, 3 H), 3.82 (m, 9 H), 3.73 (m, 6 H), 3.37 (q, 2 H, J=5.8 Hz), 3.11 (q, 2 H, J=6.9 Hz), 2.98 (q, 2 H, J=5.4 Hz), 2.79 (q, 2 H, J=5.3 Hz), 2.71 (d, 6 H, J=4.7 Hz), 2.33 (t, 2 H, J=6.2 Hz), 1.97 (s, 3 H), 1.70 (quintet, 2 H, J=6.0 Hz) MALDI-TOF-MS (average), 1035.1 (1035.2 calc. for M+H). The 3-R polyamide is shown in FIG. 3.

H. ImPyPy-(S)$^{Ac}$γ-PyPyPy-β-Dp (3-S)

ImPyPy-(S)$^{Ac}$γ-PyPyPy-β-Dp was prepared as described for 3-R. (2 mg, 50% recovery). [α]$^{20}_D$–16.4 (c 0.07, $H_2O$); $^1$H NMR (DMSO-$d_6$) is identical to 3-R; MALDI-TOF-MS (monoisotopic), 1034.6 (1034.5 calc. for $C_{49}H_{64}N_{17}O_9$).

I. ImPyPy-(R)$^{Boc}$γ-PyPyPy-β-Dp-NH$_2$ (4-R-Boc-NH$_2$)

A sample of ImPyPy-(R)$^{H_2N}$γ-PyPyPy-β-Pam-resin (300 mg, 0.18 mmol/gram). Resin substitution can be calculated as $L_{new}$(mmol/g)=$L_{old}$/(1+$L_{old}$($W_{new}$−$W_{old}$)×10$^{-3}$), where L is the loading (mmol of amine per gram of resin), and W is the weight (gmol$^{-1}$) of the growing polyamide attached to the resin. see: Barlos, et al. *Int. J. Peptide Protein Res.* 1991, 37, 513.) was treated a solution of Boc-anhydride (500 mg) and DIEA (1 mL) in DMF (4 ml) and heated (55° C.) with periodic agitation for 30 min. ImPyPy-(R)$^{Boc}$γ-PyPyPy-β-Pam-resin was isolated by filtration, and washed sequentially with an excess of DMF, DCM, MeOH, and ethyl ether and the dried in vacuo. A sample of ImPyPy-(R)$^{Boc}$γ-PyPyPy-β-Pam-resin (240 mg, 0.18 mmol/gram) was treated with neat 3,3'-diamino-N-methyldipropylamine (2 mL) and heated (55° C.) with periodic agitation for 16 h. The reaction mixture was then filtered to remove resin, 0.1% (wt/v) TFA added (6 mL) and the resulting solution purified by reversed phase HPLC to provide ImPyPy-(R)$^{Boc}$γ-PyPyPy-β-Dp-NH$_2$ as a white powder upon lyophilization of the appropriate fractions (18 mg, 36% recovery); $[α]^{20}{}_D$–30 (c 0.05, H$_2$O); UV (H$_2$O) λ$_{max}$ 240, 306 (50,000); $^1$H NMR (DMSO-d$_6$) δ10.59 (s, 1 H), 10.16 (s, 1 H), 10.04 (m, 2 H), 10.00 (s, 1 H), 9.4 (br s, 1 H), 8.31 (d, 1 H, J=7.8 Hz), 8.16 (m, 2 H), 8.10 (t, 1 H, J=6.2 Hz), 7.89 (t, 1 H, J=5.8 Hz), 7.49 (s, 1 H), 7.37 (d, 1 H, J=1.7 Hz), 7.22 (d, 1 H, J=1.6 Hz), 7.21 (d, 1 H, J=1.5 Hz), 7.16 (m, 2 H), 7.14 (d, 1 H, J=1.6 Hz), 7.03 (d, 1 H, J=1.7 Hz), 6.99 (d, 1 H, J=1.4 Hz), 6.95 (d, 1 H, J=1.6 Hz), 6.91 (d, 1 H, J=1.5 Hz), 6.78 (d, 1 H, J=1.5 Hz), 5.33 (m, 1 H), 3.95 (s, 3 H), 3.83 (s, 3 H), 3.81 (m, 6 H), 3.79 (s, 3 H), 3.76 (s, 3 H), 3.37 (q, 2 H, J=6.2 Hz), 3.07 (q, 2 H, J=5.9 Hz), 2.29 (t, 2 H, J=7.1 Hz), 1.93 (q, 2 H, J=5.8 Hz), 1.20 (m, 4 H); MALDI-TOF-MS (monoisotopic), 1135.3 (1135.6 calc. for C$_{54}$H$_{75}$N$_{18}$O$_{10}$).

J. ImPyPy-(S)$^{Boc}$γ-PyPyPy-β-Dp-NH$_2$ (4-S-Boc-NH$_2$)

ImPyPy-(S)$^{Boc}$γ-PyPyPy-β-Dp-NH$_2$ was prepared as described for 4-R. (16 mg, 32% recovery). $[α]^{20}{}_D$–30 (c 0.05, H$_2$O); $^1$H NMR (DMSO-d$_6$) is identical to 4-R-Boc-NH$_2$; MALDI-TOF-MS (monoisotopic), 1135.4 (1135.6 calc. for C$_{54}$H$_{75}$N$_{18}$O$_{10}$).

K. ImPyPy-(R)$^{Boc}$γ-PyPyPy-β-Dp-EDTA (4-R-Boc)

Excess EDTA-dianhydride (50 mg) was dissolved in DMSO/NMP (1 mL) and DIEA (1 mL) by heating at 55° C. for 5 min. The dianhydride solution was added to ImPyPy$^{Boc}$γ-PyPyPy-β-Dp-NH$_2$ (10.4 mg, 10 μmol) dissolved in DMSO (750 μL). The mixture was heated (55° C., 25 min.) and the remaining EDTA-anhydride hydrolyzed (0.1M NaOH, 3 mL, 55° C., 10 min). Aqueous TFA (0.1% wt/v) was added to adjust the total volume to 8 mL and the solution purified directly by reversed phase HPLC to provide ImPyPy-(R)$^{Boc}$γ-PyPyPy-β-Dp-EDTA (4-R-Boc) as a white powder upon lyophilization of the appropriate fractions (4 mg, 40% recovery). MALDI-TOF-MS (monoisotopic), 1409.6 (1409.7 calc. for C$_{64}$H$_{89}$N$_{20}$O$_{17}$).

L. ImPyPy-(S)$^{Boc}$γ-PyPyPy-β-Dp-EDTA (4-S-Boc)

ImPyPy-(S)$^{Boc}$γ-PyPyPy-β-Dp-NH$_2$ (12.0 mg, 12 μmol) was converted to 4-S-Boc as described for 4-R-Boc (4 mg, 33% recovery). MALDI-TOF-MS (monoisotopic), 1409.7 (1409.7 calc. for C$_{64}$H$_{89}$N$_{20}$O$_{17}$).

M. ImPyPy-(R)$^{H_2N}$γ-PyPyPy-β-Dp-EDTA (4-R)

A sample of ImPyPy-(R)$^{Boc}$γ-PyPyPy-β-Dp-EDTA (2.1 mg) in DMSO (750 μL) was placed in a 50 ml flask and treated with TFA (15 mL, 22° C., 2 h). Excess TFA was removed in vacuo, water added (6 mL) and the resulting solution purified by reversed phase HPLC to provide ImPyPy-(R)$^{H_2N}$γ-PyPyPy-β-Dp-EDTA as a white powder upon lyophilization of the appropriate fractions (1.3 mg, 50% recovery). MALDI-TOF-MS (monoisotopic), 1309.5 (1309.6 calc. for C$_{59}$H$_{81}$N$_{20}$O$_{15}$).

N. ImPyPy-(S)$^{H_2N}$γ-PyPyPy-β-Dp-EDTA (4-S)

ImPyPy-(S)$^{Boc}$γ-PyPyPy-β-Dp-EDTA (3.0 mg) was converted to 4-S as described for 4-R (1 mg, 33% recovery). MALDI-TOF-MS (monoisotopic), 1309.5 (1309.6 calc. for C$_{59}$H$_{81}$N$_{20}$O$_{15}$).

O. ImPyPy-(R)$^{EDTA}$γ-PyPyPy-β-Dp (5-R)

Excess EDTA-dianhydride (50 mg) was dissolved in DMSO/NMP (1 mL) and DIEA (1 mL) by heating at 55° C. for 5 min. The dianhydride solution was added to ImPyPy-(R)$^{H_2N}$γ-PyPyPy-β-Dp (1.0 mg, 1 μmol) dissolved in DMSO (750 μL). The mixture was heated (55° C., 25 min.) and remaining EDTA-anhydride was hydrolyzed (0.1M NaOH, 3 mL, 55° C., 10 min.). Aqueous TFA (0.1% wt/v) was added to adjust the total volume to 8 mL and the solution purified directly by reversed phase HPLC to provide 5-R as a white powder upon lyophilization of the appropriate fractions (0.6 mg, 60% recovery). MALDI-TOF-MS (monoisotopic), 1266.4 (1266.6 calc. for C$_{57}$H$_{76}$N$_{19}$O$_{15}$). The 5-R polyamide is shown in FIG. 3.

P. ImPyPy-(S)$^{EDTA}$γ-PyPyPy-β-Dp (5-S)

ImPyPy-(S)$^{EDTA}$γ-PyPyPy-β-Dp was prepared from 1-S as described for 5-R (6.8 mg, 16% recovery). MALDI-TOF-MS (monoisotopic), 1266.5 (1266.6 calc. for C$_{57}$H$_{76}$N$_{19}$O$_{15}$).

Example 2

Binding Site Size and Location by MPE•Fe(II) Footprinting

A. Preparation of 3'- and 5'-End-Labeled Restriction Fragments

The plasmid pMM5 was linearized with EcoRI and BsrBI, then treated with the Sequenase enzyme, deoxyadenosine 5'-[γ-$^{32}$P]triphosphate and thymidine 5'-[γ$^{32}$P] triphosphate for 3' labeling. Alternatively, pMM5 was linearized with EcoRI, treated with calf alkaline phosphatase, and then 5' labeled with T4 polynucleotide kinase and deoxyadenosine 5'-[γ$^{32}$P]triphosphate. The 5' labeled fragment was then digested with BsrBI. The labeled fragment (3' or 5') was loaded onto a 6% non-denaturing polyacrylamide gel, and the desired 135 base pair band was visualized by autoradiography and isolated. Chemical sequencing reactions were performed according to published methods (Iverson, et al. *Nucl. Acids Res.* 1987, 15, 7823; Maxam, et al. *Methods Enzymol.* 1980, 65, 499).

B. MPE•Fe(II) Footprinting

All reactions were carried out in a volume of 40 μL. A polyamide stock solution or water (for reference lanes) was added to an assay buffer where the final concentrations were: 25 mM Tris-acetate buffer (pH 7.0), 10 mM NaCl, 100 μM/base pair calf thymus DNA, and 30 kcpm 3'- or 5'-radiolabeled DNA. The solutions were allowed to equilibrate for 4 hours. A fresh 50 μM MPE•Fe(II) solution was prepared from 100 μL of a 100 μM MPE solution and 100 μL of a 100 μM ferrous ammonium sulfate (Fe(NH$_4$)$_2$(SO$_4$)$_2$.6H$_2$O) solution. MPE•Fe(II) solution (5 μM) was added to the equilibrated DNA, and the reactions were allowed to equilibrate for 5 minutes. Cleavage was initiated by the addition of dithiothreitol (5 mM) and allowed to proceed for 14 min. Reactions were stopped by ethanol precipitation, resuspended in 100 mM tris-borate-EDTA/ 80% formamide loading buffer, denatured at 85° C. for 6 min, and a 5 μL sample (~15 kcpm) was immediately loaded onto an 8% denaturing polyacrylamide gel (5% crosslink, 7 M urea) at 2000 V.

C. Results

MPE•Fe(II) footprinting (Van Dyke, et al. *Proc. Natl. Acad. Sci. U.S.A.* 1982, 79, 5470; Van Dyke, et al. *Science*

Figure 5A:
FIGS. 5A–5D. Results of MPE•Fe(II) footprinting using improved polyamides.
Figure 5B:
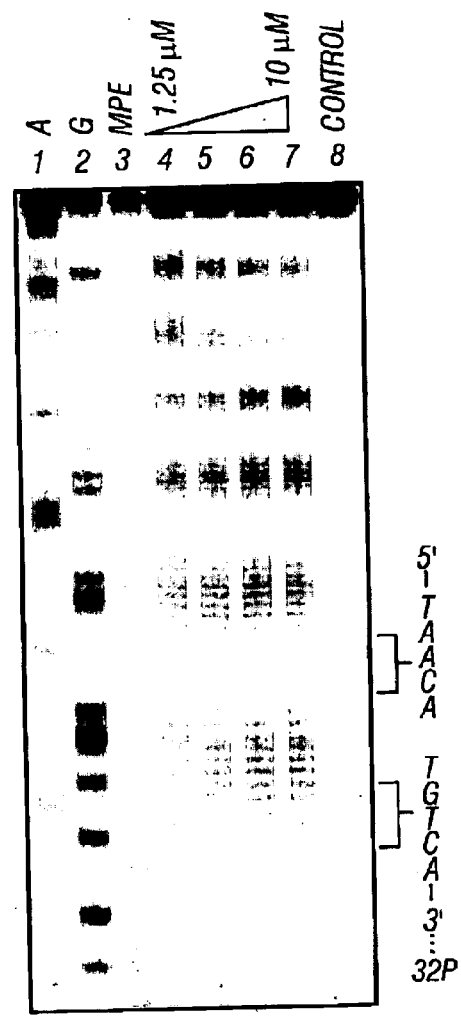
Figure 5C:
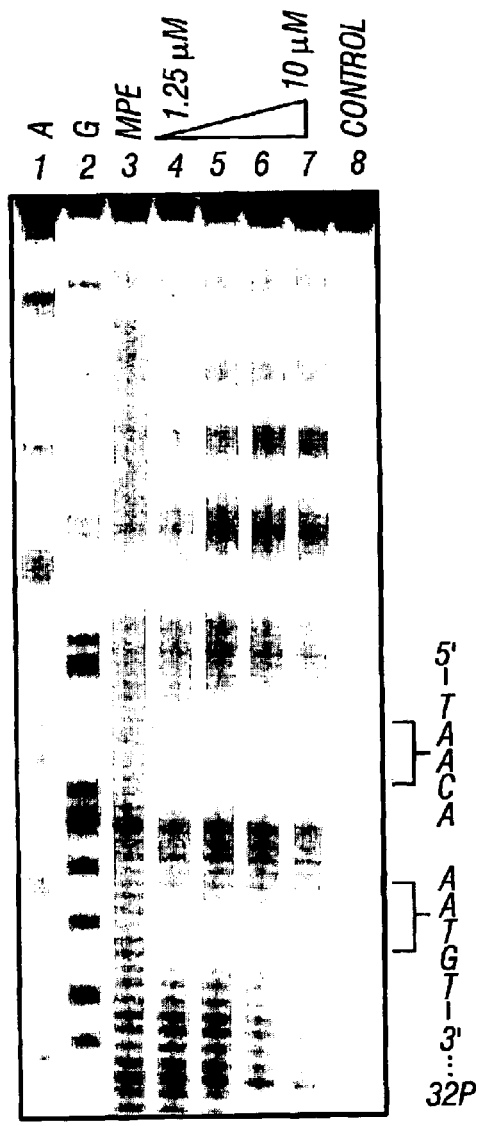
Figure 5D:
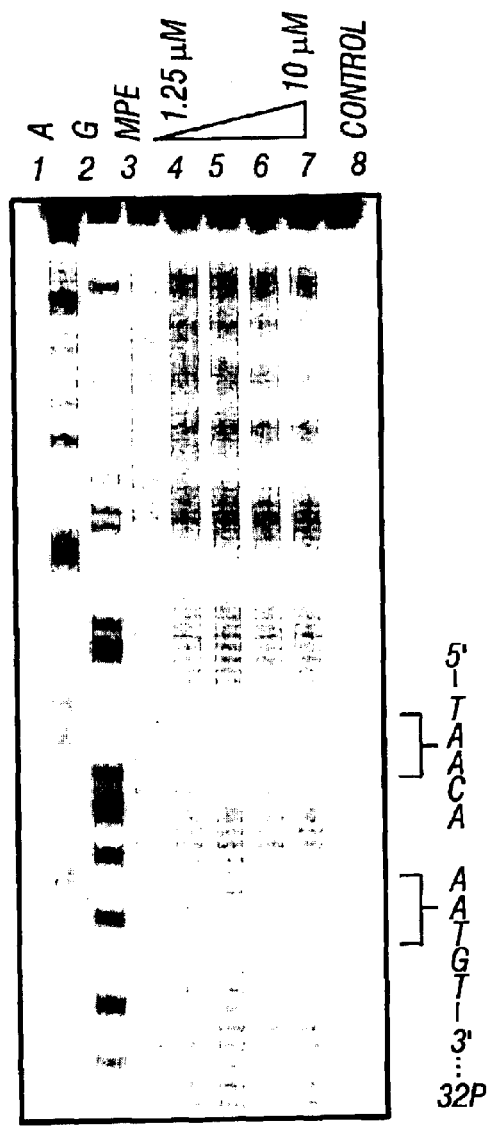
Figure 6:
FIG. 6. Binding patterns of certain improved polyamides to a 135 bp restriction fragment comprising SEQ ID Nos. 19 and 20.
Figure 7A:
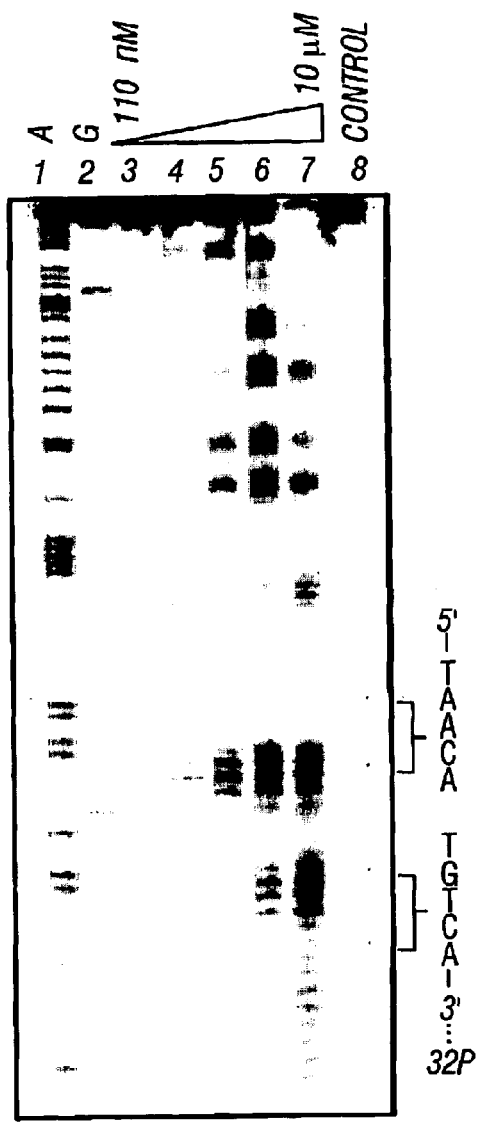
FIGS. 7A–7D. Affinity cleavage experiments using improved polyamides and a 3'-$^{32}$P-labeled 135 bp restriction fragment.
Figure 7B:
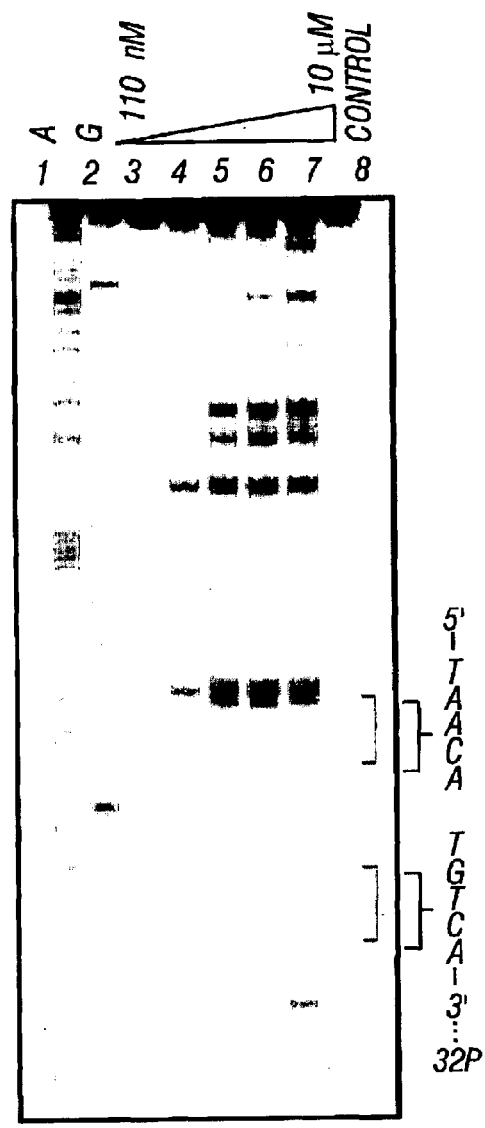
Figure 7C:
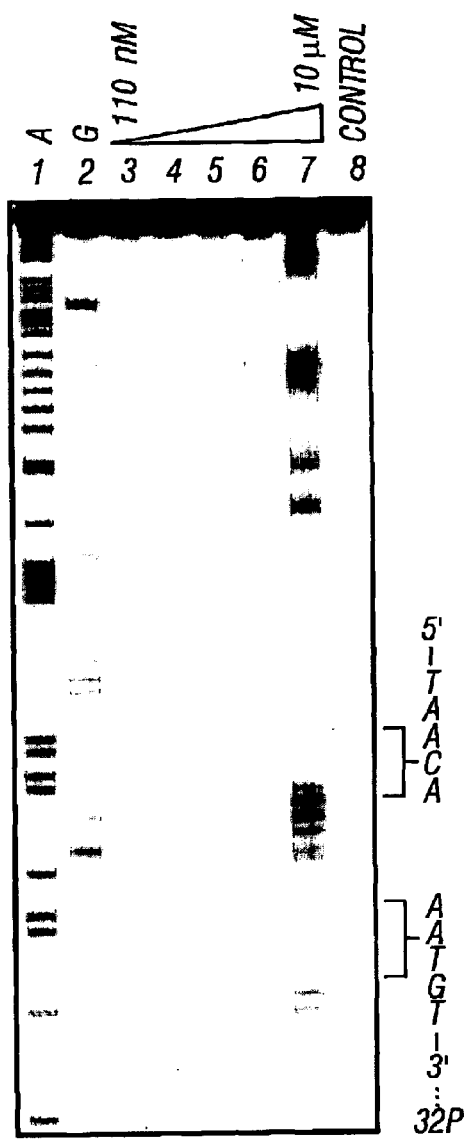
Figure 7D:
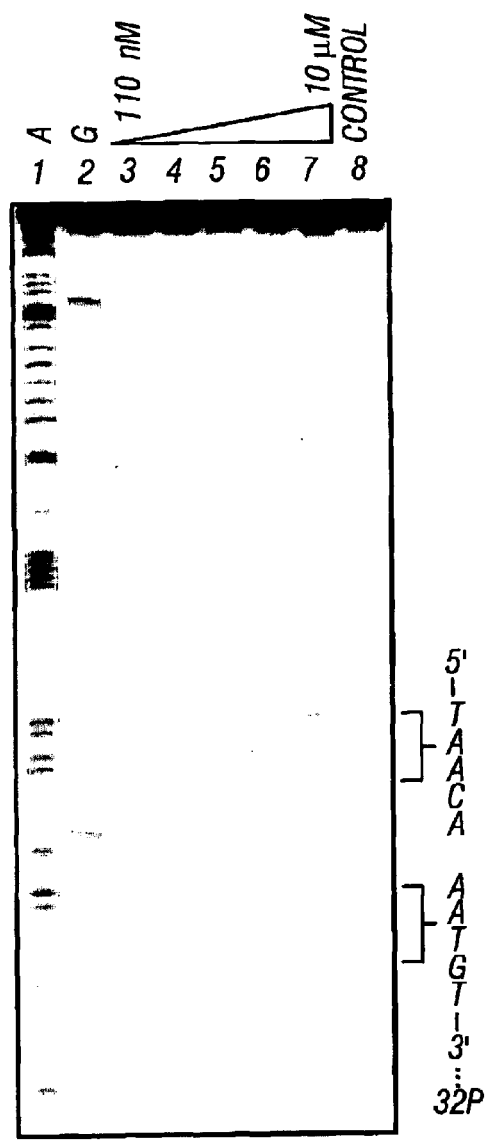

1984, 225, 1122) on 3'- and 5'-$^{32}$P end-labeled 135 base pair restriction fragments reveals that the polyamides, each at 1 μM concentration, bind to the 5'-TGTTA-3' match site (25 mM Tris-acetate, 10 mM NaCl, 100 μM/base pair calf thymus DNA, pH 7.0 and 22° C.) (FIGS. 5 and 6). Compounds 1-R and 3-R each at 1.25 M, protect both the cognate 5'-TGTAA-3' site and the single base pair mismatch sequence 5'-TGTCA-3'. Remarkably, binding sequence preferences vary for the polyamides depending on the stereochemistry of the amine substituent. At 1.25 μM and 2.5 M concentration respectively, polyamides 1-S and 3-S bind a 5'-ACATT-3' reverse orientation match site in addition to the target match site 5'-TGTTA-3'. The sizes of the asymmetrically 3'-shifted footprint cleavage protection patterns for the polyamides are consistent with 5 base pair binding sites.

Example 3

Binding Orientation Determination by Affinity Cleaving

Affinity cleavage experiments (Taylor, et al. *Tetrahedron* 1984, 40, 457; Dervan, P. B. *Science* 1986, 232, 464) using hairpin polyamides modified with EDTA•Fe(II) at either the C-terminus or on the γ-turn, were used to determine polyamide binding orientation and stoichiometry. All reactions were carried out in a volume of 40 μL. A polyamide stock solution or water (for reference lanes) was added to an assay buffer where the final concentrations were: 25 mM Tris-acetate buffer (pH 7.0), 20 mM NaCl, 100 μM/base pair calf thymus DNA, and 20 kcpm 3'- or 5'-radiolabeled DNA. The solutions were allowed to equilibrate for 8 hours. A fresh solution of ferrous ammonium sulfate (Fe(NH$_4$)$_2$(SO$_4$)$_2$.6H$_2$O (10 μM) was added to the equilibrated DNA, and the reactions were allowed to eqilibrate for 15 minutes. Cleavage was initiated by the addition of dithiothreitol (10 mM) and allowed to proceed for 30 min. Reactions were stopped by ethanol precipitation, resuspended in 100 mM tris-borate-EDTA/80% formamide loading buffer, denatured at 85° C. for 6 min, and the entire sample was immediately loaded onto an 8% denaturing polyacrylamide gel (5% crosslink, 7 M urea) at 2000 V.

Figure 8:
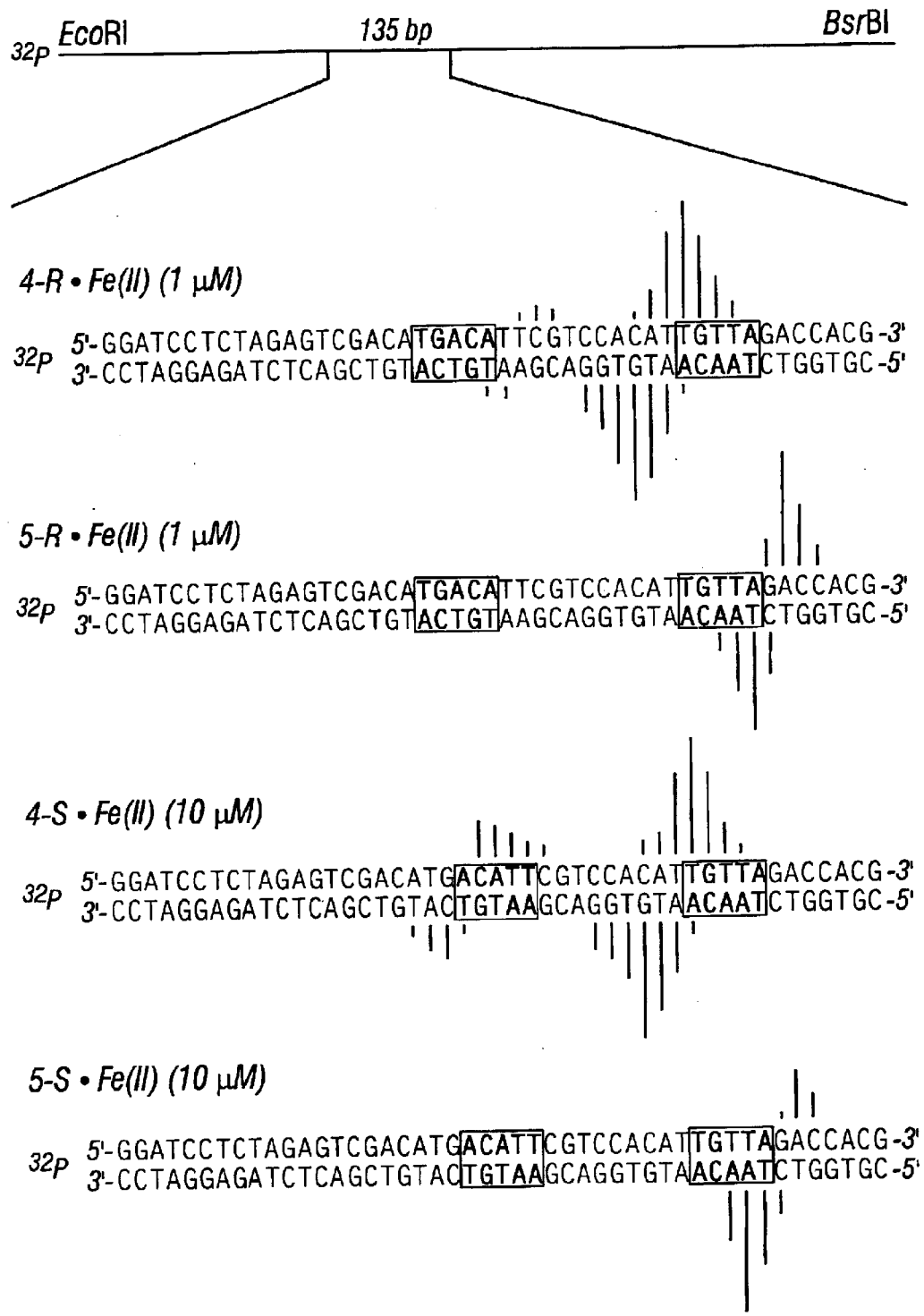
FIG. 8. Affinity cleavage patterns of certain improved polyamides at 1 μM concentration and 10 μM concentrations for 135 bp fragments comprising SEQ ID NOS 19 and 20.
Figure 9A:
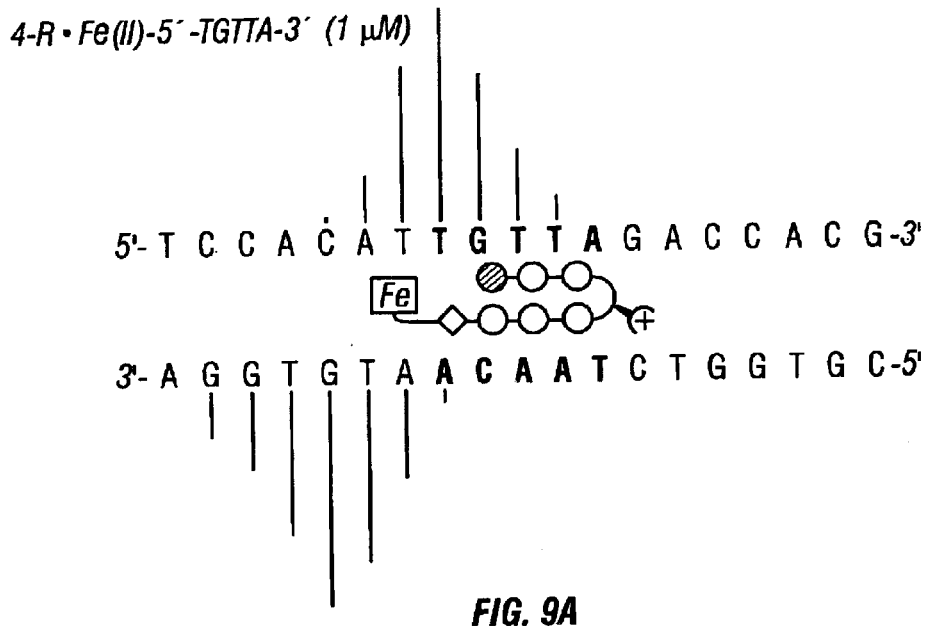
FIG. 9. Panels A–C represent affinity cleavage patterns of certain improved polyamides using SEQ ID NOS. 21, 22, 23, and 24.
Figure 9B:
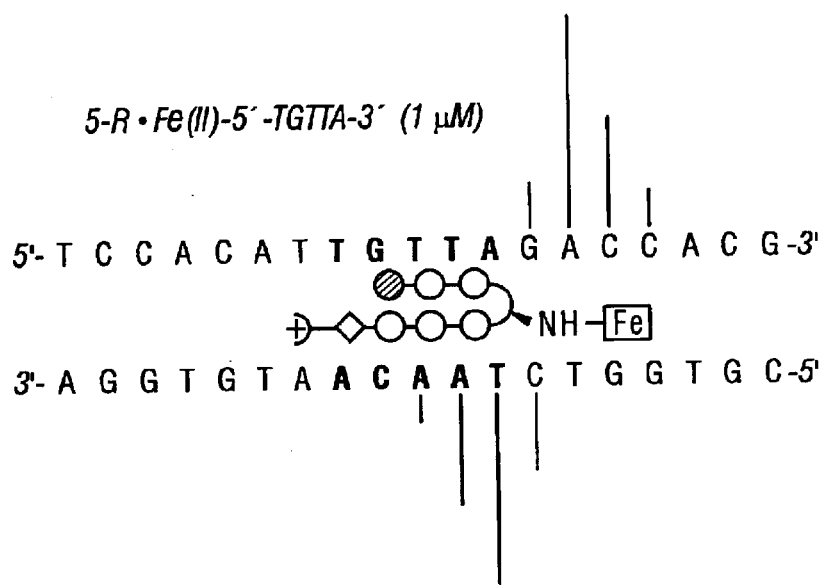
Figure 9C:
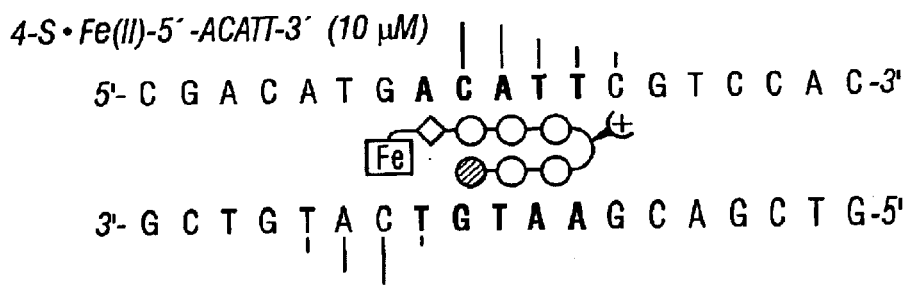

Affinity cleavage experiments were performed on the same 3'- and 5'-$^{32}$P end-labeled 135 base pair restriction fragment (25 mM Tris-acetate, 10 mM NaCl, 100 μM/base pair calf thymus DNA, pH 7.0 and 22° C.). The observed cleavage patterns for ImPyPy-(R)$^{H_2N}$γ-PyPyPy-β-Dp-EDTA•Fe(II) (4-R•Fe(II)), ImPyPy-(R)$^{EDTA•Fe(II)}$γ-PyPyPy-β-Dp (5-R•Fe(II)), ImPyPy-(S)$^{H_2N}$γ-PyPyPy-β-Dp-EDTA•Fe(II) (4-S•Fe(II)), ImPyPy-(S)$^{EDTA•Fe(II)}$γ-PyPyPy-β-Dp (5-S•Fe(II)) (FIGS. 7, 8 and 9) are in all cases 3'-shifted, consistent with minor groove occupancy. In the presence of 3.3 μM of 4-R•Fe(II) and 10 μM 4-S•Fe(II) which have an EDTA•Fe(II) moiety at the C-terminus, a single cleavage locus proximal to the 5' side of the 5'-TGTTA-3' match sequence is revealed. In the presence of 3.3 μM 5-R•Fe(II) and 10 μM 5-S•Fe(II) which have an EDTA•Fe(II) moiety appended to the γ-turn, a single cleavage locus is revealed proximal to the 3' side of the 5'-TGTTA-3' match sequence. Cleavage loci are more concise for the γ-turn EDTA•Fe(II) placement relative to carboxy terminal placement, consistent with the shorter tether. Cleavage loci are observed at both the 5' and 3' side of the 5'-TGTCA-3' single base pair mismatch site in the presence of 10 μM of 4-R•Fe(II). The cleavage patterns observed at the 3' side of the site is approximately 3-fold more intense than cleavage at the 5'-side. For polyamide 4-S•Fe(II) at 10 μM concentration, a single cleavage locus is revealed proximal to the 5' side of the 5'-ACATT-3' reverse orientation match site.

Example 4

Energetics by Quantitative DNase I Footprinting

A. DNase I Footprinting

All reactions were carried out in a volume of 400 μL. Carrier DNA was not used in these reactions until after DNase I cleavage. A polyamide stock solution or water (for reference lanes) was added to an assay buffer where the final concentrations were: 10 mM Tris•HCl buffer (pH 7.0), 10 mM KCl, 10 mM MgCl$_2$, 5 mM CaCl$_2$, and 30 kcpm 3'-radiolabeled DNA. The solutions were allowed to equilibrate for a minimum of 12 hours at 22° C. Cleavage was initiated by the addition of 10 μL of a DNase I stock solution (diluted with 1 mM DTT to give a stock concentration of 1.875 u/mL) and was allowed to proceed for 7 min at 22° C. The reactions were stopped by adding 50 μL of a solution containing 2.25 M NaCl, 150 mM EDTA, 0.6 mg/mL glycogen, and 30 μM base-pair calf thymus DNA, and then ethanol precipitated. The cleavage products were resuspended in 100 mM tris-borate-EDTA/80% formamide loading buffer, denatured at 85° C. for 6 min, and immediately loaded onto an 8% denaturing polyacrylamide gel (5% crosslink, 7 M urea) at 2000 V for 1 hour. The gels were dried under vacuum at 80° C., then quantitated using storage phosphor technology.

Equilibrium association constants were determined as previously described (Mrksich, et al. *J. Am. Chem. Soc.* 1994, 116, 7983). The data were analyzed by performing volume integrations of the 5'-TGTTA-3' and 5'-TGACA-3 sites and a reference site. The apparent DNA target site saturation, θ$_{app}$, was calculated for each concentration of polyamide using the following equation:

$$\theta_{app} = 1 - \frac{I_{tot}/I_{ref}}{I_{tot}°/I_{ref}°} \qquad (1)$$

where I$_{tot}$ and I$_{ref}$ are the integrated volumes of the target and reference sites, respectively, and I$_{tot}°$ and I$_{ref}°$ correspond to those values for a DNase I control lane to which no polyamide has been added. The ([L]$_{tot}$, θ$_{app}$) data points were fit to a Langmuir binding isotherm (eq 2, n=1 for polyamides 1–3, n=2 for polyamides 4 and 5) by minimizing the difference between θ$_{app}$ and θ$_{fit}$, using the modified Hill equation:

$$\theta_{fit} = \theta_{min} + (\theta_{max} - \theta_{min})\frac{K_a^n[L]_{tot}^n}{1 + K_a^n[L]_{tot}^n} \qquad (2)$$

where [L]$_{tot}$ corresponds to the total polyamide concentration, K$_1$ corresponds to the equilibrium association constant, and θ$_{min}$ and θ$_{max}$ represent the experimentally determined site saturation values when the site is unoccupied or saturated, respectively. Data were fit using a non-linear least-squares fitting procedure of KaleidaGraph software (version 2.1, Abelbeck software) with K$_a$, θ$_{max}$, and θ$_{min}$ as the adjustable parameters. All acceptable fits had a correlation coefficient of R>0.97. At least three sets of acceptable data were used in determining each association constant. All lanes from each gel were used unless visual inspection revealed a data point to be obviously flawed relative to neighboring points. The data were normalized using the following equation:

$$\theta_{norm} = \frac{\theta_{app} - \theta_{min}}{\theta_{max} - \theta_{min}} \quad (3)$$

Photostimulable storage phosphorimaging plates (Kodak Storage Phosphor Screen S0230 obtained from Molecular Dynamics) were pressed flat against gel samples and exposed in the dark at 22° C. for 12–20 h. A Molecular Dynamics 400S PhophorImager was used to obtain all data from the storage screens. The data were analyzed by performing volume integrations of all bands using the ImageQuant v. 3.2.

B. Results

Figure 10A:
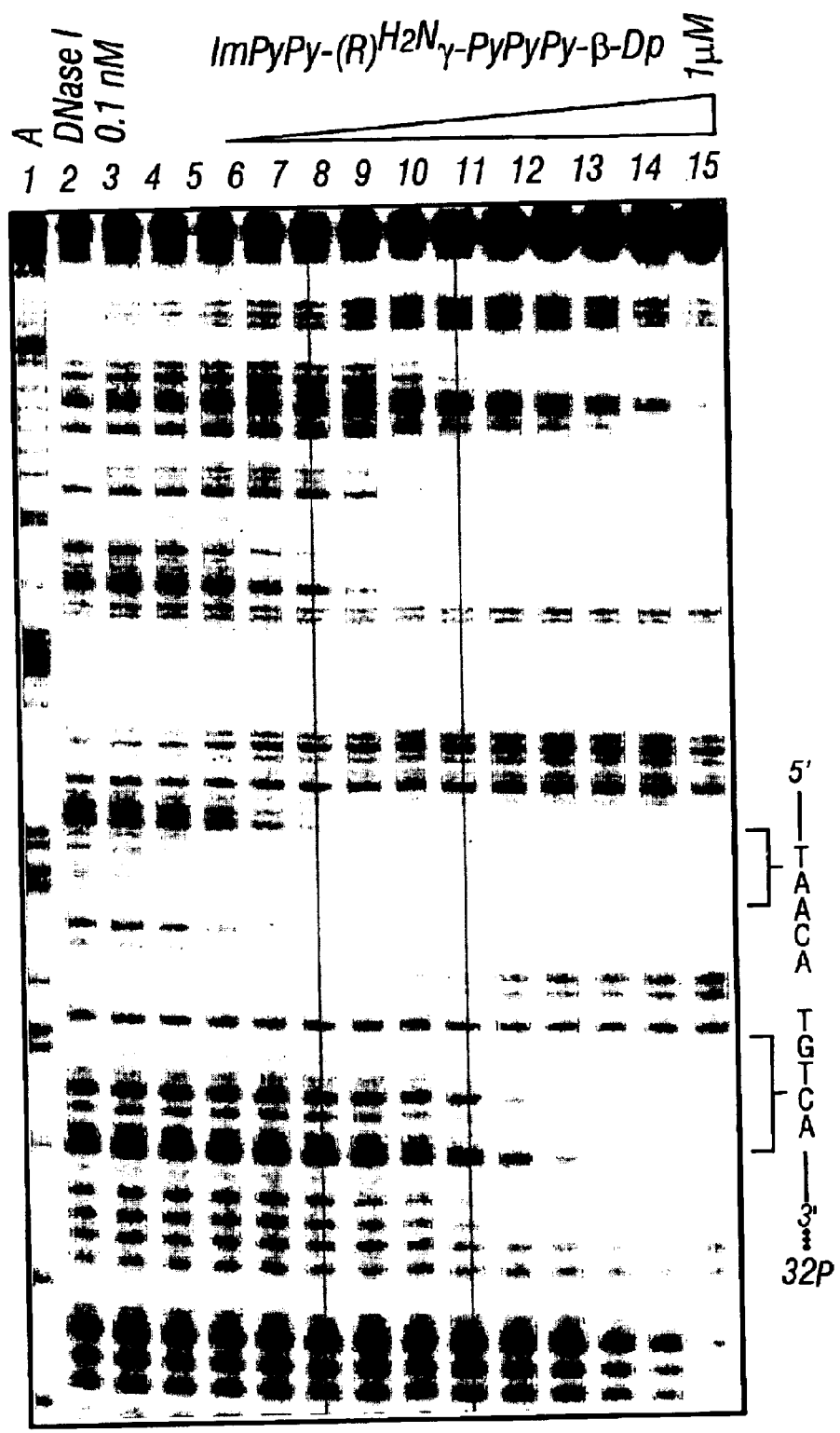
FIGS. 10A–10B. Quantitative DNase I footprint titration of certain improved polyamides.
Figure 10B:
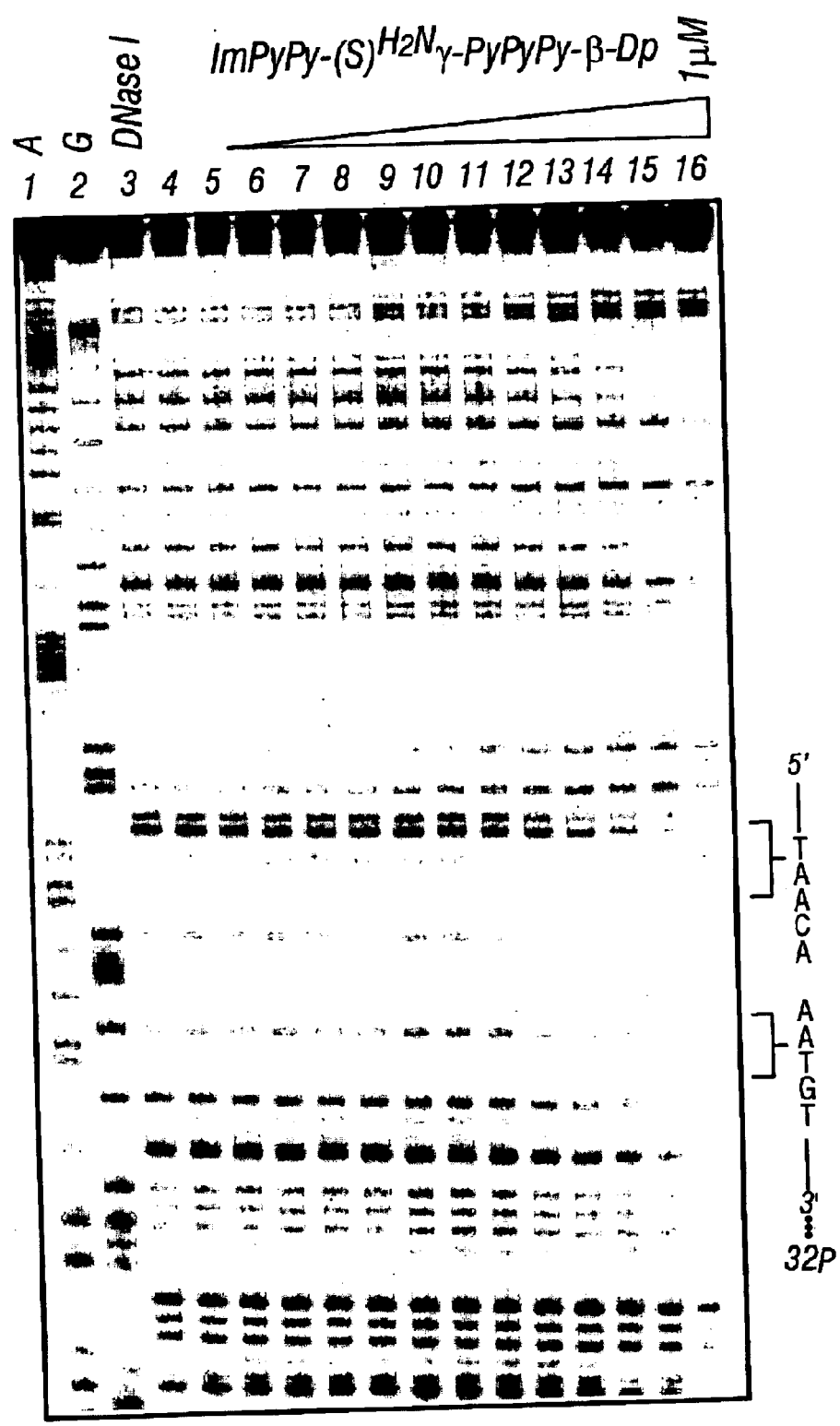
Figure 11:
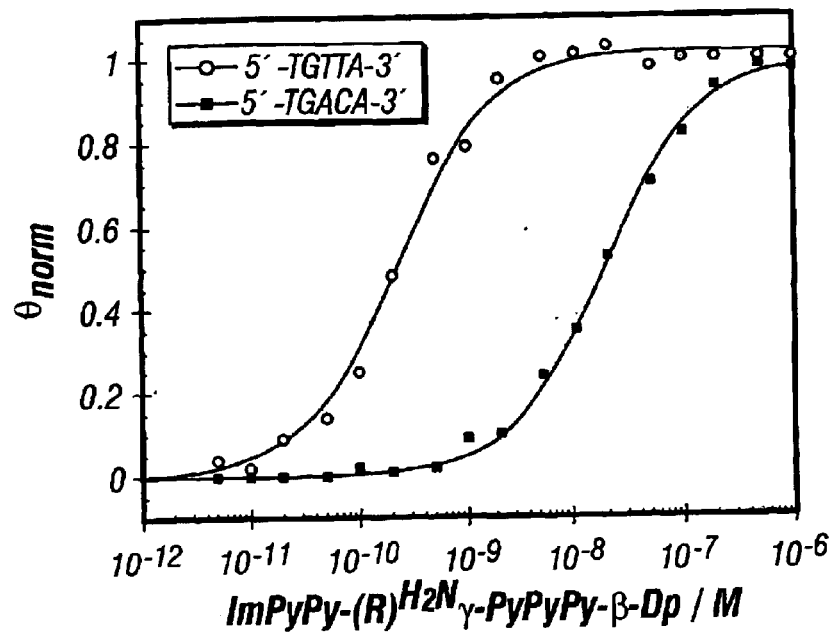
FIG. 11. Quantitative DNase I footprint titrations of ImPyPy-(R)$^{H_2N}$γ-PyPyPy-β-Dp.

Quantitative DNase I footprint titrations (Brenowitz, et al., *Methods Enzymol.* 1986, 130, 132; Brenowitz, et al. *Proc. Natl. Acad. Sci. U.S.A.* 1986, 83, 8462; Senear, et al. *Biochemistry* 1986, 25, 7344) (10 mM Tris•HCl, 10 mM KCl, 10 mM MgCl$_2$ and 5 mM CaCl$_2$, pH 7.0 and 22° C.) were performed to determine the equilibrium association constant (K$_a$) of each six-ring hairpin polyamide for the three resolved sites (FIGS. 10 and 11). The 5'-TGTTA-3' site is bound by polyamides in the order: ImPyPy-(R)$^{H2N}$γ-PyPyPy-β-Dp (1-R) (K$_a$=3.8×10$^9$ M$^{-1}$)_ImPyPy-(R)$^{H2N}$γ-PyPyPy-β-EtOH (2-R) (K$_a$=3.3×10$^9$ M$^{-1}$)>ImPyPy-(R)$^{Ac}$γ-PyPyPy-β-Dp (3-R) (K$_a$=3.0×10$^8$ M$^{-1}$)_ImPyPy-γ-PyPyPy-β-Dp (K$_a$=2.9×10$^8$ M$^{-1}$)>ImPyPy-(S)$^{H2N}$γ-PyPyPy-β-Dp (1-S) (K$_a$=2.2×10$^7$ M$^{-1}$)>ImPyPy-(S)$^{Ac}$γ-PyPyPy-β-Dp (3-S) (K$_a$<5.0×10$^6$ M$^{-1}$). Equilibrium association constants for recognition of the 5'-TGACT-3' single base pair mismatch site are: ImPyPy-(R)$^{H2N}$γ-PyPyPy-β-Dp (1-R) (K$_a$=3.5×10$^7$ M$^{-1}$)_ImPyPy-(R)$^{H2N}$γ-PyPyPy-β-EtOH (2-R) (K$_a$=3.1×10$^7$ M$^{-1}$)>ImPyPy-(R)$^{Ac}$γ-PyPyPy-β-Dp (3-R) (K$_a$<5×10$^6$ M$^{-1}$)_ImPyPy-γ-PyPyPy-β-Dp (K$_a$=4.8×10$^6$ M$^{-1}$). The polyamides ImPyPy-(S)$^{H2N}$γ-PyPyPy-β-Dp (1-S) and ImPyPy-(S)$^{Aγ}$γ-PyPyPy-β-Dp (3-S) recognize the 5'-ACATT-3' reverse orientation sequence with K$_a$=4.6×10$^6$ M$^{-1}$ and K$_a$<5×10$^6$ M$^{-1}$ respectively. It should be noted that a detailed comparison of the relative mismatch binding energetics cannot be made since the 5'-TGACA-3' and 5'-ACATT-3' binding sites overlap. The relative affinity of 5'-TGTTA-3' match site binding varies from 100-fold to 5-fold depending on the stereochemistry of the γ-turn substitutions (Table 2).

TABLE 2

Equilibrium Association Constants (M$^{-1}$)[a,b]

| Improved Polymide | Match Site 5'-TGTTA-3' | Reverse Site 5'-ACATT-3' | Mismatch Site 5'-TGACA-3' | Specificity[c] |
|---|---|---|---|---|
| ImPyPy-γ-PyPyPy-β-Dp | 2.9 × 10$^8$ | ND | 4.8 × 10$^6$ | 60 |
| ImPyPy-(R)$^{H2N}$γ-PyPyPy-β-Dp | 3 × 10$^9$ (0.2) | ND | 3.5 × 10$^7$ (1.0) | 100 |
| ImPyPy-(S)$^{H2N}$γ-PyPyPy-β-Dp | 2.2 × 10$^7$ (0.7) | 4.6 × 10$^6$ (2.0)[d] | ND | 5 |
| ImPyPy-(R)$^{H2N}$γ-PyPyPy-β-EtOH | 3.3 × 10$^9$ (0.9) | ND | 3.1 × 10$^7$ (0.4) | 100 |
| ImPyPy-(R)$^{Ac}$γ-PyPyPy-β-Dp | 3.0 × 10$^8$ (1.3) | ND | <5.0 × 10$^6$ | ≧60 |
| ImPyPy-(S)$^{Ac}$γ-PyPyPy-β-Dp | <5.0 × 10$^6$ | <5.0 × 10$^6$ | ND | ND |

[a]The reported association constants are the average values obtained from three DNase I footprint titration experiments. The standard deviation for each data set is indicated in parentheses. The assays were carried out at 22° C. at pH 7.0 in the presence of 10 mM Tris-HCl, 10 mM KCl, 10 mM MgCl$_2$, and 5 mM CaCl$_2$.
[b]The five base piar binding sites are in capital letters.
[c]Specificity is calculated by K$_a$ (match site/K$_a$ (mismatch site).
[d]Mismatch site is 5'(ACATT)-3' for ImPyPy-(S)$^{H2N}$γ-PyPyPy-β-Dp-(1-S) and ImPyPy-(S)$^{Ac}$γ-PyPyPy-β-Dp (3-S) as determined by MPE*FE(II) footprinting and affinity cleaving.
ND = not determined.

Example 5

Binding Site Size and Orientation

MPE•Fe(II) footprinting reveals that the polyamides bind with highest affinity to the 5'-TGTTA-3' match site, the 5'-TGACA-3' single base pair mismatch site for polyamides 1-R and 3-R, and the 5'-ACATT-3' reverse orientation match site for polyamides 1-S and 3-S (FIG. 6). Affinity cleaving experiments using polyamides with EDTA•Fe(II) placed at either the carboxy terminus or the γ-turn confirm that polyamides derived from both (R) and (S)-2,4-diaminobutyric acid bind to the 5'-TGTTA-3' target site with a single orientation (FIG. 10). The observation of a single cleavage locus is consistent only with an oriented 1:1 polyamide:DNA complex in the minor groove and rules out any dimeric overlapped or extended binding motifs. The hairpin binding model is further supported by the location of the cleavage locus at either the 5' or 3' side of the 5'-TGTTA-3' target site corresponding to EDTA•Fe(II) placement at the polyamide carboxy terminus or the γ-turn, respectively (FIG. 10). Polyamide subunits linked by the (R)$^{H2N}$γγ bind the symmetric single base pair mismatch sequence 5'TGACA-3' in two distinct orientations. Polyamides linked with (S)$^{H2N}$γ bind to a 5'-ACATT-3' reverse orientation match sequence as revealed by a unique cleavage locus at the 5' side of the site.

Example 6

Binding Affinity

All six polyamides bind to the 5'-TGTTA-3' target site with binding isotherms (eq. 2, n=1) consistent with binding as an intramolecular hairpin (FIG. 11). However the relative match site binding affinity varies by nearly 1000-fold depending on the stereochemistry of the γ-turn and the nature of the substituents. Among the six polyamides, ImPyPy-(R)$^{H_2N}$γ-PyPyPy-β-Dp (1-R) binds to the targeted 5'-TGTTA-3' site with the highest affinity. ImPyPy-(R)$^{H_2N}$γ-PyPyPy-β-Dp binds with an equilibrium association constant, ($K_a$=3×10$^9$ M$^{-1}$; Parks, et al. *J. Am. Chem. Soc.* 1996, 118, 6147), a factor of 10 greater than that of the parent polyamide, ImPyPy-γ-PyPyPy-β-Dp, ($K_a$=3×10$^8$ M$^{-1}$). Replacement of the C-terminal dimethylaminopropylamide group of 1-R with an ethoxyamide group as in ImPyPy-(R)$^{H_2N}$γ-PyPyPy-β-EtOH (2-R) results in no decrease in binding affinity ($K_a$=3×10$^9$ M$^{-1}$). Acetylation of the γ-turn amino group as in ImPyPy-(R)$^{Ac}$γ-PyPyPy-β-Dp (3-R) reduces binding affinity 10-fold ($K_a$=3×10$^8$ M$^{-1}$) relative to 1-R.

The observation that polyamides which differ only by replacement of the dimethylaminopropylamide group 1-R with an ethoxyamide group 2-R bind with similar affinity indicates that interactions between the cationic dimethylaminopropyl tail group with anionic phosphate residues or the negative electrostatic potential in the floor of the minor groove may not contribute substantially to the energetics of hairpin-DNA binding (Zimmer, et al. *Prog. Biophys, Molec. Biol.* 1986, 47, 31; Pullman, B. *Adv. Drug. Res.* 1990, 18, 1; Breslauer, et al. *Structure and Expression* (Vol. 2), *DNA and Its Drug Complexes* p. 273–289, R. H. Sarma and M. H. Sarma (eds.) Academic Press (1988)). Furthermore, these results indicate that the observed binding enhancement of 1-R, in relation to ImPyPy-γ-PyPyPy-β-Dp, is not simply the difference between a monocationic and dicationic ligand binding to the polycationic DNA helix (Zimmer, et al. *Prog. Biophys. Molec. Biol.* 1986, 47, 31; Pullman, B. *Adv. Drug. Res.* 1990, 18, 1; Breslauer, et al. *Structure and Expression* (Vol. 2), *DNA and Its Drug Complexes* p. 273–289, R. H. Sarma and M. H. Sarma (eds.) Academic Press (1988)). The modest increased binding affinity of polyamide 1-R may result from electrostatic interactions between the precisely placed amine group and the floor of the minor groove. Alternately, the increased affinity could indicate a reduction in the degrees of freedom accessible to the free hairpin in solution resulting from a steric effect, or an electrostatic interaction between the positively charged amine group and the negative potential of the γ-carbonyl group.

Polyamides linked with (S)$^{H_2N}$γ, ImPyPy-(S)$^{H_2N}$γ-PyPyPy-β-Dp (1-S) and ImPyPy-(S)$^{Ac}$γ-PyPyPy-β-Dp (3-S), bind to the 5'-TGTTA-3' match site with 100-fold ($K_a$=2×10$^7$ M$^{-1}$) and 1000-fold ($K_a$<5×10$^6$ M$^{-1}$) reduced affinity relative to the (R)$^{H_2N}$γ linked polyamide 1-R. These results demonstrate that the DNA-binding affinity of chiral hairpin polyamides can be predictably regulated as a function of the stereochemistry of the turn residue.

Example 7

Sequence-specificity

Polyamides with a variety of substitutions at the γ-turn bind preferentially to the 5'-TGTTA-3' match site, while overall specificity versus binding at reverse orientation and mismatch sites is modified. Replacing the α-proton in the γ-residue of ImPyPy-γ-PyPyPy-β-Dp with an amino group that confers a chiral α-hydrogen (R) configuration, provides the most specific polyamide ImPyPy-(R)$^{H_2N}$γ-PyPyPy-β-Dp (1-R). The ImPyPy-(R)$^{H_2N}$γ-PyPyPy-β-Dp•5'-TGTTA-3' complex forms with 100-fold preference relative to the ImPyPy-(R)$^{H_2N}$γ-PyPyPy-β-Dp•5'-TGTCA-3' mismatch complex. Substitution of the charged dimethylaminopropyl tail group with an ethoxyamide group as in (2-R) does not alter binding specificity. The modest increase in specificity against single base mismatch sequences for polyamides 1-R and 2-R (100-fold) relative to the parent unsubstituted hairpin polyamide (60-fold) implicates chiral hairpin polyamides as an optimized class of small molecules for recognition of the DNA minor groove.

Example 8

Binding Orientation

In principle, a polyamide:DNA complex can form at two different DNA sequences depending on the alignment of the polyamide (N-C) with the walls of the minor groove (5'-3'; White, et al. *J. Am. Chem. Soc.* 1997, 119, 8756). A six ring-hairpin polyamide of core sequence composition ImPyPy-γ-PyPyPy which places the N-terminus of each three-ring polyamide subunit at the 5'-side of individual recognized DNA strands would bind to 'forward match' 5'-WGWWW-3' sequences (W=A or T). Placement of the polyamide N-terminus at the 3'-side of each recognized strand would result in targeting 'reverse match' 5'-WCWWW-3' sequences. For hairpin polyamides there is an energetic preference for 'forward' alignment of each polyamide subunit (N-C) with respect to the backbone (5'-3') of the DNA double helix (White, et al. *J. Am. Chem. Soc.* 1997, 119, 8756).

In addition to decreasing the affinity for the 5'-TGTTA-3' match site, replacing the α-proton of γ-turn in ImPyPy-γ-PyPyPy-β-Dp with (S)$^{H_2N}$γ changes the mismatch sequence preference from the 5'-TGACA-3' site bound by the (R)$^{H_2N}$γ-linked polyamides to a 5'-ACATT-3' reverse match site. Binding to the reverse site may result from the presence of the steric bulk of the amino or acetamido groups in the floor of the minor groove preventing the deep polyamide binding required for specific DNA recognition. However, an analysis of hairpin folding requirements for 'forward' and 'reverse' binding reveals an additional model.

Figure 12:
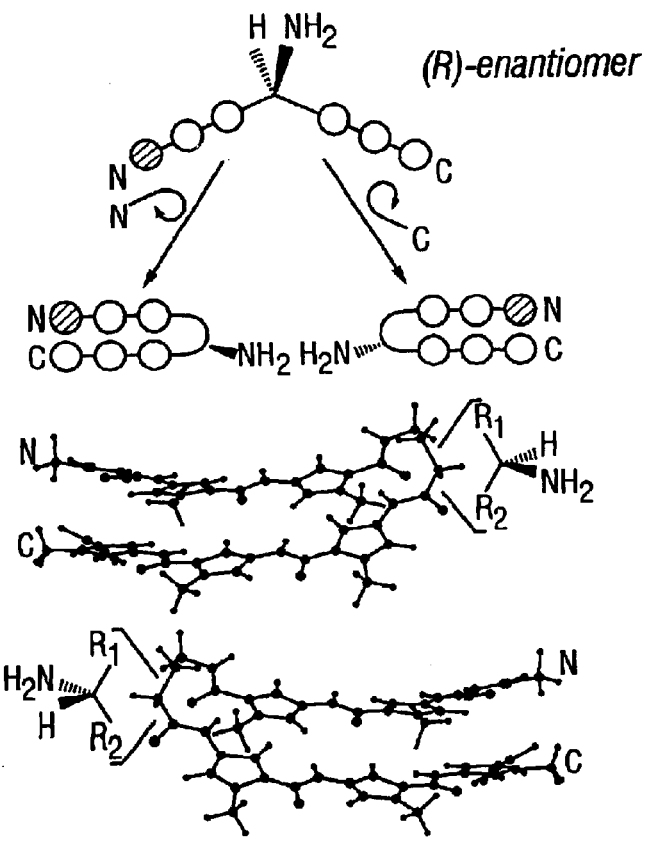
FIG. 12. Model for chiral hairpin folding of improved polyamides.
Figure 13:
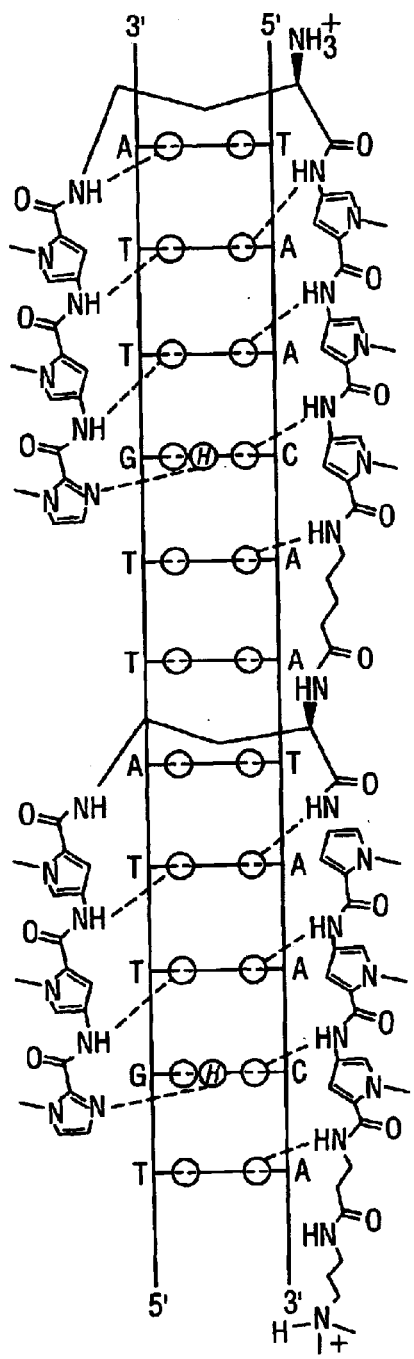
FIG. 13. Hydrogen bonding model of a tandemly-linked polyamide using SEQ ID NOS 25 and 26.
Figure 13:
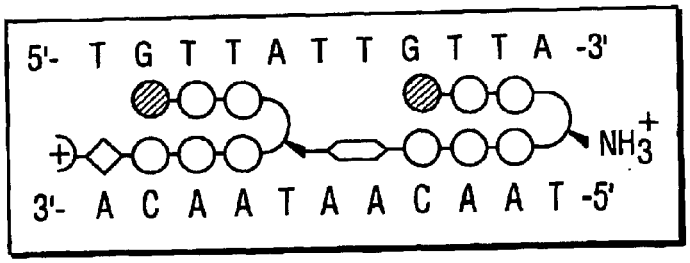

In principle, there exist two non-superimposable hairpin folds which are related by mirror plane symmetry (FIG. 12). One hairpin fold is responsible for the preferred 5' to 3' N to C orientation, while the other fold corresponds to the 3' to 5' N to C reverse orientation binding. For an achiral hairpin polyamide in the absence of DNA, each non-superimposable fold should be energetically equivalent. However, an asymmetrically folded hairpin polyamide with a chiral substituent could potentially display differential energetics for oriented binding (FIG. 12). In the forward folded hairpin (5' to 3' N to C), (R)$^{H_2N}$γ directs the amine functionality away from the DNA helix, while (S) enantiomer is predicted to direct the amine into the floor of the minor groove. For the 'reverse' fold hairpin, (S)$^{H_2N}$γ directs the amine functionality away from the floor of the DNA helix, while the amine of the (R) enantiomer is predicted to clash with the floor of the helix. The modest enhanced specificity of chiral polyamides 1-R and 2-R relative to the unsubstituted parent hairpin may result from stabilization of the forward binding mode and/or destabilization of the reverse binding hairpin fold.

Example 9

Tandemly-Linked Polyamides

A. Synthesis

ImPyPy-(R)[ImPyPy-(R)$^{H_2N}$γ-PyPyPy-β-]$^{HN}$γ-PyPyPy-β-Dp (6) and ImPyPy-(R)[ImPyPy-(R)$^{H_2N}$γ-PyPyPy-δ-]$^{HN}$γ-PyPyPy-β-Dp (7) were synthesized from Boc-β-alanine-Pam resin (0.6 g resin, 0.6 mmol/g substitution) using Boc-chemistry machine-assisted protocols in 31 steps (FIG.

3).[12] ImPyPy-(R)$^{FmocHN}$γ-PyPyPy-β-Pam-Pam resin was prepared as described.[10] The Fmoc protecting group was then removed by treatment with (4:1) piperidine/DMF. The remaining amino acid sequence was then synthesized in a stepwise manner using Boc-chemistry machine assisted protocols to provide ImPyPy-(R)[ImPyPy-(R)$^{FmocHN}$γ-PyPyPy-β-]$^{HN}$γ-PyPyPy-β-Pam-Resin and ImPyPy-(R)[ImPyPy-(R)$^{FmocHN}$γ-PyPyPy-δ-]$^{HN}$γ-PyPyPy-β-Pam-Resin. The Fmoc group was removed with (4:1) piperidine/DMF. A sample of resin was then cleaved by a single-step aminolysis reaction with ((dimethylamino)propylamine (55° C., 18 h) and the reaction mixture subsequently purified by reversed phase HPLC to provide ImPyPy-(R)[ImPyPy-(R)$^{H2N}$γ-PyPyPy-β-]$^{HN}$γ-PyPyPy-β-Dp (6) and ImPyPy-(R)[ImPyPy-(R)$^{H2N}$γ-PyPyPy-δ-]$^{HN}$γ-PyPyPy-β-Dp (7). For the synthesis of the EDTA-turn derivative 7-E, a sample ImPyPy-(R)[ImPyPy-(R)$^{H2N}$γ-PyPyPy-δ-]$^{HN}$γ-PyPyPy-β-Dp (7) was treated with an excess of EDTA-dianhydride (DMSO/NMP, DIEA 55° C., 30 min.) and the remaining anhydride hydrolyzed (0.1 M NaOH, 55° C., 10 min.). The polyamide ImPyPy-(R)[ImPyPy-(R)$^{EDTA}$γ-PyPyPy-δ-]$^{HN}$γ-PyPyPy-β-Dp (7-E) was then isolated by reverse phase HPLC. The dicationic twelve-ring tandem hairpins are soluble at concentrations up to 1 mM. The solubility of the tandem hairpins is 10- to 100-fold greater than that found for extended or hairpin twelve-ring polyamides.

ImPyPy-(R)[ImPyPy-(R)$^{H2N}$γ-PyPyPy-β-]$^{HN}$γ-PyPyPy-β-Dp ("6")

ImPyPy-(R)$^{Fmoc}$γ-PyPyPy-β-Pam-Resin was synthesized in a stepwise fashion by machine-assisted solid phase methods from Boc-β-Pam-Resin (0.6 mmol/g). (R)-2-Fmoc-4-Boc-diaminobutyric acid (0.7 mmol) was incorporated as previously described for Boc-γ-aminobutyric acid. ImPyPy-(R)$^{Fmoc}$γ-PyPyPy-β-Pam-Resin was placed in a glass 20 mL peptide synthesis vessel and treated with DMF (2 mL), followed by piperidine (8 mL) and agitated (22° C., 30 min.). ImPyPy-(R)$^{H2N}$γ-PyPyPy-β-Pam-resin was isolated by filtration, and washed sequentially with an excess of DMF, DCM, MeOH, and ethyl ether and the amine-resin dried in vacuo. ImPyPy-(R)[ImPyPy-(R)$^{FmocHN}$γ-PyPyPy-β-]$^{HN}$γ-PyPyPy-β-Pam-Resin was then synthesized in a stepwise fashion by machine-assisted solid phase methods from ImPyPy-(R)$^{H2N}$γ-PyPyPy-β-Pam-resin (0.38 mmol/g). ImPyPy-(R)[ImPyPy-(R)$^{FmocHN}$γ-PyPyPy-β-]$^{HN}$γ-PyPyPy-β-Pam-Resin was placed in a glass 20 mL peptide synthesis vessel and treated with DMF (2 mL), followed by piperidine (8 mL) and agitated (22° C., 30 min.). ImPyPy-(R)[ImPyPy-(R)$^{H2N}$γ-PyPyPy-β-]$^{HN}$γ-PyPyPy-β-Pam-Resin was isolated by filtration, and washed sequentially with an excess of DMF, DCM, MeOH, and ethyl ether and the amine-resin dried in vacuo. A sample of ImPyPy-(R)[ImPyPy-(R)$^{H2N}$γ-PyPyPy-β-]$^{HN}$γ-PyPyPy-β-Pam-Resin (240 mg, 0.29 mmol/gram) was treated with neat dimethylaminopropylamine (2 mL) and heated (55° C.) with periodic agitation for 16 h. The reaction mixture was then filtered to remove resin, 0.1% (wt/v) TFA added (6 mL) and the resulting solution purified by reversed phase HPLC. ImPyPy-(R)[ImPyPy-(R)$^{H2N}$γ-PyPyPy-β-]$^{HN}$γ-PyPyPy-β-Dp is recovered upon lyophilization of the appropriate fractions as a white powder (28 mg, 22% recovery). UV (H$_2$O) λ$_{max}$ 246, 306 (100,000); MALDI-TOF-MS [M$^+$–H] (monoisotopic), 1881.9: 1881.9 calc. for C$_{89}$H$_{109}$N$_{32}$O$_{16}$ ImPyPy-(R)[ImPyPy-(R)$^{H2N}$γ-PyPyPy-δ-]$^{HN}$γ-PyPyPy-β-Dp ("7")

ImPyPy-(R)[ImPyPy-(R)$^{H2N}$γ-PyPyPy-δ-]$^{HN}$γ-PyPyPy-β-Pam-Resin was prepared as described for ImPyPy-(R)[ImPyPy-(R)$^{H2N}$γ-PyPyPy-β-]$^{HN}$γ-PyPyPy-β-Pam-Resin. A sample of ImPyPy-(R)[ImPyPy-(R)$^{H2N}$γ-PyPyPy-δ-]$^{HN}$γ-PyPyPy-β-Pam-Resin (240 mg, 0.29 mmol/gram[19]) was treated with neat dimethylaminopropylamine (2 mL) and heated (55° C.) with periodic agitation for 16 h. The reaction mixture was then filtered to remove resin, 0.1% (wt/v) TFA added (6 mL) and the resulting solution purified by reversed phase HPLC. ImPyPy-(R)[ImPyPy-(R)$^{H2N}$γ-PyPyPy-δ-]$^{HN}$γ-PyPyPy-β-Dp is recovered upon lyophilization of the appropriate fractions as a white powder (32 mg, 25% recovery). [α]$^{20}_D$+14.6 (c 0.05, H$_2$O); UV (H$_2$O) λ$_{max}$ 246, 306 (100,000); $^1$H NMR (300 MHz, [D$_6$]DMSO, 20° C.): δ=10.54 (s, 1 H; aromatic NH); 10.45 (s, 1 H; aromatic NH); 10.44 (s, 1 H; aromatic NH); 10.02 (s, 1 H; aromatic NH); 9.95 (s, 1 H; aromatic NH); 9.92 (s, 1 H; aromatic NH); 9.90 (d, 2 H; aromatic NH); 9.86 (d, 2 H; aromatic NH); 9.2 (br s, 1 H; CF$_3$COOH); 8.25 (m, 4 H; aliphatic NH, NH$_3$); 8.11 (d, 1 H; J=8.5 Hz, aliphatic NH); 8.04 (m, 4H, aliphatic NH), 7.37 (s, 2 H; CH); 7.25 (m, 2 H; CH); 7.22 (d, 1 H; CH); 7.18 (m, 2 H; CH); 7.16 (m, 3 H; CH); 7.12 (m, 4 H; CH); 7.02 (m, 4 H; CH); 6.95 (d, 1 H; J=1.6 Hz; CH); 6.91 (d, 1 H; J=1.5 Hz; CH); 6.88 (d, 1 H; J=1.3 Hz; CH); 6.85 (m, 3 H; CH); 5.32 (t, 1 H; aliphatic CH), 4.45 (m, 1 H, aliphatic CH), 3.96 (s, 6 H; NCH$_3$); 3.83 (s, 3 H; NCH$_3$); 3.80 (s, 18 H; NCH$_3$); 3.79 (s, 3 H; NCH$_3$); 3.76 (s, 3 H; NCH$_3$); 3.39 (m, 4 H; CH$_2$); 3.28 (m, 2 H; CH$_2$); 3.15 (m, 4 H; CH$_2$); 3.07 (m, 2 H; CH$_2$); 2.97 (m, 2 H; CH$_2$); 2.70 (d, 6 H; N(CH$_3$)$_2$); 2.32 (m, 2 H; CH$_2$); 1.93 (m, 2 H; CH$_2$); 1.71 (m, 2 H; CH$_2$); 1.47 (m, 2 H; CH$_2$); 1.20 (m, 4 H; CH$_2$); MALDI-TOF-MS [M$^+$–H] (monoisotopic), 1910.2: 1909.9 calc. for C$_{91}$H$_{113}$N$_{32}$O$_{16}$.

ImPyPy-(R)[ImPyPy-(R)$^{EDTA}$γ-PyPyPy-δ-]$^{HN}$γ-PyPyPy-β-Dp ("7-E")

Figure 18:
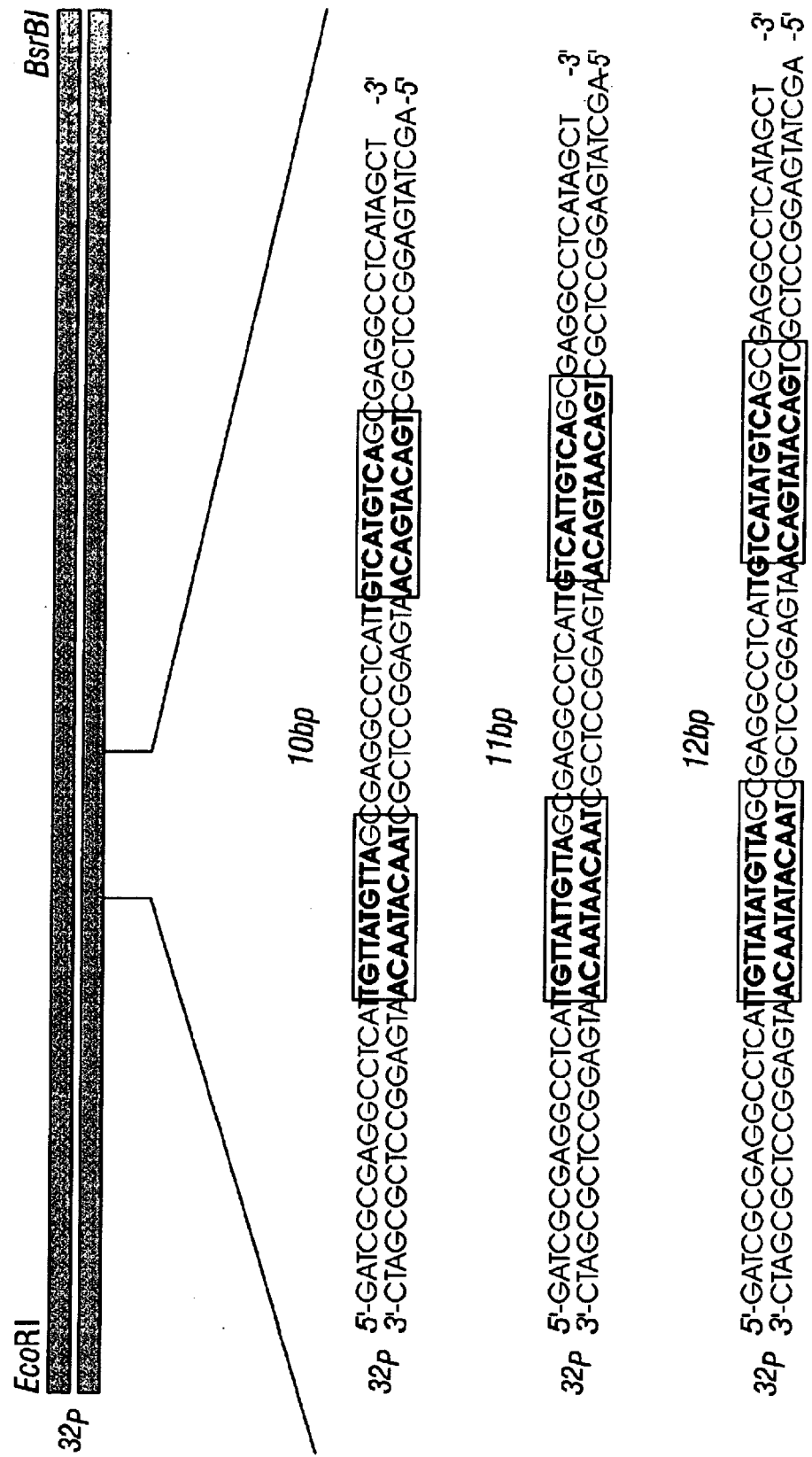
FIG. 18. Construction of plasmids pDH10, pDH11, and pDH12 comprising SEQ ID NOS 31–36.

Excess EDTA-dianhydride (50 mg) was dissolved in DMSO/NMP (1 mL) and DIEA (1 mL) by heating at 55° C. for 5 min. The dianhydride solution was added to ImPyPy-(R)[ImPyPy-(R)$^{H2N}$γ-PyPyPy-δ-]$^{HN}$γ-PyPyPy-β-Dp (10 mg, 5 μmol) dissolved in DMSO (750 μL). The mixture was heated (55° C., 25 min.) and the remaining EDTA-anhydride hydrolyzed (0.1M NaOH, 3 mL, 55° C., 10 min). Aqueous TFA (0.1% wt/v) was added to adjust the total volume to 8 mL and the solution purified directly by reversed phase HPLC to provide ImPyPy-(R)[ImPyPy-(R)$^{EDTA}$γ-PyPyPy-δ-]$^{HN}$γ-PyPyPy-β-Dp (7-E) as a white powder upon lyophilization of the appropriate fractions (2 mg, 20% recovery). MALDI-TOF-MS [M$^+$–H] (monoisotopic), 2184.3: 2184.0 calc. for C$_{101}$H$_{127}$N$_{34}$O$_{23}$ B. Plasmid and Restriction Fragment Preparation The plasmids pDH10, pDH11, and pDH12 were constructed by hybridization of the inserts listed in FIG. 18. Each hybridized insert was ligated individually into linearized pUC19 BamHI/HindIII plasmid using T4 DNA ligase. The resultant constructs were used to transform Top10F' OneShot competent cells from Invitrogen. Ampicillin-resistant white colonies were selected from 25 mL Luria-Bertani medium agar plates containing 50 μg/mL ampicillin and treated with XGAL and IPTG solutions. Large-scale plasmid purification was performed with Qiagen Maxi purification kits. Dideoxy sequencing was used to verify the presence of the desired insert. Concentration of the prepared plasmid was determined at 260 nm using the relationship of 1 OD unit=50 μg/mL duplex DNA.

The plasmids pDH(11–12) were linearized with EcoRI and BsrBI, then treated with the Sequenase enzyme, deoxyadenosine 5'-[α-$^{32}$P]triphosphate and thymidine 5'-[α-$^{32}$P] triphosphate for 3' labeling. Alternatively, these plasmids were linearized with EcoRI, treated with calf alkaline phosphatase, and then 5' labeled with T4 polynucleotide kinase and deoxyadenosine 5'-[γ-$^{32}$P]triphosphate. The 5' labeled fragment was then digested with BsrBI. The labeled fragment (3' or 5') was loaded onto a 6% non-denaturing polyacrylamide gel, and the desired 147 base pair band was visualized by autoradiography and isolated. Chemical sequencing reactions were performed according to published methods.

C. Binding Site Size

All reactions were carried out in a volume of 40 µL. A polyamide stock solution or water (for reference lanes) was added to an assay buffer where the final concentrations were: 25 mM Tris-acetate buffer (pH 7.0), 10 mM NaCl, 100 µM/base pair calf thymus DNA, and 30 kcpm 3'- or 5'-radiolabeled DNA. The solutions were allowed to equilibrate for 4 hours. A fresh 50 µM MPE•Fe(II) solution was prepared from 100 µL of a 100 µM MPE solution and 100 µL of a 100 µM ferrous ammonium sulfate (Fe(NH$_4$)$_2$(SO$_4$)$_2$.6H$_2$O) solution. MPE•Fe(II) solution (5 µM) was added to the equilibrated DNA, and the reactions were allowed to equilibrate for 5 minutes. Cleavage was initiated by the addition of dithiothreitol (5 mM) and allowed to proceed for 14 min. Reactions were stopped by ethanol precipitation, resuspended in 100 mM tris-borate-EDTA/80% formamide loading buffer, denatured at 85° C. for 6 min, and a 5 µL sample (~15 kcpm) was immediately loaded onto an 8% denaturing polyacrylamide gel (5% crosslink, 7 M urea) at 2000 V.

MPE•Fe(II) footprinting on 3'- or 5'-$^{32}$P end-labeled 135 base pair EcoRI/BsrBI restriction fragments from the plasmid pDH11 reveals that polyamide 7, at 100 pM concentration, binds to the designated 11-bp match site 5'-TGTTATTGTTA-3' SEQ ID NO. 1 (25 mM Tris-acetate, 10 mM NaCl, pH 7.0 and 22° C.) (FIGS. 5a and 5c). Binding of the mismatch site 5'-TGTCATTGTCA-3' SEQ ID NO. 2 is only observed at much higher polyamide concentrations (FIG. 5a). The size of the asymmetrically 3'-shifted cleavage protection pattern for polyamide 7 at the designated match site 5'-TGTTATTGTTA-3' SEQ ID NO. 1 is consistent with formation of the predicted hairpin-δ-hairpin•DNA complex.

D. Binding Orientation

All reactions were carried out in a volume of 40 µL. A polyamide stock solution or water (for reference lanes) was added to an assay buffer where the final concentrations were: 25 mM Tris-acetate buffer (pH 7.0), 20 mM NaCl, 100 µM/base pair calf thymus DNA, and 20 kcpm 3'- or 5'-radiolabeled DNA. The solutions were allowed to equilibrate for 8 hours. A fresh solution of ferrous ammonium sulfate (Fe(NH$_4$)$_2$(SO$_4$)$_2$.6H$_2$O) (10 µM) was added to the equilibrated DNA, and the reactions were allowed to equilibrate for 15 minutes. Cleavage was initiated by the addition of dithiothreitol (10 mM) and allowed to proceed for 30 min. Reactions were stopped by ethanol precipitation, resuspended in 100 mM tris-borate-EDTA/80% formamide loading buffer, denatured at 85° C. for 6 min, and the entire sample was immediately loaded onto an 8% denaturing polyacrylamide gel (5% crosslink, 7 M urea) at 2000 V.

Affinity cleavage experiments using 7-E which has an EDTA•Fe(II) moiety appended to the γ-turn, were used to confirm polyamide binding orientation and stoichiometry. Affinity cleavage experiments were performed on the same 3'- or 5'-$^{32}$P end-labeled 135 base pair DNA restriction fragment from the plasmid pDH11 (25 mM Tris-acetate, 10 mM NaCl, 100 µM/base pair calf thymus DNA, pH 7.0 and 22° C.). The observed cleavage pattern for 7-E (FIGS. 5b and 5d) are 3'-shifted, consistent with minor groove occupancy. In the presence of 1 µM 7-E, a single cleavage locus proximal to the 3' side of the 5'-TGTTATTGTTA-3' SEQ ID NO. 1 match sequence is revealed, consistent with formation of an oriented 1:1 hairpin-δ-hairpin•DNA complex.

E. Equilibrium Association Constants

Quantitative DNase I footprinting and related mathematical calculations were performed as described above in Example 4, except as otherwise indicated below. Quantitative DNase I footprint titrations (10 mM Tris•HCl, 10 mM KCl, 10 mM MgCl$_2$ and 5 mM CaCl$_2$, pH 7.0 and 22° C.) were performed to determine the equilibrium association constants ($K_a$) of 6 and 7 for the 10-, 11- and 12-bp match and mismatch sites (Table 1). Polyamide 7 preferentially binds the 11-bp 5'-TGTTATTGTTA-3' SEQ ID NO. 1 target sequence with an equilibrium association constant, $K_a$>1×10$^{11}$ M$^{-1}$. The corresponding 11 bp mismatch 5'-TGTCATTGTCA-3' SEQ ID NO. 2 site is bound by 7 with >4500-fold lower affinity ($K_a$=2.2×10$^8$ M$^{-1}$). Polyamide 7 binds the 10 bp site 5'-TGTTATGTTA-3' SEQ ID No. 3 ($K_a$=1.5×10$^{10}$ M$^{-1}$) and the 12 bp site 5'-TGTTATATGTTA-3' SEQ ID NO. 4 ($K_a$=1.0×10$^9$ M$^{-1}$) with 70- and 1000-fold lower affinity, respectively. Polyamide 6 binds the 10-bp 5'-TGTTATGTTA-3' SEQ ID NO. 3 site and 11-bp 5'-TGTTATTGTTA-3' SEQ ID NO. 1 site with $K_a$=2×10$^{10}$ M$^{-1}$, and also binds the 12-bp 5'-TGTTATATGTTA-3' SEQ ID NO. 4 site with 16-fold lower affinity ($K_a$=9.0×10$^9$ M$^{-1}$). The parent hairpin ImPyPy-(R)$^{H2N}$γ-PyPyPy-β-Dp was found to bind to the 5'-TGTTA-3' match site with $K_a$=5×10$^9$ M$^{-1}$.

Formally the subunits of polyamide 7 represent the combination of the parent-acetylated parent tandem hairpin. The parent and acetylated hairpins occupy I with binding energetics of −13.2 kcal/mol and −11.8 kcal/mol respectively, predicting that covalent linkage of parent-δ-acetylated would bind the same site with an association constant of ($K_a$)=2.2×10$^{18}$ M$^{-1}$, 6 orders of magnitude higher than the observed tandem hairpin 7 which binds with −16.3 kcal/mol. Relative to parent recognition of the 5'-TGTTA-3' half site, we only observe a 2-fold enhancement and 5-fold decrease in binding respectively, recognition of the 10- and 12-bp sites. At site IV, a single base pair mismatch reduces binding eneretics for both unlinked and linked hairpins. Unlinked parent and acetylated-parent respectively bind with 10.5 kcal/mol and 9.2 kcal/mol, predicting the linked polyamide would bind with a ($K_a$)=2.4×10$^{14}$ M$^{-1}$. The observed tandem hairpin binds with energetics of −11.35 kcal/mol and a ($K_a$)=2.2×10$^8$ M$^{-1}$.

TABLE 2

Equilibrium Association Constants (M$^{-1}$)[a,b]

| Polyamide | 5'-aTGTTATGTTAg-3' SEQ ID NO.3 | 5'-aTGTCATGTCAt-3' SEQ ID NO.5 | Specificity |
| --- | --- | --- | --- |

TABLE 2-continued

Equilibrium Association Constants $(M^{-1})^{a,b}$

| 6 | [structure] | $2 \times 10^{10}$ | $1.5 \times 10^8$ | 133 |
| 7 | [structure] | $1.5 \times 10^{10}$ | $1.9 \times 10^8$ | 80 |

| Polyamide | 5'-aTGTTATTGTTAg-3' SEQ ID NO.1 | 5'-aTGTCATTGTCAt-3' SEQ ID NO.2 | Specificity |
|---|---|---|---|
| 6 | $1.5 \times 10^{10}$ | $2 \times 10^8$ | 75 |
| 7 | $\geq 1 \times 10^{12}$ | $2.2 \times 10^8$ | $\geq 4500$ |

| Polyamide | 5'-aTGTTATATGTTAg-3' SEQ ID NO.4 | 5'-aTGTCATATGTCAt-3' SEQ ID NO.6 | Specificity |
|---|---|---|---|
| 6 | $9 \times 10^8$ | $3 \times 10^7$ | 30 |
| 7 | $1 \times 10^9$ | $2.5 \times 10^7$ | 40 |

[a] The reported association constants are the average values obtained from three DNase 1 footprint titration experiments. The assays were carried out at 22° C. at pH 7.0 in the presence of 10 mM Tris-HCL. 10 mM KCl, 10 mM MgCl$_2$, ad 5 mM CaCl$_2$.
[b] The ten, eleven, and twelve base-pair sites are in capital letters, with flanking sequences in lower case letters. Match site association constants are shown in boldtype. Specificity is calculated as $K_a$(match)/$K_a$(mismatch).

F. Linker Dependence

Site size preferences of polyamides 6 and 7 result from modifications to the length if the turn-to-tail linker. Modeling indicated that β and δ linkers would provide sufficient length for recognition of either 10- or 11-base pairs, but would be too short to span the 12-bp binding site. Polyamide 7 displays optimal recognition of the 11-bp site, binding the 5'-TGTTATTGTTA-3' SEQ ID NO. 1 site with a $K_a$ $1 \times 10^{12}$ M$^{-1}$. Replacing the δ linker in 7 with the 2-carbon shorter β-alanine residue in 6 shows a reduction of affinity at the 11-bp site by >6-fold ($K_a$=1.5×10$^{10}$ M$^{-1}$). The highly reduced affinities of 6 and 7 at the 12-bp site indicates that covalent constants of the linker subunit prevents alignment of hairpin subunits for their binding sites.

TABLE 3

Binding affinity of 6-ring hairpin and δ-linked tandem hairpins at 11-bp match site I, and a series of mismatch sites II–VI

| | Parent | Polyamide 2 |
|---|---|---|
| I | 5'-T G T T A T T G T T A-3' SEQ ID NO.1<br>[structure]<br>3'-A C A A T A A C A A T-5' SEQ ID NO.7<br>$K_a = 5 \times 10^9$ M$^{-1}$ | 5'-T G T T A T T G T T A-3'<br>[structure]<br>3'-A C A A T A A C A A T-5'<br>$K_a \geq 1 \times 10^{12}$ M$^{-1}$ |
| II | 5'-T G T T A T G T T A G-3' SEQ ID NO.8<br>[structure]<br>3'-A C A A T A C A A T C-5' SEQ ID NO.9<br>$K_a = 5 \times 10^9$ M$^{-1}$ | 5'-T G T T A T G T T A G-3'<br>[structure]<br>3'-A C A A T A C A A T C-5'<br>$K_a = 1.5 \times 10^{10}$ M$^{-1}$ |

TABLE 3-continued

Binding affinity of 6-ring hairpin and δ-linked tandem hairpins at 11-bp match site I, and a series of mismatch sites II–VI

| | Parent | | Polyamide 2 | |
|---|---|---|---|---|
| III | 5'-T G T T A T A T G T T-3'<br>3'-A C A A T A T A C A A-5'<br>$K_a = 5 \times 10^9 \, M^{-1}$ | SEQ ID NO.10<br>SEQ ID NO.11 | 5'-T G T T A T A T G T T-3'<br>3'-A C A A T A T A C A A-5'<br>$K_a = 1 \times 10^9 \, M^{-1}$ | |
| IV | 5'-T G T C A T T G T C A-3'<br>3'-A C A G T A A C A G T-5'<br>$K_a = 5 \times 10^7 \, M^{-1}$ | SEQ ID NO.2<br>SEQ ID NO.12 | 5'-T G T C A T T G T C A-3'<br>3'-A C A G T A A C A G T-5'<br>$K_a = 2.2 \times 10^8 \, M^{-1}$ | |
| V | 5'-T G T T T C C T G T G-3'<br>3'-A C A A A G G A C A C-5'<br>$K_a = 3 \times 10^8 \, M^{-1}$ | SEQ ID NO.14<br>SEQ ID NO.15 | 5'-T G T T T C C T G T G-3'<br>3'-A C A A A G G A C A C-5'<br>$K_a = 1 \times 10^8 \, M^{-1}$ | |
| VI | 5'-T G A T T A C G C C A-3'<br>3'-A C T A A T G C G G T-5'<br>$K_a = 1 \times 10^8 \, M^{-1}$ | SEQ ID NO.16<br>SEQ ID NO.17 | 5'-T G A T T A C G C C A-3'<br>3'-A C T A A T G C G G T-5'<br>$K_a = 5 \times 10^7 \, M^{-1}$ | |

As disclosed herein, the present invention provides the reagents and methodologies for the preparation and use of a variety of new chiral hairpin polyamide structures for specific recognition in the DNA minor groove. While a preferred form of the invention has been shown in the drawings and described, since variations in the preferred form will be apparent to those skilled in the art, the invention should not be construed as limited to the specific form shown and described, but instead is as set forth in the claims.

We claim:

1. In a polyamide having a hairpin turn derived from γ-aminobutyric acid which specifically binds to base pairs in the minor groove of a DNA molecule, the improvement comprising substitution of the γ-aminobutyric acid residue of the hairpin with (R)-2,4-diaminobutyric acid.

2. A polyamide of claim 1 wherein the R-2-amino is derivatized to form an acid amide.

3. A polyamide of claim 1 wherein the polyamide has three or four carboxyamide binding pairs.

4. A polyamide of claim 1 having the formula:

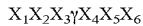

wherein γ is [—NH—CH$_2$—CH$_2$—CH$_2$—CONH— hairpin linkage derived from γ-aminobutyric acid or] a chiral hairpin linkage derived from R-2,4-diaminobutyric acid; and $X_1/X_6$, $X_2/X_5$, and $X_3/X_4$ represent three carboxamide binding pairs which bind DNA base pairs wherein at least one binding pair is Hp/Py or Py/Hp and the other binding pair(s) is(are) selected from the group consisting of Py/Im, Im/Py, and Py/Py to correspond to the DNA base pair in the minor groove to be bound.

5. A polyamide of claim 1 having the formula:

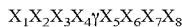

wherein γ is [—NH—CH$_2$—CH$_2$—CH$_2$—CONH— hairpin linkage derived from γ-aminobutyric acid or] a chiral hairpin linkage derived from R-2,4-diaminobutyric acid; and $X_1/X_8$, $X_2/X_7$, $X_3/X_6$, and $X_4/X_5$ represent four carboxamide binding pairs which bind DNA base pairs wherein at least one binding pair is Hp/Py or Py/Hp and the other binding pair(s) is(are) selected from the group consisting of Py/Im, Im/Py, and Py/Py to correspond to the DNA base pair in the minor groove to be bound.

6. A polyamide of claim 1 having the formula:

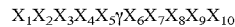

wherein γ is [—NH—CH$_2$—CH$_2$—CH$_2$—CONH— hairpin linkage derived from γ-aminobutyric acid or] a chiral hairpin linkage derived from R-2,4-diaminobutyric acid; and $X_1/X_{10}$, $X_2/X_9$, $X_3/X_8$, $X_4/X_7$, and $X_5/X_6$ represent five carboxamide binding pairs which bind DNA base pairs wherein at least one binding pair is Hp/Py or Py/Hp and the other binding pair(s) is(are) selected from the group consisting of Py/Im, Im/Py, and Py/Py to correspond to the DNA base pair in the minor groove to be bound.

7. A polyamide of claim 1 having the formula:

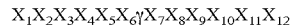

wherein γ is [—NH—CH$_2$—CH$_2$—CH$_2$—CONH— hairpin linkage derived from γ-aminobutyric acid or] a chiral hairpin linkage derived from R-2,4-diaminobutyric acid; and $X_1/X_{12}$, $X_2/X_{11}$, $X_3X_{10}$, $X_4X_9$, $X_5X_8$, and $X_6/X_7$ represent six carboxamide binding pairs which bind DNA base pairs wherein at least one binding pair is Hp/Py or Py/Hp and the other binding pair(s) is(are) selected from the group consisting of Py/Im, Im/Py, and Py/Py to correspond to the DNA base pair in the minor groove to be bound.

8. A tandem-linked polyamide of claim 1 having the formula:

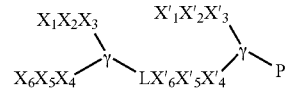

wherein γ is a chiral hairpin linkage derived from R-2,4-diaminobutyric acid;

$X_1/X_6$, $X_2/X_5$, $X_3/X_4$, $X'_1/X'_6$, $X'_2/X'_5$, and $X'_3/X'_4$ represent six carboxamide binding pairs which bind DNA base pairs wherein at least one binding pair is Hp/Py or Py/Hp and the other binding pair(s) is(are) selected from the group consisting of Py/Im, Im/Py, and Py/Py to correspond to the DNA base pair in the minor groove to be bound;

L represents an amino acid linking group selected from the group consisting of β-alanine and 5-aminovaleric acid (δ); and P represents zero to ten polyamides of claim 1.

9. A tandem-linked polyamide of claim 1 having the formula:

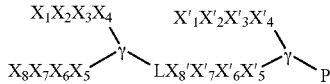

wherein γ is a chiral hairpin linkage derived from R-2,4-diaminobutyric acid;

$X_1/X_8$, $X_2/X_7$, $X_3/X_6$, $X_4/X_5$, $X'_1/X'_8$, $X'_2/X'_7$, $X'_3/X'_6$, and $X'_4/X'_5$ represent eight carboxamide binding pairs which bind DNA base pairs wherein at least one binding pair is Hp/Py or Py/Hp and the other binding pair(s) is(are) selected from the group consisting of Py/Im, Im/Py, and Py/Py to correspond to the DNA base pair in the minor groove to be bound;

L represents an amino acid linking group selected from the group consisting of β-alanine and 5-aminovaleric acid (δ), and P represents zero to ten polyamides of claim 1.

10. A tandem-linked polyamide of claim 1 having the formula:

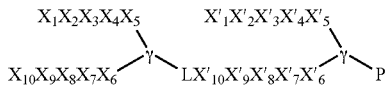

wherein γ is a chiral hairpin linkage derived from R-2,4-diaminobutyric acid;

$X_1/X_{10}$, $X_2/X_9$, $X_3/X_8$, $X_4/X_7$, $X_5/X_6$, $X'_1/X'_{10}$, $X'_2/X'_9$, $X'_3/X'_8$, $X'_4/X'_7$, and $X'_5/X'_6$ represent ten carboxamide binding pairs which bind DNA base pairs wherein at least one binding pair is Hp/Py or Py/Hp and the other binding pair(s) is(are) selected from the group consisting of Py/Im, Im/Py, and Py/Py to correspond to the DNA base pair in the minor groove to be bound;

L represents an amino acid linking group selected from the group consisting of β-alanine and 5-aminovaleric acid (δ); and P represents zero to ten polyamides of claim 1.

11. A tandem-linked polyamide of claim 1 having the formula:

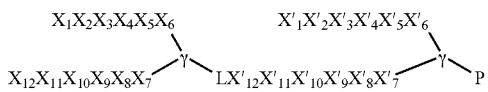

wherein γ is a chiral hairpin linkage derived from R-2,4-diaminobutyric acid;

$X_1/X_{12}$, $X_2/X_{11}$, $X_3/X_{10}$, $X_4/X_9$, $X_5/X_8$, $X_6/X_7$, $X'_1/X'_{12}$, $X'_2/X'_{11}$, $X'_3/X'_{10}$, $X'_4/X'_9$, $X'_5/X'_8$ and $X'_6/X'_7$ represent twelve carboxamide binding pairs which bind DNA base pairs wherein at least one binding pair is Hp/Py or Py/Hp and the other binding pair(s) is(are) selected from the group consisting of Py/Im, Im/Py, and Py/Py to correspond to the DNA base pair in the minor groove to be bound;

L represents an amino acid linking group selected from the group consisting of β-alanine and 5-aminovaleric acid (δ); and P represents zero to ten polyamides of claim 1.

12. A tandem-linked polyamide comprising a first and second polyamide wherein said first polyamide is a polyamide having the formula:

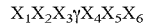

wherein γ is a chiral hairpin linkage derived from R-2,4-diaminobutyric acid; and $X_1/X_6$, $X_2/X_5$, and $X_3/X_4$ represent three carboxamide binding pairs which bind DNA base pairs wherein at least one binding pair is Hp/Py or Py/Hp and the other binding pair(s) is(are) selected from the group consisting of Py/Im, Im/Py, and Py/Py to correspond to the DNA base pair in the minor groove to be bound; said second polyamide is a polyamide according to claim 5, 6, or 7; and said first and second polyamides being linked by an amino acid linking group selected from the group consisting of β-alanine and 5-aminovaleric acid (δ) bound to the γ-residue of said first polyamide and the carboxy tail of said second polyamide.

13. A tandem-linked polyamide comprising a first and second polyamide wherein said first polyamide is a polyamide having the formula:

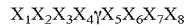

wherein γ is a chiral hairpin linkage derived from R-2,4-diaminobutyric acid; and $X_1/X_8$, $X_2/X_7$, $X_3/X_6$, and $X_4/X_5$ represent four carboxamide binding pairs which bind DNA base pairs wherein at least one binding pair is Hp/Py or Py/Hp and the other binding pair(s) is(are) selected from the group consisting of Py/Im, Im/Py, and Py/Py to correspond to the DNA base pair in the minor groove to be bound; said second polyamide is a polyamide according to claim 4, 6 or 7; and said first and second polyamides being linked by an amino acid linking group selected from the group consisting of β-alanine and 5-aminovaleric acid (δ) bound to the γ-residue of said first polyamide and the carboxy tail of said second polyamide.

14. A tandem-linked polyamide comprising a first and second polyamide wherein said first polyamide is a polyamide having the formula:

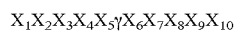

wherein γ is a chiral hairpin linkage derived from R-2,4-diaminobutyric acid; and $X_1/X_{10}$, $X_2/X_9$, $X_3/X_8$, $X_4/X_7$, and $X_5/X_6$ represent five carboxamide binding pairs which bind DNA base pairs wherein at least one binding pair is Hp/Py or Py/Hp and the other binding pair(s) is(are) selected from the group consisting of Py/Im, Im/Py, and Py/Py to correspond to the DNA base pair in the minor groove to be bound; said second polyamide is a polyamide according to claim 4, 5, or 7; and said first and second polyamides being linked by an amino acid linking group selected from the group consisting of β-alanine and 5-aminovaleric acid (δ) bound to the γ-residue of said first polyamide and the carboxy tail of said second polyamide.

15. A tandem-linked polyamide comprising a first and second polyamide wherein said first polyamide is a polyamide having the formula:

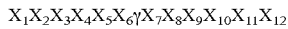

wherein γ is a chiral hairpin linkage derived from R-2,4-diaminobutyric acid; and $X_1/X_{12}$, $X_2/X_{11}$, $X_3/X_{10}$, $X_4/X_9$, $X_5/X_8$, and $X_6/X_7$ represent six carboxamide binding pairs which bind DNA base pairs wherein at least one binding pair is Hp/Py or Py/Hp and the other binding pair(s) is(are) selected from the group consisting of Py/Im, Im/Py, and Py/Py to correspond to the DNA base pair in the minor groove to be bound; said second polyamide is a polyamide according to claim 4, 5, or 6; and said first and second polyamides being linked by an amino acid linking group selected from the group consisting of β-alanine and 5-aminovaleric acid (δ) bound to the γ-residue of said first polyamide and the carboxy tail of said second polyamide.

16. A tandem-linked polyamide of claim 1 having the formula:

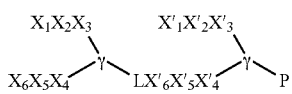

wherein γ is a chiral hairpin linkage derived from R-2,4-diaminobutyric acid;

$X_1/X_6$, $X_2/X_5$, $X_3/X_4$, $X'_1/X'_6$, $X'_2/X'_5$, and $X'_3/X'_4$ represent six carboxamide binding pairs which bind DNA base pairs wherein at least one binding pair is Hp/Py or Py/Hp and the other binding pair(s) is(are) selected from the group consisting of Py/Im, Im/Py, and Py/Py to correspond to the DNA base pair in the minor groove to be bound;

L represents an amino acid linking group selected from the group consisting of β-alanine and 5-aminovaleric acid (δ); and wherein P represents zero to eight polyamides of claim 1.

17. A tandem-linked polyamide of claim 1 having the formula:

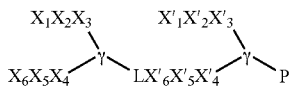

wherein γ is a chiral hairpin linkage derived from R-2,4-diaminobutyric acid;

$X_1/X_6$, $X_2/X_5$, $X_3/X_4$, $X'_1/X'_6$, $X'_2/X'_5$, and $X'_3/X'_4$ represent six carboxamide binding pairs which bind DNA base pairs wherein at least one binding pair is Hp/Py or Py/Hp and the other binding pair(s) is(are) selected from the group consisting of Py/Im, Im/Py, and Py/Py to correspond to the DNA base pair in the minor groove to be bound;

L represents an amino acid linking group selected from the group consisting of β-alanine and 5-aminovaleric acid (δ); and wherein P represents zero to six polyamides of claim 1.

18. A tandem-linked polyamide of claim 1 having the formula:

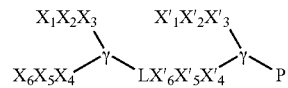

wherein γ is a chiral hairpin linkage derived from R-2,4-diaminobutyric acid;

$X_1/X_6$, $X_2/X_5$, $X_3/X_4$, $X'_1/X'_6$, $X'_2/X'_5$, and $X'_3/X'_4$ represent six carboxamide binding pairs which bind DNA base pairs wherein at least one binding pair is Hp/Py or Py/Hp and the other binding pair(s) is(are) selected from the group consisting of Py/Im, Im/Py, and Py/Py to correspond to the DNA base pair in the minor groove to be bound;

L represents an amino acid linking group selected from the group consisting of β-alanine and 5-aminovaleric acid (δ); and wherein P represents zero to four polyamides of claim 1.

19. A tandem-linked polyamide of claim 1 having the formula:

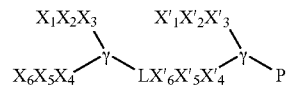

wherein γ is a chiral hairpin linkage derived from R-2,4-diaminobutyric acid;

$X_1/X_6$, $X_2/X_5$, $X_3/X_4$, $X'_1/X'_6$, $X'_2/X'_5$, and $X'_3/X'_4$ represent six carboxamide binding pairs which bind DNA base pairs wherein at least one binding pair is Hp/Py or Py/Hp and the other binding pair(s) is(are) selected from the group consisting of Py/Im, Im/Py, and Py/Py to correspond to the DNA base pair in the minor groove to be bound;

L represents an amino acid linking group selected from the group consisting of β-alanine and 5-aminovaleric acid (δ); and wherein P represents zero to two polyamides of claim 1.

20. A polyamide of claim 1 further comprising an R-2 amino group attached to a detectable label.

21. A polyamide of claim 1 selected from the group consisting of:

ImPyPy-(R)$^{H_2N}$γ-PyPyPy-β-Dp;

ImPyPy-(S)$^{H_2N}$γ-PyPyPy-β-Dp;

ImPyPy-(R)$^{H_2N}$γ-PyPyPy-β-EtOH;

ImPyPy-(R)$^{Ac}$γ-PyPyPy-β-Dp;

ImPyPy-(S)$^{Ac}$γ-PyPyPy-β-Dp;

ImPyPy-(R)(ImPyPy-(R)$^{H_2N}$γ-PyPyPy-β-)$^{HN}$γ-PyPyPy-β-Dp;

ImPyPy-(R)(ImPyPy-(R)$^{H_2N}$γ-PyPyPy-δ-)$^{HN}$γ-PyPyPy-β-Dp;

ImPyPy-(R)(ImPyPy-(R)$^{EDTA}$γ-PyPyPy-δ-)$^{HN}$γ-PyPyPy-β-Dp; and a pharmaceutically acceptable salt thereof.

22. A tandem-linked polyamide of claim 1 having the formula:

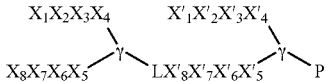

wherein γ is a chiral hairpin linkage derived from R-2,4-diaminobutyric acid;

$X_1/X_8$, $X_2/X_7$, $X_3/X_6$, $X_4/X_5$, $X'_1/X'_8$, $X'_2/X'_7$, $X'_3/X'_6$, and $X'_4/X'_5$ represent eight carboxamide binding pairs which bind DNA base pairs wherein at least one binding pair is Hp/Py or Py/Hp and the other binding pair(s) is(are) selected from the group consisting of Py/Im, Im/Py, and Py/Py to correspond to the DNA base pair in the minor groove to be bound;

L represents an amino acid linking group selected from the group consisting of β-alanine and 5-aminovaleric acid (δ), and wherein P represents zero to eight polyamides of claim 1.

23. A tandem-linked polyamide of claim 1 having the formula:

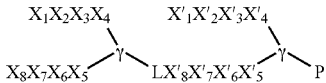

wherein γ is a chiral hairpin linkage derived from R-2,4-diaminobutyric acid;

$X_1/X_8$, $X_2/X_7$, $X_3/X_6$, $X_4/X_5$, $X'_1/X'_8$, $X'_2/X'_7$, $X'_3/X'_6$, and $X'_4/X'_5$ represent eight carboxamide binding pairs which bind DNA base pairs wherein at least one binding pair is Hp/Py or Py/Hp and the other binding pair(s) is(are) selected from the group consisting of Py/Im, Im/Py, and Py/Py to correspond to the DNA base pair in the minor groove to be bound;

L represents an amino acid linking group selected from the group consisting of β-alanine and 5-aminovaleric acid (δ), and wherein P represents zero to six polyamides of claim 1.

24. A tandem-linked polyamide of claim 1 having the formula:

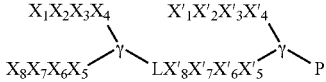

wherein γ is a chiral hairpin linkage derived from R-2,4-diaminobutyric acid;

$X_1/X_8$, $X_2/X_7$, $X_3/X_6$, $X_4/X_5$, $X'_1/X'_8$, $X'_2/X'_7$, $X'_3/X'_6$, and $X'_4/X'_5$ represent eight carboxamide binding pairs which bind DNA base pairs wherein at least one binding pair is Hp/Py or Py/Hp and the other binding pair(s) is(are) selected from the group consisting of Py/Im, Im/Py, and Py/Py to correspond to the DNA base pair in the minor groove to be bound;

L represents an amino acid linking group selected from the group consisting of β-alanine and 5-aminovaleric acid (δ), and wherein P represents zero to four polyamides of claim 1.

25. A tandem-linked polyamide of claim 1 having the formula:

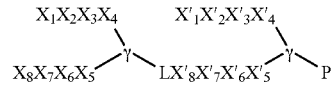

wherein γ is a chiral hairpin linkage derived from R-2,4-diaminobutyric acid;

$X_1/X_8$, $X_2/X_7$, $X_3/X_6$, $X_4/X_5$, $X'_1/X'_8$, $X'_2/X'_7$, $X'_3/X'_6$, and $X'_4/X'_5$ represent eight carboxamide binding pairs which bind DNA base pairs wherein at least one binding pair is Hp/Py or Py/Hp and the other binding pair(s) is(are) selected from the group consisting of Py/Im, Im/Py, and Py/Py to correspond to the DNA base pair in the minor groove to be bound;

L represents an amino acid linking group selected from the group consisting of β-alanine and 5-aminovaleric acid (δ), and wherein P represents zero to two polyamides of claim 1.

26. A tandem-linked polyamide of claim 1 having the formula:

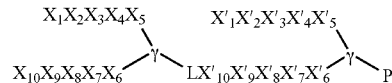

wherein γ is a chiral hairpin linkage derived from R-2,4-diaminobutyric acid;

$X_1/X_{10}$, $X_2/X_9$, $X_3/X_8$, $X_4/X_7$, $X_5/X_6$, $X'_1/X'_{10}$, $X'_2/X'_9$, $X'_3/X'_8$, $X'_4/X'_7$, and $X'_5/X'_6$ represent ten carboxamide binding pairs which bind DNA base pairs wherein at least one binding pair is Hp/Py or Py/Hp and the other binding pair(s) is(are) selected from the group consisting of Py/Im, Im/Py, and Py/Py to correspond to the DNA base pair in the minor groove to be bound;

L represents an amino acid linking group selected from the group consisting of β-alanine and 5-aminovaleric acid (δ); and wherein P represents zero to eight polyamides of claim 1.

27. A tandem-linked polyamide of claim 1 having the formula:

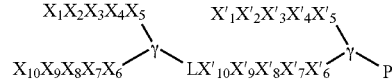

wherein γ is a chiral hairpin linkage derived from R-2,4-diaminobutyric acid;

$X_1/X_{10}$, $X_2/X_9$, $X_3/X_8$, $X_4/X_7$, $X_5/X_6$, $X'_1/X'_{10}$, $X'_2/X'_9$, $X'_3/X'_8$, $X'_4/X'_7$, and $X'_5/X'_6$ represent ten carboxamide binding pairs which bind DNA base pairs wherein at least one binding pair is Hp/Py or Py/Hp and the other binding pair(s) is(are) selected from the group consisting of Py/Im, Im/Py, and Py/Py to correspond to the DNA base pair in the minor groove to be bound;

L represents an amino acid linking group selected from the group consisting of β-alanine and 5-aminovaleric acid (δ); and wherein P represents zero to six polyamides of claim 1.

28. A tandem-linked polyamide of claim 1 having the formula:

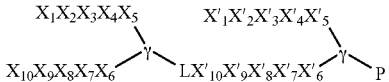

wherein γ is a chiral hairpin linkage derived from R-2,4-diaminobutyric acid;

$X_1/X_{10}$, $X_2/X_9$, $X_3/X_8$, $X_4/X_7$, $X_5/X_6$, $X'_1/X'_{10}$, $X'_2/X'_9$, $X'_3/X'_8$, $X'_4/X'_7$, and $X'_5/X'_6$ represent ten carboxamide binding pairs which bind DNA base pairs wherein at least one binding pair is Hp/Py or Py/Hp and the other binding pair(s) is(are) selected from the group consisting of Py/Im, Im/Py, and Py/Py to correspond to the DNA base pair in the minor groove to be bound;

L represents an amino acid linking group selected from the group consisting of β-alanine and 5-aminovaleric acid (δ); and wherein P represents zero to four polyamides of claim 1.

29. A tandem-linked polyamide of claim 1 having the formula:

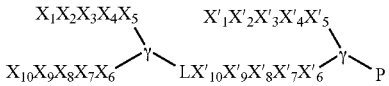

wherein γ is a chiral hairpin linkage derived from R-2,4-diaminobutyric acid;

$X_1/X_{10}$, $X_2/X_9$, $X_3/X_8$, $X_4/X_7$, $X_5/X_6$, $X'_1/X'_{10}$, $X'_2/X'_9$, $X'_3/X'_8$, $X'_4/X'_7$, and $X'_5/X'_6$ represent ten carboxamide binding pairs which bind DNA base pairs wherein at least one binding pair is Hp/Py or Py/Hp and the other binding pair(s) is(are) selected from the group consisting of Py/Im, Im/Py, and Py/Py to correspond to the DNA base pair in the minor groove to be bound;

L represents an amino acid linking group selected from the group consisting of β-alanine and 5-aminovaleric acid (δ); and wherein P represents zero to two polyamides of claim 1.

30. A tandem-linked polyamide of claim 1 having the formula:

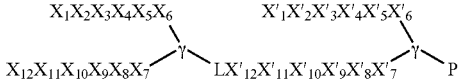

wherein γ is a chiral hairpin linkage derived from R-2,4-diaminobutyric acid;

$X_1/X_{12}$, $X_2/X_{11}$, $X_3/X_{10}$, $X_4/X_9$, $X_5/X_8$, $X_6/X_7$, $X'_1/X'_{12}$, $X'_2/X'_{11}$, $X'_3/X'_{10}$, $X'_4/X'_9$, $X'_5/X'_8$ and $X'_6/X'_7$ represent twelve carboxamide binding pairs which bind DNA base pairs wherein at least one binding pair is Hp/Py or Py/Hp and the other binding pair(s) is(are) selected from the group consisting of Py/Im, Im/Py, and Py/Py to correspond to the DNA base pair in the minor groove to be bound;

L represents an amino acid linking group selected from the group consisting of β-alanine and 5-aminovaleric acid (δ); and wherein P represents zero to eight polyamides of claim 1.

31. A tandem-linked polyamide of claim 1 having the formula:

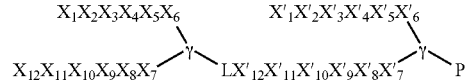

wherein γ is a chiral hairpin linkage derived from R-2,4-diaminobutyric acid;

$X_1/X_{12}$, $X_2/X_{11}$, $X_3/X_{10}$, $X_4/X_9$, $X_5/X_8$, $X_6/X_7$, $X'_1/X'_{12}$, $X'_2/X'_{11}$, $X'_3/X'_{10}$, $X'_4/X'_9$, $X'_5/X'_8$ and $X'_6/X'_7$ represent twelve carboxamide binding pairs which bind DNA base pairs wherein at least one binding pair is Hp/Py or Py/Hp and the other binding pair(s) is(are) selected from the group consisting of Py/Im, Im/Py, and Py/Py to correspond to the DNA base pair in the minor groove to be bound;

L represents an amino acid linking group selected from the group consisting of β-alanine and 5-aminovaleric acid (δ); and wherein P represents zero to six polyamides of claim 1.

32. A tandem-linked polyamide of claim 1 having the formula:

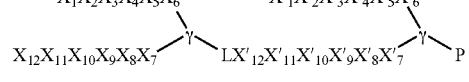

wherein γ is a chiral hairpin linkage derived from R-2,4-diaminobutyric acid;

$X_1/X_{12}$, $X_2/X_{11}$, $X_3/X_{10}$, $X_4/X_9$, $X_5/X_8$, $X_6/X_7$, $X'_1/X'_{12}$, $X'_2/X'_{11}$, $X'_3/X'_{10}$, $X'_4/X'_9$, $X'_5/X'_8$ and $X'_6/X'_7$ represent twelve carboxamide binding pairs which bind DNA base pairs wherein at least one binding pair is Hp/Py or Py/Hp and the other binding pair(s) is(are) selected from the group consisting of Py/Im, Im/Py, and Py/Py to correspond to the DNA base pair in the minor groove to be bound;

L represents an amino acid linking group selected from the group consisting of β-alanine and 5-aminovaleric acid (δ); and wherein P represents zero to four polyamides of claim 1.

33. A tandem-linked polyamide of claim 1 having the formula:

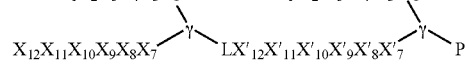

wherein γ is a chiral hairpin linkage derived from R-2,4-diaminobutyric acid;

$X_1/X_{12}$, $X_2/X_{11}$, $X_3/X_{10}$, $X_4/X_9$, $X_5/X_8$, $X_6/X_7$, $X'_1/X'_{12}$, $X'_2/X'_{11}$, $X'_3/X'_{10}$, $X'_4/X'_9$, $X'_5/X'_8$ and $X'_6/X'_7$ represent twelve carboxamide binding pairs which bind DNA base pairs wherein at least one binding pair is Hp/Py or Py/Hp and the other binding pair(s) is(are) selected from the group consisting of Py/Im, Im/Py, and Py/Py to correspond to the DNA base pair in the minor groove to be bound;

L represents an amino acid linking group selected from the group consisting of β-alanine and 5-aminovaleric acid (δ); and wherein P represents zero to two polyamides of claim 1.

* * * * *